United States Patent
Nelson et al.

(10) Patent No.: US 6,376,507 B1
(45) Date of Patent: Apr. 23, 2002

(54) NK-1 RECEPTOR ANTAGONISTS FOR THE TREATMENT OF NEURONAL INJURY AND STROKE

(75) Inventors: Robert B. Nelson, Gales Ferry; John A. Lowe, III, Stonington, both of CT (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 09/099,289

(22) Filed: Jun. 18, 1998

Related U.S. Application Data

(63) Continuation of application No. 08/354,702, filed on Dec. 12, 1994, now abandoned.

(51) Int. Cl.⁷ .................... A61K 31/44; A61K 31/415
(52) U.S. Cl. ........................... 514/294; 514/305
(58) Field of Search ................... 514/294, 305

(56) References Cited

U.S. PATENT DOCUMENTS

| | | | | |
|---|---|---|---|---|
| 5,162,339 A | * | 11/1992 | Lowe, III | 514/305 |
| 5,422,354 A | * | 6/1995 | Lowe, III | 514/294 |
| 5,527,808 A | * | 6/1996 | Lowe, III | 514/294 |
| 5,641,786 A | * | 6/1997 | Lowe, III | 514/294 |
| 5,698,568 A | * | 12/1997 | Lowe, III | 514/291 |
| 5,703,065 A | * | 12/1997 | Howard, Jr. | 514/183 |
| 5,807,867 A | * | 9/1998 | Ito et al. | 514/305 |
| 5,854,256 A | * | 12/1998 | Lowe, III | 514/294 |
| 5,939,433 A | * | 8/1999 | Ito et al. | 514/305 |

FOREIGN PATENT DOCUMENTS

| | | | |
|---|---|---|---|
| CA | 2164804 | * | 6/1996 |
| EP | 712 778 | * | 7/1996 |
| WO | 91/18899 | * | 12/1991 |
| WO | 92/01688 | * | 2/1992 |
| WO | 92/12151 | * | 7/1992 |
| WO | 92/15585 | * | 9/1992 |
| WO | 93/19064 | * | 9/1993 |
| WO | 94/04496 | * | 3/1994 |

* cited by examiner

*Primary Examiner*—Ralph Gitomer
*Assistant Examiner*—Devesh Khare
(74) *Attorney, Agent, or Firm*—Peter C. Richardson; Paul H. Ginsburg; A. David Joran

(57) ABSTRACT

The present invention relates to a method of treating or preventing a disorder selected from stroke, epilepsy, head trauma, spinal cord trauma, ischemic neuronal damage such as cerebral ischemic damage from stroke or vascular occlusion (e.g., during open heart surgery), excitotoxic neuronal damage (e.g., in stroke or epilepsy) and amyotrophic lateral sclerosis in mammals, including humans, using an NK-1 antagonist. It also relates to a method of treating or preventing such disorders in mammals, including humans, using certain quinuclidine derivatives, piperidine derivatives, pyrrolidine derivatives, azanorbornane derivatives, ethylene diamine derivatives and related compounds that are substance P receptor antagonists.

1 Claim, No Drawings

US 6,376,507 B1

NK-1 RECEPTOR ANTAGONISTS FOR THE TREATMENT OF NEURONAL INJURY AND STROKE

This application is a continuation of nonprovisional application Ser. No. 08/354,702, filed Dec. 12, 1994, now abandoned.

The present invention relates to a method of treating or preventing a disorder selected from stroke, epilepsy, head trauma, spinal cord trauma, ischemic neuronal damage such as cerebral ischemic damage from stroke or vascular occlusion (e.cf, during open heart surgery), excitotoxic neuronal damage (e.g., in stroke or epilepsy) and amyotrophic lateral sclerosis in mammals, including humans, using an NK-1 antagonist. It also relates to a method of treating or preventing such disorders in mammals, including humans, using certain quinuclidine derivatives, piperidine derivatives, pyrrolidine derivatives, azanorbornane derivatives, ethylene diamine derivatives and related compounds that are substance P receptor antagonists.

The following references refer, collectively, to quinuclidine, piperidine, ethylene diamine, pyrrolidine and azanorbornane derivatives and related compounds that exhibit activity as substance P receptor antagonists: U.S. Pat. No. 5,162,339, which issued on Nov. 11, 1992; U.S. Pat. No. 5,232,929, which issued on Aug. 3, 1993; World Patent Application WO 92/20676, published Nov. 26, 1992; World Patent Application WO 93/00331, published Jan. 7, 1993; World Patent Application WO 92/21677, published Dec. 10, 1992; World Patent Application WO 93/00330, published Jan. 7, 1993; World Patent Application WO 93/06099, published Apr. 1, 1993; World Patent Application WO 93/10073, published May 27, 1993; World Patent Application WO 92/06079, published Apr. 16, 1992; World Patent Application WO 92/12151, published Jul. 23, 1992; World Patent Application WO 92/15585, published Sep. 17, 1992; World Patent Application WO 93/10073, published May 27, 1993; World Patent Application WO 93/19064, published Sep. 30, 1993; World Patent Application WO 94/08997, published Apr. 28, 1994; World Patent Application WO 94/04496, published Mar. 3, 1994; U.S. patent application Ser. No. 988,653, filed Dec. 10, 1992; U.S. patent application Ser. No. 026,382, filed Mar. 4, 1993; U.S. patent application Ser. No. 123,306, filed Sep. 17, 1993, and U.S. patent application Ser. No. 072,629, filed Jun. 4, 1993. All of the foregoing World Patent Applications designate the United States and were filed in the U.S. Receiving Office of the PCT. The foregoing patents and patent applications are incorporated herein by reference in their entirety.

SUMMARY OF THE INVENTION

This invention relates to a method of treating or preventing a disorder selected from stroke, epilepsy, head trauma, spinal cord trauma, ischemic neuronal damage such as cerebral ischemic damage from stroke or vascular occlusion (e.g., during open heart surgery), excitotoxic neuronal damage (e.g., in stroke or epilepsy) and amyotrophic lateral sclerosis in a mammal, including a human, comprising administering to such mammal an amount of a substance P receptor antagonist that is effective in treating or preventing such disorder.

This invention also relates to a method of treating or preventing a disorder selected from stroke, epilepsy, head trauma, spinal cord trauma, ischemic neuronal damage such as cerebral ischemic damage from stroke or vascular occlusion (e.g., during open heart surgery), excitotoxic neuronal damage (e.g., in stroke or epilepsy) and amyotrophic lateral sclerosis in a mammal, including a human, comprising administering to such mammal an amount of a NK-1 receptor antagonist that is effective in treating or preventing such disorder.

This invention also relates to a method of treating or preventing a disorder selected from stroke, epilepsy, head trauma, spinal cord trauma, ischemic neuronal damage such as cerebral ischemic damage from stroke or vascular occlusion (e.g., during open heart surgery), excitotoxic neuronal damage (e.g., in stroke or epilepsy) and amyotrophic lateral sclerosis in a mammal, including a human, comprising administering to said mammal an amount of a compound of the formula

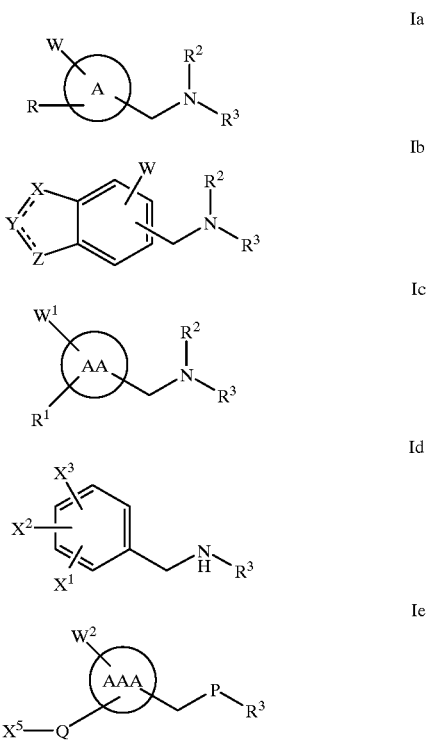

wherein A is a ring system selected from phenyl, naphthyl, thienyl, quinolinyl and indolinyl, and wherein the sidechain containing $NR^2R^3$ is attached to a carbon atom of ring system A;

AA is an aryl group selected from phenyl, naphthyl, thienyl, dihydroquinolinyl and indolinyl, and wherein the sidechain containing $NR^2R^3$ is attached to a carbon atom of AA;

AAA is an aryl group selected from phenyl, naphthyl, thienyl, dihydroquinolinyl and indolinyl, and wherein the —$CH_2PR^3$ sidechain is attached to a carbon atom of ring AAA;

P is $NR^2$, O, S, SO or $SO_2$;

Q is $SO_2$, NH,

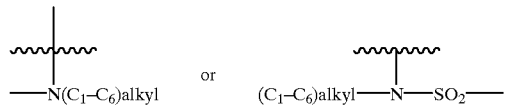

wherein the point of attachment of said

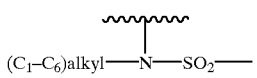

to ring AAA is the nitrogen atom and the point of attachment to $X^5$ is the sulfur atom;

$W^1$ is hydrogen, halo or $(C_1-C_6)$alkyl, S—$(C_1-C_3)$alkyl, halo or $(C_1-C_6)$alkoxy optionally substituted with from one to three fluorine atoms;

$W^2$ is hydrogen, $(C_1-C_6)$alkyl, S—$(C_1-C_3)$alkyl, halo or $(C_1-C_6)$alkoxy optionally substituted with from one to three fluorine atoms;

W is hydrogen, $(C_1-C_6)$alkyl optionally substituted with from one to three fluorine atoms, —S(O)$_v$—$(C_1-C_6)$alkyl wherein v is zero, one or two, halo or $(C_1-C_6)$alkoxy optionally substituted with from one to three fluorine atoms;

$X^1$ is hydrogen, $(C_1-C_{10})$alkoxy optionally substituted with from one to three fluorine atoms or $(C_1-C_{10})$alkyl optionally substituted with from one to three fluorine atoms;

$X^2$ and $X^3$ are independently selected from hydrogen, halo, nitro, $(C_1-C_{10})$alkyl optionally substituted with from one to three fluorine atoms, $(C_1-C_{10})$alkoxy optionally substituted with from one to three fluorine atoms, trifluoromethyl, hydroxy, phenyl, cyano, amino, $(C_1-C_6)$-alkylamino, di-$(C_1-C_6)$alkylamino,

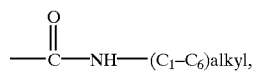

$(C_1-C_6)$—

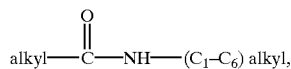

hydroxy$(C_1-C_4)$alkyl, $(C_1-C_4)$alkoxy$(C_1-C_4)$alkyl,

$X^5$ is a four to six membered heterocyclic ring containing from one to three heteroatoms selected from sulfur, nitrogen and oxygen (e.g., thiazolyl, pyrrolyl, thienyl, triazolyl, oxazolyl, oxadiazolyl, thiadiazolyl or imidazolyl), wherein said heterocyclic ring may optionally be substituted with from one to three substituents, preferably with from zero to two substituents, independently selected from phenyl, $(C_1-C_6)$alkyl optionally substituted with from one to three fluorine atoms, $(C_1-C_6)$alkoxy optionally substituted with from one to three fluorine atoms and halo;

R is a 4, 5 or 6 membered heterocyclic ring containing from one to three heteroatoms selected from oxygen, nitrogen and sulfur (e.g., thiazolyl, azetidinyl, pyrrolyl, pyrazolyl, 1,2,3-triazolyl, 1,2,4-triazolyl, isothiazolyl, imidazolyl, isoxazolyl, or oxazolyl) wherein said heterocyclic ring may contain from zero to three double bonds and may optionally be substituted with one or more substituents, preferably one or two substituents, independently selected from $(C_1-C_6)$alkyl optionally substituted with from one to three fluorine atoms and $(C_1-C_6)$ alkoxy optionally substituted with from one to three fluorine atoms;

$R^1$ is selected from amino, $(C_1-C_6)$alkylamino, di-$(C_1-C_6)$alkylamino, —S(O)$_v$—$(C_1-C_{10})$-alkyl wherein v is zero, one or two, —S(O)$_v$-aryl wherein v is zero, one or two, —O-aryl, —SO$_2$NR$^4$R$^5$ wherein each of R$^4$ and R$^5$ is, independently, $C_1-C_6$)alkyl, or R$^4$ and R$^5$, together with the nitrogen to which they are attached, form a saturated ring containing one nitrogen and from 3 to 6 carbons,

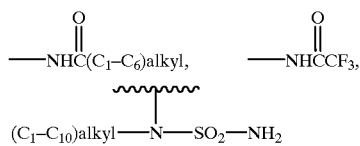

wherein one or both of the alkyl moieties may optionally be substituted with from one to three fluorine atoms, —N(SO$_2$—$(C_1-C_{10})$alkyl)$_2$ and

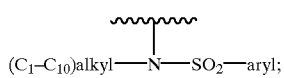

and wherein the aryl moieties of said —S(O)$_v$-aryl, —O-aryl and

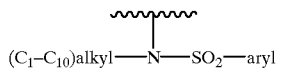

are independently selected from phenyl and benzyl and may optionally be substituted with from one to three substituents independently selected from $(C_1-C_4)$alkyl, $(C_1-C_4)$alkoxy and halo;

or $R^1$ is a group having the formula

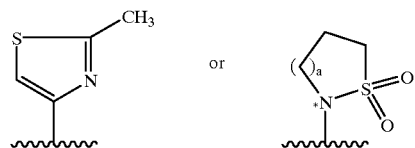

wherein a is 0, 1 or 2 and the asterisk represents a position meta to the $R^2R^3NCH_2$ side chain;

the dotted lines in formula Ib represent that one of the X—Y and Y—Z bonds may optionally be a double bond;

X is selected from =CH—, —CH$_2$—, —O—, —S—, —SO—, —SO$_2$—, —N(R$^4$)—, —NH—, =N—, —CH[$(C_1-C_6)$alkyl]—, =C[$(C_1-C_6)$alkyl]—, —CH$(C_6H_5)$— and =C$(C_6H_5)$—;

Y is selected from C=O, C=NR$^4$, C=S, =CH—, —CH$_2$—, =C[$(C_1-C_6)$alkyl]—, —CH[$(C_1-C_6)$alkyl]—, =C$(C_6H_5)$—, —CH$(C_6H_5)$—, =N—, —NH—, —N(R$^4$)—, =C(halo)—, =C(OR$^4$)—, =C(SR$^4$)—, =C(NR$^4$)—, —O—, —S— and SO$_2$, wherein the phenyl moieties of said =C$(C_6H_5)$— and —CH$(C_6H_5)$— may optionally be substituted with from one to three substituents independently selected from trifluoromethyl and halo, and wherein the alkyl moieties of said =[(C$_1$–C$_6$)alkyl]— and —CH[C$_1$–C$_6$)alkyl]— may optionally be substituted with from one to three fluorine atoms;

Z is selected from =CH—, —CH$_2$—, =N—, —NH—, —S—, —N(R$^4$)—, =C(C$_6$H$_5$)—, —CH(C$_6$H$_5$)—, =C[(C$_1$–C$_6$)alkyl]— and —CH[(C$_1$–C$_6$)alkyl]—;

or X, Y and Z, together with the two carbon atoms shared between the benzo ring and the XYZ ring, form a fused pyridine or pyrimidine ring;

R$^4$ is (C$_1$–C$_6$)alkyl or phenyl;

R$^2$ is hydrogen or —CO$_2$(C$_1$–C$_{10}$)alkyl;

R$^3$ is selected from

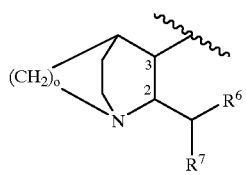

II

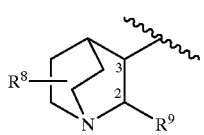

III

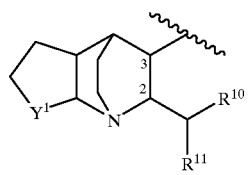

IV

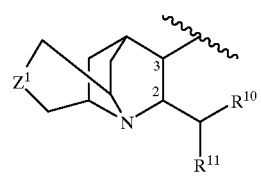

V

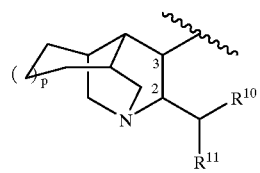

VI

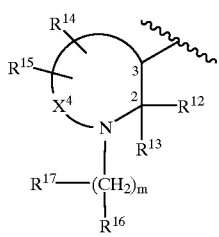

VII

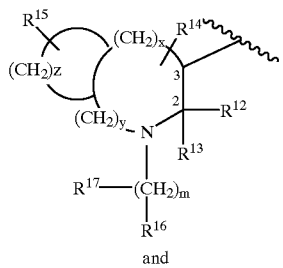

VIII

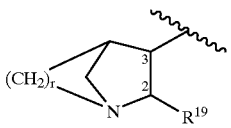

and

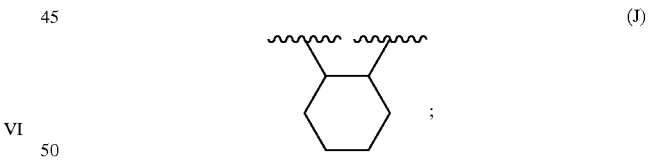

IX wherein R$^6$ and R$^{10}$ are independently selected from furyl, thienyl, pyridyl, indolyl, biphenyl and phenyl, wherein said phenyl may optionally be substituted with one or two substituents independently selected from halo, (C$_1$–C$_{10}$) alkyl optionally substituted with from one to three fluorine atoms, (C$_1$–C$_{10}$)alkoxy optionally substituted with from one to three fluorine atoms, carboxy, benzyloxycarbonyl and (C$_1$–C$_3$) alkoxy-carbonyl;

R$^7$ is selected from (C$_3$–C$_4$) branched alkyl, (C$_5$–C$_6$) branched alkenyl, (C$_5$–C$_7$)cycloalkyl, and the radicals named in the definition of R$^6$;

R$^8$ is hydrogen or (C$_1$–C$_6$)alkyl;

R$^9$ and R$^{19}$ are independently selected from phenyl, biphenyl, naphthyl, pyridyl, benzhydryl, thienyl and furyl, and R$^9$ and R$^{19}$ may optionally be substituted with from one to three substituents independently selected from halo, (C$_1$–C$_{10}$) alkyl optionally substituted with from one to three fluorine atoms and (C$_1$–C$_{10}$)alkoxy optionally substituted with from one to three fluorine atoms;

Y$^1$ is (CH$_2$)$_l$ wherein l is an integer from one to three, or Y$^1$ is a group of the formula (J)

Z$^1$ is oxygen, sulfur, amino, (C$_1$–C$_3$)alkylamino or (CH$_2$)$_n$, wherein n is zero, one or two;

x is an integer from zero to four;

y is an integer from zero to four;

z is an integer from one to six, wherein the ring containing (CH$_2$)$_z$ may contain from zero to three double bonds, and one of the carbons of (CH$_2$)$_z$ may optionally be replaced by oxygen, sulfur or nitrogen;

o is two or three;

p is zero or one;

r is one, two or three;

R$^{11}$ is thienyl, biphenyl or phenyl optionally substituted with one or two substituents independently selected from halo, (C$_1$–C$_{10}$)alkyl optionally substituted with from one to three fluorine atoms and $(C_1-C_{10})$alkoxy optionally substituted with from one to three fluorine atoms;

$X^4$ is $(CH_2)_q$ wherein q is an integer from 1 to 6, and wherein any one of the carbon-carbon single bonds in said $(CH_2)_q$ may optionally be replaced by a carbon-carbon double bond, and wherein any one of the carbon atoms of said $(CH_2)_q$ may optionally be substituted with $R^{14}$, and wherein any one of the carbon atoms of said $(CH_2)_q$ may optionally be substituted with $R^{15}$;

m is an integer from 0 to 8, and any one of the carbon-carbon single bonds of $(CH_2)_m$, wherein both carbon atoms of such bond are bonded to each other and to another carbon atom in the $(CH_2)_m$ chain, may optionally be replaced by a carbon-carbon double bond or a carbon-carbon triple bond, and any one of the carbon atoms of said $(CH_2)_m$ may optionally be substituted with $R^{17}$;

$R^{12}$ is a radical selected from hydrogen, $(C_1-C_6)$ straight or branched alkyl, $(C_3-C_7)$cycloalkyl wherein one of the carbon atoms may optionally be replaced by nitrogen, oxygen or sulfur; aryl selected from biphenyl, phenyl, indanyl and naphthyl; heteroaryl selected from thienyl, furyl, pyridyl, thiazolyl, isothiazolyl, oxazolyl, isoxazolyl, triazolyl, tetrazolyl and quinolyl; phenyl-$(C_2-C_6)$alkyl, benzhydryl and benzyl, wherein the point of attachment on $R^{12}$ is a carbon atom unless $R^{12}$ is hydrogen, and wherein each of said aryl and heteroaryl groups and the phenyl moieties of said benzyl, phenyl-$(C_2-C_6)$alkyl and benzhydryl may optionally be substituted with one or more substituents independently selected from halo, nitro, $(C_1-C_{10})$alkyl optionally substituted with from one to three fluorine atoms, $(C_1-C_{10})$alkoxy optionally substituted with from one to three fluorine atoms, amino, hydroxy-$(C_1-C_6)$alkyl, $(C_1-C_6)$alkoxy-$(C_1-C_6)$alkyl, $(C_1-C_6)$-alkylamino,

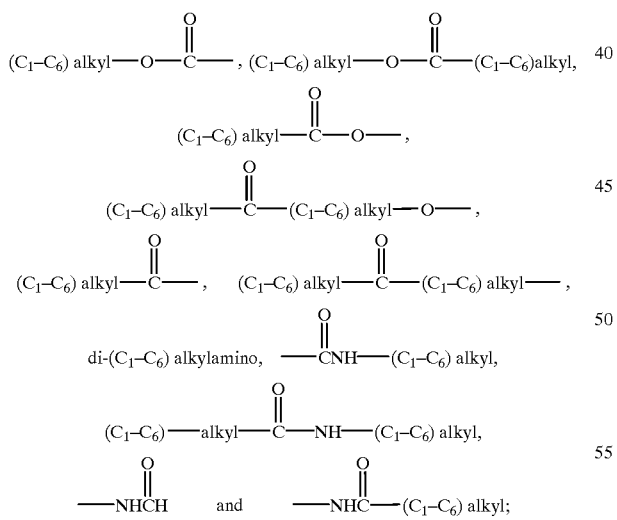

and wherein one of the phenyl moieties of said benzhydryl may optionally be replaced by naphthyl, thienyl, furyl or pyridyl;

$R^{13}$ is hydrogen, phenyl or $(C_1-C_6)$alkyl;

or $R^{12}$ and $R^{13}$, together with the carbon to which they are attached, form a saturated carbocyclic ring having from 3 to 7 carbon atoms wherein one of said carbon atoms that is neither the point of attachment of the spiro ring nor adjacent to it may optionally be replaced by oxygen, nitrogen or sulfur;

$R^{14}$ and $R^{15}$ are each independently selected from hydrogen, hydroxy, halo, amino, oxo (=O), cyano, hydroxy-$(C_1-C_6)$alkyl, $(C_1-C_6)$alkoxy-$(C_1-C_6)$alkyl, $(C_1-C_6)$alkylamino,

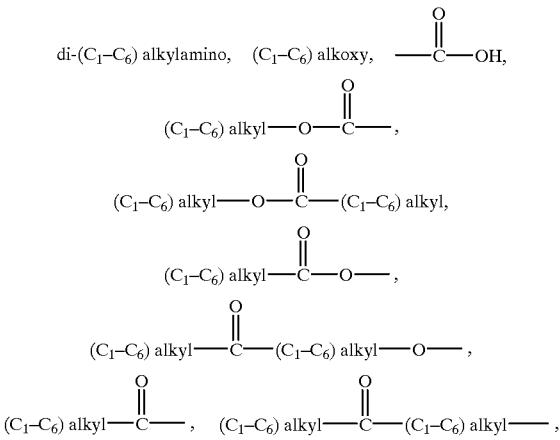

and the radicals set forth in the definition of $R^{12}$;

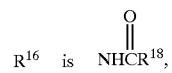

$NHCH_2R^{18}$, $SO_2R^{18}$, $GR^{20}$ $CO_2H$ or one of the radicals set forth in any of the definitions of $R^{12}$, $R^{14}$ and $R^{15}$;

$R^{17}$ is oximino (=NOH) or one of the radicals set forth in any of the definitions of $R^{12}$, $R^{14}$ and $R^{15}$; and $R^{18}$ is $(C_1-C_6)$alkyl, hydrogen, phenyl or phenyl $(C_1-C_6)$ alkyl;

G is selected from the group consisting of $CH_2$, nitrogen, oxygen, sulfur and carbonyl;

$R^{20}$ is a monocyclic or bicyclic heterocycle selected from the group consisting of pyrimidinyl, benzoxazolyl, 2,3-dihydro-3-oxobenzisosulfonazol-2-yl, morpholin-1-yl, thiomorpholin-1-yl, benzofuranyl, benzothienyl, indolyl, isoindolyl, isoquinolinyl, furyl, pyridyl, isothiazolyl, oxazolyl, triazolyl, tetrazolyl, quinolyl, thiazolyl, thienyl, and groups of the formulae

wherein B and D are selected from carbon, oxygen, and nitrogen, and at least one of B and D is other than carbon; E is carbon or nitrogen; n is an integer from 1 to 5; and any one of the carbons of the $(CH_2)_n$ or $(CH_2)_{n+1}$ may be optionally substituted with $(C_1-C_6)$ alkyl or $(C_2-C_6)$spiroalkyl, and either any two of the carbon atoms of said $(CH_2)_n$ and $(CH_2)_{n+1}$ may be bridged by a one or two carbon atom linkage, or any one pair of adjacent carbons of said $(CH_2)_n$ and $(CH_2)_{n+1}$ may form, together with from one to three carbon atoms that are not members of the carbonyl containing ring, a $(C_3-C_5)$ fused carbocyclic ring;

with the proviso that (a) when m is 0, one of $R^{16}$ and $R^{17}$ is absent and the other is hydrogen, (b) when $R^3$ is a group of the formula VIII, $R^{14}$ and $R^{15}$ cannot be attached to the same carbon atom, (c) when $R^{14}$ and $R^{15}$ are attached to the same carbon atom, then either each of $R^{14}$ and $R^{15}$ is independently selected from hydrogen, fluoro, $(C_1-C_6)$alkyl, hydroxy-$(C_1-C_6)$alkyl and $(C_1-C_6)$alkoxy-$(C_1-C_6)$alkyl, or $R^{14}$ and $R^{15}$, together with the carbon to which they are attached, form a $(C_3-C_6)$ saturated carbocyclic ring that forms a spiro compound with the nitrogen-containing ring to which they are attached; (d) $R^{12}$ and $R^{13}$ cannot both be hydrogen; (e) when $R^{14}$ or $R^{15}$ is attached to a carbon atom of X or $(CH_2)_y$ that is adjacent to the ring nitrogen, then $R^{14}$ or $R^{15}$, respectively, must be a substituent wherein the point of attachment is a carbon atom; and (f) neither $R^{14}$, $R^{15}$, $R^{16}$ nor $R^{17}$ can form a ring with $R^{13}$;

or a pharmaceutically acceptable salt thereof, that is effective in treating or preventing such disorder.

The fused bicyclic nucleus of compounds of the formula Ib to which W and the —$CN_2NR^2R^3$ sidechain are attached may be, but is not limited to one of the following groups: benzoxazolyl, benzthiazolyl, benzimidazolyl, benzisoxazolyl, benzoisothiazolyl, indazolyl, indolyl, isoquinolinyl, benzofuryl, benzothienyl, oxindolyl, benzoxazolinonyl, benzthiazolinonyl, benzimidazolinonyl, benzimidazoliniminyl, dihydrobenzothienyl-S,S-dioxide, benztriazolyl, benzthiadiazolyl, benzoxadiazolyl, and quinazolinyl.

Preferred embodiments of this invention include methods of treating or preventing a disorder selected from stroke, epilepsy, head trauma, spinal cord trauma, ischemic neuronal damage such as cerebral ischemic damage from stroke or vascular occlusion (e.g., during open heart surgery), excitotoxic neuronal damage (e.g., in stroke or epilepsy) and amyotrophic lateral sclerosis in a mammal, including a human, that comprise administering to said mammal an amount of a compound as defined in paragraphs (1) through (47A) below, or a pharmaceutically acceptable salt thereof, that is effective in treating or preventing such disorder.

(1) A compound of the formula Ia or Ib wherein the substituents at positions "2" and "3" of the nitrogen containing ring of $R^3$ are in a cis configuration. (When $R^3$ is a group of the formula VII or VIII, "a cis configuration", as used herein, means that the non-hydrogen substituent at position "3" is cis to $R^{12}$).

(2) A compound of the formula Ia wherein $R^3$ is a group of the formula III, VII or IX; $R^2$ is hydrogen; A is phenyl or indolinyl; W is $(C_1-C_3)$alkoxy optionally substituted with from one to five fluorine atoms; and R is thiazolyl, imidazolyl, thiadiazolyl, pyrrolyl or oxazolyl, and R may optionally be substituted with one or two $(C_1-C_3)$alkyl moieties.

(3) A compound of the formula Ib wherein $R^3$ is a group of the formula III, VII or IX; $R^2$ is hydrogen; the fused bicyclic ring system to which W and the —$CH_2NR^2R^3$ sidechain are attached is benzoxazolyl, benzisoxazolyl, benzthiazolyl or benzimidazolyl; and W is $(C_1-C_6)$alkoxy optionally substituted with from one to five fluorine atoms.

(4) A compound as defined in paragraph 1, 2 or 3 above wherein: (a) $R^3$ is a group of the formula III and $R^9$ is benzhydryl; (b) $R^3$ is a group of the formula VII, $R^{12}$ is phenyl, each of $R^{13}$, $R^{14}$, $R^{15}$ and $R^{16}$ is hydrogen, m is zero and $X^4$ is —$(CH_2)_3$—; or (c) $R^3$ is a group of the formula IX, r is two and $R^{19}$ is benzhydryl.

(5) A compound of the formula Ia wherein: (a) $R^3$ is a group of the formula III wherein the substituents at positions "2" and "3" of the nitrogen containing ring are in the cis configuration, $R^9$ is benzhydryl and A is phenyl; or (b) $R^3$ is a group of the formula VII wherein $R^{12}$ and the substituent at position "3" of the nitrogen containing ring are in the cis configuration, A is phenyl, $R^2$ is phenyl, each of $R^2$, $R^{13}$, $R^{14}$, $R^{15}$ and $R^{16}$ is hydrogen, m is zero, W is methoxy or isopropoxy, $X^4$ is —$(CH_2)_3$— and R is thiazolyl, imidazolyl, pyrrolyl, oxazolyl or thiadiazolyl.

(6) A compound of the formula Ib wherein $R^3$ is a group of the formula IX wherein the substituents at positions "2" and "3" of the nitrogen containing ring are in the cis configuration, $R^{19}$ is benzhydryl, r is two and the fused bicyclic ring system to which W and the —$CH_2NR^2R^3$ sidechain are attached is benzisoxazolyl or benzthiazolyl.

(7) A compound of the formula Ib wherein $R^3$ is a group of the formula IX, $R^{19}$ is benzhydryl, the fused bicyclic ring system to which W and the —$CH_2NR^2R^3$ sidechain are attached is benzisoxazolyl, and W is methoxy.

(8) A compound of the formula Ib wherein $R^3$ is a group of the formula VII, $R^{12}$ is phenyl, each of $R^{13}$, R, $R^{15}$ and $R^{16}$ is hydrogen, m is zero, $X^4$ is —$(CH_2)_3$—, and the fused bicyclic ring system to which W and the —$CH_2NR^2R^3$ sidechain are attached is benzothiazolyl, benzoxazolyl or benzimidazolyl.

(9) A compound of the formula Ia wherein $R^3$ is a group of the formula VII, each of $R^{13}$, $R^{14}$, $R^{15}$ and $R^{16}$ is hydrogen, m is zero, X is —$(CH_2)_3$—, A is phenyl, W is methoxy, and R is selected from thiazolyl, imidazolyl, thiadiazolyl and isoxazolyl.

(10) A compound of the formula Ia or Ib that is selected from:

(2S, 3S)-3-[2-methoxy-5-(2-thiazolyl)benzyl]amino-2-phenylpiperidine;

(2S, 3S)-3-[5-(2-imidazolyl)-2-methoxybenzyl]amino-2-phenylpiperidine;

(2S, 3S)-3-[2-methoxy-5-(2-oxopyrrolidinyl)benzyl]amino-2 -phenylpiperidine;

(2S, 3S)-3-[2-methoxy-5-(4-methyl-2-thiazolyl)benzyl]-amino-2-phenylpiperidine;

(2S, 3S)-3-[2-methoxy-5-(1,2,3-thiadiazol-4-yl)benzyl]-amino-2-phenylpiperidine;

(2S, 3S)-(6-methoxy-2-methyl-benzothiazol-5-ylmethyl)-(2-phenylpiperidin-3-yl)amine;

(2S, 3S)-[5-(2,5-dimethyl-pyrrol-1-yl)-2-methoxybenzyl]-(2-phenylpiperidin-3-yl)amine;

(2S, 3S)-3-[2-methoxy-5-(5-oxazolyl)benzyl]amino-2-phenylpiperidine;

(2S, 3S)-(6-methoxy-2-methyl-benzoxazol-5-ylmethyl)-(2-phenyl-piperidin-3-yl)-amine; and (1SR, 2SR, 3SR, 4RS)-3-[6-methoxy-3-methylbenzisoxazol-5-yl]methylamino-2-benzhydrylazanorbornane.

(11) A compound of the formula Ic, wherein $R^3$ is a group of the formula II, III, VII or IX; $R^2$ is hydrogen; ring AA is phenyl or indolinyl; $W^1$ is $(C_1-C_3)$alkoxy optionally substituted with from one to three fluorine atoms; and $R^1$ is $S(O)_v$—$(C_1-C_{10})$alkyl wherein v is zero, one or two, $S(O)_v$-aryl wherein v is zero, one or two, —O-aryl,

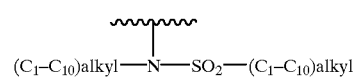

wherein one or both of the alkyl moieties may optionally be substituted with from one to three fluorine atoms, —$N(SO_2$—$(C_1-C_{10})$alkyl$)_2$ or

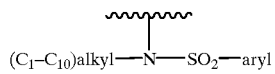(C$_1$–C$_{10}$)alkyl—N—SO$_2$—aryl wherein said aryl is phenyl or benzyl and may optionally be substituted with from one to three substituents independently selected from (C$_1$–C$_4$)alkyl, (C$_1$–C$_4$)alkoxy and halo.

(12) A compound as defined in paragraph 11 above, wherein R$^3$ is a group of the formula II, o is two, and each R$^6$ and R$^7$ is phenyl.

(13) A compound as defined in paragraph 11 above, wherein R$^3$ is a group of the formula VII, each of R$^{13}$, R$^{14}$, R$^{15}$ and R$^{16}$ is hydrogen, R$^{12}$ is phenyl, m is zero and X$^4$ is —(CH$_2$)$_3$—.

(14) A compound as defined in paragraph 11 above, wherein R$^3$ is a group of the formula IX, R$^{19}$ is benzhydryl and r is two.

(15) A compound as defined in paragraph 11 above, wherein R$^3$ is a group of the formula III, R$^8$ is other than hydrogen and R$^9$ is benzyhydryl.

(16) A compound to the formula Ic wherein the substituents at positions "2" and "3" of the nitrogen containing ring are in the cis configuration.

(17) A compound of the formula Ic wherein R$^3$ is a group of the formula II wherein the substituents at positions "2" and "3" of the nitrogen containing ring are in the cis configuration, o is two, each of R$^6$ and R$^7$ is phenyl and ring AA is phenyl or indolinyl.

(18) A compound of the formula Ic wherein R$^3$ is a group of the formula III wherein the substituents at positions "2" and "3" of the nitrogen containing ring are in the cis configuration, R$^1$ is other than hydrogen, R$^9$ is benzhydryl and ring AA is phenyl.

(19) A compound of the formula Ic wherein R$^3$ is a group of the formula VII wherein R$^{12}$ and the substituent at position "3" of the nitrogen containing ring are in the cis configuration, ring AA is phenyl, R$^{12}$ is phenyl, each of R$^2$, R$^{13}$, R$^{14}$, R$^{15}$ and R$^{16}$ is hydrogen, m is zero, X$^4$ is —(CH$_2$)$_2$— or —(CH$_2$)$_3$— and R$^1$ is selected from S(O)$_v$—(C$_1$–C$_{10}$)alkyl wherein v is zero, one or two, and

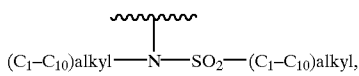(C$_1$–C$_{10}$)alkyl—N—SO$_2$—(C$_1$–C$_{10}$)alkyl, and di-(C$_1$–C$_6$)alkylamino.

(20) A compound as defined in paragraph 19 above, wherein X$^4$ is —(CH$_2$)$_2$— and W$^1$ is (C$_1$–C$_6$)alkoxy optionally substituted with from one to three fluorine atoms.

(21) A compound as defined in paragraph 19 above, wherein X$^4$ is —(CH$_2$)$_3$— and W$^1$ is (C$_1$–C$_6$)alkoxy optionally substituted with from one to three fluorine atoms.

(22) A compound of the formula Ic, wherein R$^3$ is a group of the formula IX wherein the substituents at positions "2" and "3" of the nitrogen containing ring are in the cis configuration, r is two and R$^{19}$ is benzhydryl.

(23) A compound as defined in paragraph 22 above, wherein ring AA is phenyl, W$^1$ is (C$_1$–C$_5$)alkoxy optionally substituted with from one to three fluorine atoms and R$^1$ is selected from —S(O)$_v$—(C$_1$–C$_{10}$)alkyl wherein v is zero, one or two, di-(C$_1$–C$_6$)alkylamino and

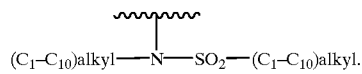(C$_1$–C$_{10}$)alkyl—N—SO$_2$—(C$_1$–C$_{10}$)alkyl.

(24) A compound as defined in paragraph 15 above, wherein ring AA is phenyl, W$^1$ is (C$_1$–C$_6$)alkoxy optionally substituted with from one to three fluorine atoms, and R$^1$ is selected from —S(O)$_v$—(C$_1$–C$_{10}$)alkyl wherein v is zero, one or two, and

(C$_1$–C$_{10}$)alkyl—N—SO$_2$—(C$_1$–C$_{10}$)alkyl.

(25) A compound as defined in paragraph 15 above, wherein ring AA is phenyl, W$^1$ is (C$_1$–C$_6$)alkoxy optionally substituted with from one to three fluorine atoms, and R$^1$ is selected from amino, (C$_1$–C$_6$)alkylamino or di-(C$_1$–C$_6$)alkylamino.

(26) A compound as defined in paragraph 12 above, wherein ring AA is phenyl, W$^1$ is (C$_1$–C$_6$)alkoxy optionally substituted with from one to three fluorine atoms, and R$^1$ is selected from —S(O)$_v$—(C$_1$—C$_{10}$)alkyl wherein v is zero, one or two, and

(C$_1$–C$_{10}$)alkyl—N—SO$_2$—(C$_1$–C$_{10}$)alkyl.

(27) A compound as defined in paragraph 12 above, wherein ring AA is phenyl, W$^1$ is (C$_1$–C$_6$)alkoxy optionally substituted with from one to three fluorine atoms, and R$^1$ is selected from amino, (C$_1$–C$_6$)alkylamino or di-(C$_1$–C$_6$)alkylamino.

(28) A compound as defined in paragraph 24 above, wherein W$^1$ is attached at the "2" position of ring AA and R$^1$ is attached at the "5" position of ring AA, relative to the point of attachment of the NR$^2$R$^3$ containing side chain.

(29) A compound as defined in paragraph 25 above, wherein W$^1$ is attached at the "2" position of ring AA and R$^1$ is attached at the "5" position of ring AA, relative to the point of attachment of the NR$^2$R$^3$ containing side chain.

(30) A compound as defined in paragraph 26 above, wherein W$^1$ is attached at the "2" position of ring AA and R$^1$ is attached at the "5" position of ring AA, relative to the point of attachment of the NR$^2$R$^3$ containing side chain.

(31) A compound as defined in paragraph 27 above, wherein W$^1$ is attached at the "2" position of ring AA and R$^1$ is attached at the "5" position of ring AA, relative to the point of attachment of the NR$^2$R$^3$ containing side chain.

(32) A compound as defined in paragraph 13 above, wherein ring AA is phenyl, W$^1$ is selected from isopropoxy, OCF$_3$, OCH$_3$, OCHF$_2$, and OCH$_2$CF$_3$, and R$^1$ is selected from —S(O)$_v$—(C$_1$–C$_{10}$)alkyl wherein v is zero, one or two, and (C$_1$–C$_{10}$)alkyl-N—SO$_2$—(C$_1$–C$_{10}$)alkyl.

(33) A compound selected from the group consisting of:
(2S, 3S)-N-(2-methoxy-5-methylsulfonylphenyl)-methyl-2-diphenylmethyl-1-azabicyclo[2.2.2]octan-3-amine;

(2S, 3S)-N-(2-methoxy-5-methylthiophenyl)methyl-2-diphenylmethyl-1-azabicyclo[2.2.2]octan-3-amine;

(2S, 3S)-N-(2-methoxy-5-dimethylaminophenyl)methyl-2-diphenylmethyl-1-azabicyclo[2.2.2]octan-3-amine; and (2S, 3S)-N-(5-trifluoroacetylamino-2-methoxyphenyl) methyl-2-diphenylmethyl-1-azabicyclo-[2.2.2]octan-3-amine.

(34) A compound of the formula Ic, wherein $R^3$ is a group of the formula VII, m is zero, each of $R^{13}$, $R^{15}$, $R^{16}$ and $R^{17}$ is hydrogen, $R^{12}$ is phenyl, $R^{14}$ is

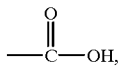

ring AA is phenyl, $W^1$ is $(C_1-C_3)$alkoxy and $R^1$ is selected from $(C_1-C_5)$alkyl, $-SCH_3$, $SO_2CH_3$, $SOCH_3$, $(C_1-C_6)$alkylamino and di-$(C_1-C_6)$alkyl-amino.

(35) A compound of the formula Ic, having the formula

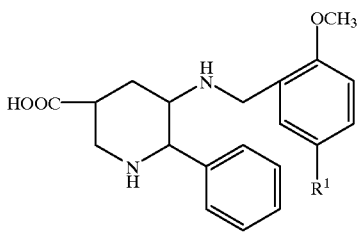

(36) A compound of the formula Id wherein $R^6_1$, $R^{10}$, $R^{11}$ and $R^{13}$ are phenyl, $R^8$ is hydrogen, $R^9$ is phenyl optionally substituted with chlorine, fluorine, $(C_1-C_6)$alkyl optionally substituted with from one to three fluorine atoms or $(C_1-C_6)$ alkoxy optionally substituted with from one to three fluorine atoms, m is 0 and n is 3 or 4.

(37) A compound of the formula Id that is selected from the group consisting of:
  (2S, 3S)-3-(5-tert-butyl-2-methoxybenzyl)amino-2-(3-trifluoromethoxyphenyl)piperidine;
  (2S, 3S)-3-(2-isopropoxy-5-trifluoromethoxybenzyl) amino-2-phenyl-piperidine;
  (2S, 3S)-3-(2-ethoxy-5-trifluoromethoxybenzyl)amino-2-phenyl-piperidine;
  (2S, 3S)-3-(2-methoxy-5-trifluoromethoxybenzyl)-amino-2-phenylpiperidine;
  (2S, 3S)-3 (-5-tert-butyl-2-trifluoromethoxybenzyl) amino-2-phenylpiperidine;
  2-(diphenylmethyl)-N-(2-methoxy-5-trifluoromethoxy-phenyl)methyl-1-azabicyclo[2.2.2]octan-3-amine;
  (2S, 3S)-3-[5-chloro-2-(2,2,2-trifluoroethoxy)-benzyl] amino-2-phenylpiperidine;
  (2S, 3S)-3-(5-tert-butyl-2-trif luoromethoxybenzyl) amino-2-phenylpiperidine;
  (2S, 3S)-3-(2-isopropoxy-5-trifluoromethoxybenzyl) amino-2-phenylpiperidine;
  (2S, 3S)-3-(2-difluoromethoxy-5-trifluoromethoxybenzyl)-amino-2-phenylpiperidine;
  (2S, 3S)-2-phenyl-3-[2-(2,2,2-trifluoroethoxybenzyl)-aminopiperidine; and
  (2S, 3S)-2-phenyl-3-(2-trifluoromethoxybenzyl)] aminopiperidine.

(38) A compound of the formula Id, wherein $R^3$ is a group of the formula II wherein o is two or three and each of $R^6$ and $R^7$ is phenyl or substituted phenyl.

(39) A compound of the formula Id, wherein $R^3$ is a group of the formula III, $R^8$ is hydrogen and $R^9$ is phenyl or substituted phenyl.

(40) A compound of the formula Id, wherein $R^3$ is a group of the formula IV wherein l is one or two and each of $R^{10}$ and $R^{11}$ is phenyl or substituted phenyl.

(41) A compound of the formula Id, wherein $R^3$ is a group of the formula V wherein n is zero or one and each of $R^{10}$ and $R^{11}$ is phenyl or substituted phenyl.

(42) A compound of the formula Id, wherein $R^3$ is a group of the formula VI wherein p is one and each of $R^{10}$ and $R^{11}$ are phenyl or substituted phenyl.

(43) A compound of the formula Id, wherein $R^3$ is a group of the formula VII wherein q is two, three or four, m is zero and $R^{12}$ is phenyl or substituted phenyl.

(44) A compound of the formula Id, wherein $R^3$ is a group of the formula VIII wherein y is zero, x is zero or one, z is three or four, m is zero and $R^{12}$ is phenyl or substituted phenyl.

(45) A compound of the formula Id wherein $R^3$ is a group of the formula VII, $R^6$, $R^{14}$, $R^{13}$ $R^{16}$ and $R^{15}$ are hydrogen, $R^{12}$ is phenyl, $X^1$ is 2-methoxy, $X^2$ and $X^3$ are independently selected from hydrogen, chlorine, fluorine, methyl, $(C_1-C_6)$ alkoxy and trifluoromethane, m is 0 and q is 3 or 4.

(46) A compound of the formula Id wherein $R^3$ is a group of the formula VII and said compound is selected from the group consisting of:
  cis-3-(2-chlorobenzylamino)-2-phenylpiperidine;
  cis-3-(2-trifluoromethylbenzylamino)-2-phenyl-piperidine;
  cis-3-(2-methoxybenzylamino)-2-(2-fluorophenyl)-piperidine;
  cis-3-(2-methoxybenzylamino)-2-(2-chlorophenyl)-piperidine;
  cis-3-(2-methoxybenzylamino)-2-(2-methylphenyl)-piperidine;
  cis-3-(2-methoxybenzylamino)-2-(3-methoxyphenyl)-piperidine;
  cis-3-(2-methoxybenzylamino)-2-(3-fluorophenyl)-piperidine;
  cis-3-(2-methoxybenzylamino)-2-(3-chlorophenyl)-piperidine;
  cis-3-(2-methoxybenzylamino)-2-phenylpiperidine;
  cis-3-(2-methoxybenzylamino)-2-(3-methylphenyl)-piperidine;
  cis-3-(2-methoxybenzylamino)-2-(4-fluorophenyl)-piperidine;
  cis-3-(2-methoxybenzylamino)-2-(3-thienyl)-piperidine;
  cis-3-(2-methoxybenzylamino)-2-phenylazacyclo-heptane;
  3-(2-methoxybenzylamino)-4-methyl-2-phenyl-piperidine;
  3-(2-methoxybenzyla,ino)-5-methyl-2-phenyl-piperidine;
  3-(2-methoxybenzylamino)-6-methyl-2-phenyl-piperidine;
  (2S, 3S)-3-(2-methoxybenzylamino)-2-phenylpiperidine;
  (2S, 3S)-1-(5-carboethoxypent-1-yl)-3-(2-methoxybenzyl-amino)-2-phenylpiperidine;
  (2S, 3S)-1-(6-hydroxy-hex-1-yl)-3-(2-methoxybenzyl-amino)-2-phenylpiperidine;
  (2S, 3S)-1-(4-hydroxy-4-phenylbut-1-yl)-3-(2-methoxy-benzylamino)-2-phenylpiperidine;
  (2S, 3S)-1-(4-oxo-4-phenylbut-1-yl)-3-(2-methoxybenzyl-amino)-2-phenylpiperidine;
  (2S, 3S)-1-(5,6-dihydroxyhex-1-yl)-3-(2-methoxybenzyl-amino)-2-phenylpiperidine;
  cis-3-(5-fluoro-2-methoxybenzylamino)-2-phenyl-piperidine;
  (2S, 3S)-1-[4-(4-fluorophenyl)-4-oxobut-1-yl]-3-(2-methoxybenzylamino)-2-phenylpiperidine;

(2S, 3S)-1-[4-[4-fluorophenyl)-4-hydroxybut-1-yl]-3-(2-methoxybenzylamino)-2-phenylpiperidine;
cis-3-(2-methoxy-5-methylbenzylamino)-2-phenyl-piperidine;
(2S, 3S)-1-(4-benzamidobut-1-yl)-3-(2-methoxybenzylamino)-2-phenylpiperidine;
cis-3-(2-methoxynaphth-1-ylmethylamino)-2-phenyl-piperidine;
(2S, 3S)-3-(2-methoxybenzylamino)-1-(5-N-methylcarboxamidopent-1-yl)-2-phenylpiperidine;
(2S, 3S)-1-(4-cyanobut-1-yl)-3-(2-methoxybenzylamino)-2-phenylpiperidine;
(2S, 3S)-1-[4-(2-naphthamido)but-1-yl]-3-(2-methoxybenzylamino)-2-phenylpiperidine;
(2S, 3S)-1-(5-benzamidopent-1-yl)-3-(2-methoxybenzylamino)-2-phenylpiperidine;
(2S, 3S)-1-(5-aminopent-1-yl)-3-(2-methoxybenzylamino)-2-phenylpiperidine;
(2S, 3S)-3-(5-chloro-2-methoxybenzylamino)-2-phenyl-piperidine;
(2S, 3S)-3-(2,5-dimethoxybenzylamino)-2-phenyl-piperidine;
cis-3-(3,5-difluoro-2-methoxybenzylamino)-2-phenyl-piperidine;
cis-3-(4, 5-difluoro-2-methoxybenzylamino)-2-phenyl-piperidine;
cis-3-(2, 5-dimethoxybenzylamino)-1-[4-(4-fluorophenyl)-4-oxobut-1-yl]-2-phenylpiperidine;
ois-3-(5-chloro-2-methoxybenzylamino)-1-(5,6-dihydroxyhex-1-yl)-2-phenylpiperidine;
cis-1-(5,6-dihydroxyhex-1-yl)-3-(2,5-dimethoxybenzylamino)-2-phenylpiperidine;
cis-2-phenyl-3-[-2(prop-2-yloxy)benzylamino]piperidine;
cis-3-(2,5-dimethoxybenzyl)amino-2-(3-methoxyphenyl)piperidine hydrochloride;
cis-3-(5-chloro-2-methoxybenzyl) amino-2-(3-methoxyphenyl)piperidine dihydrochloride;
cis-3-(5-chloro-2-methoxybenzyl) amino-2-(3-chlorophenyl)piperidine dihydrochloride;
3-(2-methoxybenzylamino)-2,4-diphenylpiperidine;
cis-3-(2-methoxybenzylamino)-2-phenylpyrrolidine;
(2S, 3S)-3-(5-ethyl-2-methoxybenzyl)amino-2-phenyl-piperidine;
(2S, 3S)-3-(5-n-butyl-2-methoxybenzyl)amino-2-phenyl-piperidine;
(2S, 3S)-3-(2-methoxy-5-n-propylbenzyl)amino-2-phenyl-piperidine;
(2S, 3S)-3-(5-isopropyl-2-methoxybenzyl)amino-2-phenyl-piperidine;
(2S, 3S)-3-(5-s-butyl-2-methoxybenzyl)amino-2-phenyl-piperidine;
(2S, 3S)-3-(5-t-butyl-2-methoxybenzyl)amino-2-phenyl-piperidine; and
(2S, 3S)-3-(2-methoxy-5-phenylbenzyl)amino-2-phenyl-piperidine.

(47) A compound of the formula Id, wherein R³ is a group of the formula II or III and said compound is selected from the group consisting of:
(2S, 3S)-N-(5-isopropyl-2-methoxyphenyl)methyl-2-diphenylmethyl-1-azabicyclo[2.2.2]octan-3-amine;
(2S, 3S)-N-(5-tert-butyl-2-methoxyphenyl)methyl-2-diphenylmethyl-1-azabicyclo[2.2.2]octan-3-amine;
(2S, 3S)-N-(5-methyl-2-methoxyphenyl)methyl-2-diphenyl-methyl-1-azabicyclo[2.2.2]octan-3-amine;
(2S, 3S)-N-(5-ethyl-2-methoxyphenyl)methyl-2-diphenyl-methyl-1-azabicyclo[2.2.2]octan-3-amine;
(2S, 3S)-N-(5-isopropyl-2-methoxyphenyl)methyl-2-diphenylmethyl-1-azabicyclo[2.2.2]octan-3-amine;
(2S, 3S)-N-(5-sec-butyl-2-methoxyphenyl)methyl-2-diphenylmethyl-1-azabicyclo[2.2.2]octan-3-amine; and
(2S, 3S)-N-(5-n-propyl-2-methoxyphenyl)methyl-2-diphenylmethyl-1-azabicyclo[2.2.2]octan-3-amine.

(47A) a compound of the formula Ie that is selected from the group consisting of:
2,4-dimethylthiazole-5-sulfonic acid[4-methoxy-3-((2S, 3S)-2-phenylpiperidin-3-ylaminomethyl)phenyl]-methylamide;
N-(4,5-dimethylthiazol-2-yl)-N-[4-methoxy-3-((2S, 3S)-2-phenylpiperidin-3-yl-aminomethyl)phenyl]-methanesulfonamide;
{5-[(4,5-dimethylthiazol-2-yl)methylamino]-2-methoxybenzyl}-((2S, 3S)-2-phenylpiperidin-3-yl) amine;
{5-(4,5-dimethylthiazol-2-ylamino)-2-methoxybenzyl}-((2S, 3S)-2-phenylpiperidin-3-ylamine;
4,5-dimethylthiazole-2-sulfonic acid methyl-[3-((2S, 3S)-2-phenylpiperidin-3-ylaminomethyl)-4-trifluoromethoxyphenyl]-amide;
2,4-dimethylthiazole-5-sulfonic acid [4-isopropoxy-3-((2S, 3S)-2-phenylpiperidin-3-ylaminomethyl)phenyl]-methylamide;
2,4-dimethylthiazole-5-sulfonic acid [4-isopropoxy-3-((2S, 3S)-2-phenylpiperidin-3-ylaminomethyl)phenyl]-isopropylamide;
2,4-dimethylthiazole-5-sulfonic acid [4-methoxy-3-((2S, 3S)-2-phenylpiperidin-3-ylaminomethyl)phenyl]-isopropylamide;
2,4-dimethylthiazole-5-sulfonic acid [4-methoxy-3-((2S, 3S)-2-phenylpiperidin-3-ylaminomethyl)phenyl]-isobutylamide; and
2,4-dimethylthiazole-5-sulfonic acid [4-isopropoxy-3-((2S, 3S)-2-phenylpiperidin-3-ylaminomethyl)phenyl]-isobutylamide.

This invention also relates to a method of treating or preventing a disorder selected from stroke, epilepsy, head trauma, spinal cord trauma, ischemic neuronal damage such as cerebral ischemic damage from stroke or vascular occlusion (e.g., during open heart surgery), excitotoxic neuronal damage (e.g., in stroke or epilepsy) and amyotrophic lateral sclerosis in a mammal, including a human, comprising administering to said mammal an amount of a compound having the formula

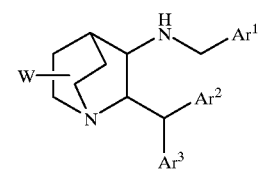

(X)

wherein W is Y or X(CH$_2$)$_n$;
Y is optionally substituted (C$_1$–C$_6$)alkyl, optionally substituted (C$_2$–C$_6$)alkenyl or optionally substituted (C$_3$–C$_8$)cycloalkyl;

X is optionally substituted ($C_1$–$C_6$)alkoxy, hydroxy, $CONR^1R^2$, $CO_2R^1$, $CHR^1OR^2$, $CHR^1NR^2R^3$, $COR^1$, $CONR^1OR^2$ or optionally substituted aryl, wherein said aryl is selected from phenyl, naphthyl, pyridyl, quinolyl, thienyl, furyl, phenoxyphenyl, oxazolyl, tetrazolyl, thiazolyl, imidazolyl and pyrazolyl; and n is an integer from zero to six;

$Ar^1$, $Ar^2$ and $Ar^3$ are each, independently, optionally substituted aryl, wherein said aryl is selected from phenyl, naphthyl, pyridyl, quinolyl, thienyl, furyl, phenoxyphenyl, oxazolyl, tetrazolyl, thiazolyl, imidazolyl and pyrazolyl;

and $R^1$, $R^2$ and $R^3$ are independently selected from hydrogen, optionally substituted ($C_1$–$C_6$)alkyl, optionally substituted ($C_1$–$C_6$)alkoxy, optionally substituted ($C_3$–$C_8$)cycloalkyl, optionally substituted aryl, wherein said aryl is selected from phenyl, naphthyl, pyridyl, quinolyl, thienyl, furyl, phenoxyphenyl, oxazolyl, tetrazolyl, thiazolyl, imidazolyl and pyrazolyl; and optionally substituted ($C_1$–$C_5$)heterocyclic groups, wherein said heterocyclic groups are selected from pyrrolidino, piperidino, morpholino, piperazinyl and thiamorpholino;

and wherein the substituents on the foregoing substituted alkyl, alkenyl, cycloalkyl and alkoxy groups are independently selected from halo, nitro, amino, ($C_1$–$C_4$)alkyl, ($C_1$–$C_4$)alkoxy, trifluoromethyl and trifluoromethoxy; and wherein the substituents on the foregoing substituted ($C_1$–$C_5$)heterocyclic groups are attached to a sulfur or nitrogen atom on the ring and are independently selected from oxygen, di-oxygen and ($C_1$–$C_4$)alkyl when attached to a ring sulfur atom, and are independently selected from oxygen and ($C_1$–$C_4$)alkyl when attached to a ring nitrogen atom;

and wherein the substituents on said substituted $Ar^1$ groups are independently selected from ($C_1$–$C_6$)alkyl optionally substituted with from one to three halo groups, ($C_1$–$C_6$)alkoxy optionally substituted with from one to three halo groups, ($C_1$–$C_6$)alkylsulfinyl, ($C_2$–$C_6$)alkenyl, ($C_{1-C6}$)alkylthio, ($C_1$–$C_6$)alkylsulfonyl, ($C_1$–$C_6$)alkylsulfonylamino, and di-($C_1$–$C_6$)alkylamino wherein one or both of the alkyl groups may be optionally substituted with a ($C_1$–$C_6$) alkylsulfonyl, or ($C_1$–$C_6$)alkylsulfinyl group;

and wherein the substituents on said substituted $Ar^2$ and $Ar^3$ groups are independently selected from ($C_1$–$C_4$) alkyl, ($C_1$–$C_4$)alkoxy, ($C_1$–$C_4$)alkylthio, ($C_1$–$C_4$) alkylsulfinyl, di-($C_1$–$C_4$)alkylamino, trifluoromethyl and trifluoromethoxy; with the proviso that when Y is unsubstituted or is substituted with ($C_1$–$C_4$)alkyl, it is attached to the 4- or 6-position of the quinuclidine ring;

or a pharmaceutically acceptable salt of such compound, that is effective in treating or preventing such disorder.

Preferred embodiments of this invention include methods of treating or preventing a disorder selected from stroke, epilepsy, head trauma, spinal cord trauma, ischemic neuronal damage such as cerebral ischemic damage from stroke or vascular occlusion (e.g., during open heart surgery), excitotoxic neuronal damage (e.g., in stroke or epilepsy) and amyotrophic lateral sclerosis in a mammal, including a human, that comprise administering to said mammal an amount of a compound as defined in paragraphs (48) through (54) below, or a pharmaceutically acceptable salt thereof, that is effective in treating or preventing such disorder.

(48) A compound of the formula X, wherein W is $X(CH_2)_n$.

(49) A compound of the formula X, wherein W is Y.

(50) A compound of the formula X, wherein $Ar^1$ is substituted aryl and W is Y.

(51) A compound of the formula X, wherein Ar$^1$ is mono-, di- or tri-substituted phenyl and W is Y.

(52) A compound of the formula X, wherein $Ar^1$ is phenyl disubstituted at the 2- and 5-positions and W is Y.

(53) A compound of the formula X, wherein $Ar^1$ is paramethoxyphenyl, each of $Ar^2$ and $Ar^3$ is phenyl and W is Y.

(54) A compound of the formula X that is selected from the group consisting of:

(3R, 4S, 5S, 6S)-N,N-diethyl-5-(5-isopropyl-2-methoxybenzylamino)-6-diphenylmethyl-1-azabicyclo[2.2.2]octane-3-carboxamide;

(3R, 4S, 5S, 6S)-N,N-diethyl-5-(2,5-dimethoxybenzylamino)-6-diphenylmethyl-1-azabicyclo[2.2.2]octane-3-carboxamide;

(3R, 4S, 5S, 6S)-5-(5-isopropyl-2-methoxybenzylamino)-6-diphenylmethyl-1-azabicyclo[2.2.2]octane-3-carboxylic acid;

(3R, 4S, 5S, 6S)-5-(2-methoxy-2-methylthiobenzylamino)-6-diphenylmethyl-1-azabicyclo[2.2.2]octane-3-carboxylic acid;

(3R, 4S, 5S, 6S)-5-(2,5-dimethoxybenzylamino)-6-diphenyl-methyl-1-azabicyclo-[2.2.2]octane-3-carboxylic acid;

(3R, 4S, 5S, 6S)-5-(2-methoxy-5-methylbenzylamino)-6-diphenylmethyl-1-azabicyclo[2.2.2]octane-3-carboxylic acid;

(3R, 4S, 5S, 6S)-5-(5-ethyl-2-methoxybenzylamino)-6-diphenylmethyl-1-azabicyclo[2.2.2]octane-3-carboxylic acid;

(3R, 4S, 5S, 6S)-5-(2-methoxyl-5-n-propylbenzylamino)-6-diphenylmethyl-1-azabicyclo[2.2.2]octane-3-carboxylic acid;

(3R, 4S, 5S, 6S)-5-(5-sec-butyl-2-methoxybenzylamino)-6-diphenylmethyl-1-azabicyclo[2.2.2]octane-3-carboxylic acid;

(3R, 4S, 5S, 6S)-5-(5-N-methyl-methanesulfonylamino-2-methoxy-benzylamino)-6-diphenylmethyl-1-azabicyclo[2.2.2]octane-3-carboxylic acid;

(3R, 4S, 5S, 6S)-5-(2-methoxy-5-methylsulfinylbenzylamino)-6-diphenylmethyl-1-azabicyclo[2.2.2]octane-3-carboxylic acid;

(3R, 4S, 5S, 6S)-5-(2-methoxy-5-trifluoromethoxybenzyl-amino)-6-diphenylmethyl-1-azabicyclo[2.2.2]octane-3-carboxylic acid;

(3R, 4S, 5S, 6S)-5-(2-methoxy-5-methylsulfonylbenzylamino)-6-diphenylmethyl-1-azabicyclo[2.2.2]octane-3-carboxylic acid;

(3R, 4S, 5S, 6S)-5-(5-dimethylamino-2-methoxybenzylamino)-6-diphenylmethyl-1-azabicyclo[2.2.2]octane-3-carboxylic acid;

(3R, 4S, 5S, 6S)-5-(5-isopropyl-2-methoxybenzylamino)-6-diphenylmethyl-1-azabicyclo[2.2.2]octane-2-carboxylic acid;

(3R, 4S, 5S, 6S)-5-(2-methoxy-5-methylthiobenzylamino)-6-diphenylmethyl-1-azabicyclo[2.2.2]octane-2-carboxylic acid;

(3R, 4S, 5S, 6S)-5-(2,5-dimethoxybenzylamino)-6-diphenylmethyl-1-azabicyclo[2.2.2]octane-2-carboxylic acid;

(3R, 4S, 5S, 6S)-5-(2-methoxy-5-methylbenzylamino)-6-diphenylmethyl-1-azabicyclo[2.2.2]octane-2-carboxylic acid;

(3R, 4S, 5S, 6S)-5-(5-ethyl-2-methoxybenzylamino)-6-diphenylmethyl-1-azabicyclo[2.2.2]octane-2-carboxylic acid;

(3R, 4S, 5S, 6S)-5-(2-methoxyl-5-n-propylbenzylamino)-6-diphenylmethyl-1-azabicyclo[2.2.2]octane-2-carboxylic acid;

(3R, 4S, 5S, 6S)-5-(5-sec-butyl-2-methoxybenzylamino)-6-diphenylmethyl-1-azabicyclo[2.2.2]octane-2-carboxylic acid;

(3R, 4s, 5S, 6S)-5-(5-N-methylmethanesulfonylamino-2-methoxybenzyl-amino)-6-diphenylmethyl-1-azabicyclo[2.2.2]octane-2-carboxylic acid;

(3R, 4S, 5S, 6S)-5-(2-methoxy-5-methylsulfinylbenzyl-amino)-6-diphenylmethyl-1-azabicyclo[2.2.2]octane-2-carboxylic acid;

(3R, 4S, 5S, 6S)-5-(2-methoxy-5-trifluoromethoxybenzyl-amino)-6-diphenylmethyl-1-azabicyclo[2.2.2]octane-2-carboxylic acid;

(3R, 4S, 5S, 6S)-5-(2-methoxy-5-methylsulfonylbenzyl-amino)-6-diphenylmethyl-1-azabicyclo[2.2.2]octane-2-carboxylic acid; and (3R, 4S, 5S, 6S)-5-(5-dimethylamino-2-methoxybenzylamino)-6-diphenylmethyl-1-azabicyclo[2.2.2]octane-2-carboxylic acid.

This invention also relates to a method of treating or preventing a disorder selected from stroke, epilepsy, head trauma, spinal cord trauma, ischemic neuronal damage such as cerebral ischemic damage from stroke or vascular occlusion (e.q;, during open heart surgery), excitotoxic neuronal damage (e.g., in stroke or epilepsy) and amyotrophic lateral sclerosis in a mammal, including a human, comprising administering to said mammal an amount of a compound having the formula

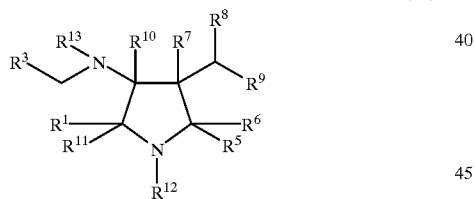

(XI)

wherein $R^1$ is selected from hydrogen, $(C_1-C_6)$ straight or branched alkyl, $(C_3-C_7)$cycloalkyl wherein one of the carbon atoms may optionally be replaced by nitrogen, oxygen or sulfur; aryl selected from phenyl, biphenyl, indanyl and naphthyl; heteroaryl selected from thienyl, furyl, pyridyl, thiazolyl, isothiazolyl, oxazolyl, isoxazolyl, triazolyl, tetrazolyl and quinolyl; phenyl $(C_2-C_6)$alkyl, benzhydryl and benzyl, wherein each of said aryl and heteroaryl groups and the phenyl moieties of said benzyl, phenyl $(C_2-C_6)$alkyl and benzhydryl may optionally be substituted with one or more substituents independently selected from halo, nitro, $(C_1-C_6)$ alkyl optionally substituted with from one to three fluorine atoms, $(_1-C_6)$alkoxy, amino, trihaloalkxy (e.g., trifluoromethoxy),

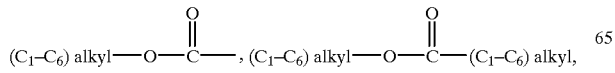

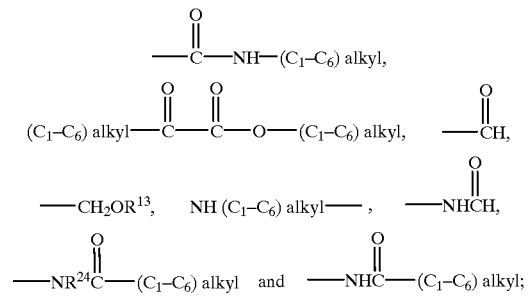

and wherein one of the phenyl moieties of said benzhydryl may optionally be replaced by naphthyl, thienyl, furyl or pyridyl;

$R^3$ is aryl selected from phenyl and naphthyl; heteroaryl selected from indanyl, thienyl, furyl, pyridyl, thiazolyl, isothiazolyl, oxazolyl, isoxazolyl, triazolyl, tetrazolyl and quinolyl; and cycloalkyl having 3 to 7 carbon atoms wherein one of said carbon atoms may optionally be replaced by nitrogen, oxygen or sulfur; wherein each of said aryl and heteroaryl groups may optionally be substituted with one or more substituents, and said $(C_3-C_7)$cycloalkyl may optionally be substituted with one or two substituents, each of said substituents being independently selected from halo, nitro, $(C_1-C_6)$alkyl optionally substituted with from one to three fluorine atoms, $(C_1-C_6)$alkoxy optionally substituted with from one to three fluorine atoms, amino, phenyl, trihaloalkoxy (e.g., trifluoromethoxy), $(C_1-C_6)$alkylamino,

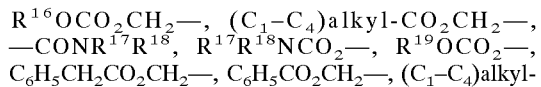

one of $R^5$ and $R^6$ is hydrogen and the other is selected from hydroxymethyl, hydrogen, $(C_1-C_3)$alkyl, $(C_1-C_8)$ acyloxy-$(C_1-C_3)$alkyl, $(C_1-C_8)$alkoxymethyl and benzyloxymethyl;

$R^7$ and $R^8$ are independently selected from hydrogen, $(C_1-C_3)$alkyl and phenyl;

$R^9$ is selected from methyl, hydroxymethyl,

$R^{16}OCO_2CH_2-$, $(C_1-C_4)$alkyl-$CO_2CH_2-$, $-CONR^{17}R^{18}$, $R^{17}R^{18}NCO_2-$, $R^{19}OCO_2-$, $C_6H_5CH_2CO_2CH_2-$, $C_6H_5CO_2CH_2-$, $(C_1-C_4)$alkyl- CH(OH)—, $C_6H_5CH(OH)$—, $C_6H_5CH_2CH(OH)$—, $CH_2$halo, $R^{20}SO_2OCH_2$, —$CO_2R^{16}$ and $R^{21}CO_2$—;

$R^{10}$ and $R^{11}$ are independently selected from hydrogen, $(C_1-C_3)$alkyl and phenyl;

$R^{12}$ is hydrogen, benzyl or a group of the formula

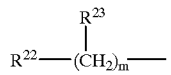

wherein m is an integer from zero to twelve, and any one of the carbon-carbon single bonds of $(CH_2)_m$, wherein both carbon atoms of such bond are bonded to each other and to another carbon atom in the $(CH_2)_m$ chain, may optionally be replaced by a carbon-carbon double or triple bond, and any one of the carbon atoms of $(CH_2)_m$ may optionally be substituted with $R^{23}$;

$R^{13}$, $R^{14}$, $R^{15}$, $R^{16}$, $R^{17}$, $R^{18}$, $R^{19}$, $R^{20}$, $R^{21}$ and $R^{24}$ are independently selected from hydrogen, $(C_1-C_3)$alkyl and phenyl;

$R^{22}$ and $R^{23}$ are independently selected from hydrogen, ydroxy, halo, amino, carboxy, carboxy$(C_1-C_6)$alkyl, $(C_1-C_6)$alkylamino, di-$(C_1-C_6)$alkylamino, $(C_1-C_6)$alkoxy, $(C_1-C_6)$—

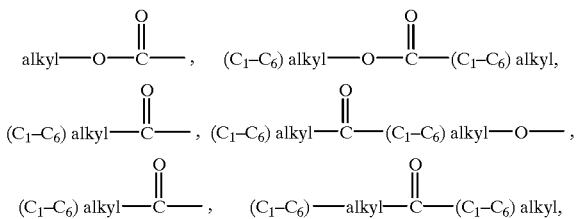

$(C_1-C_6)$ straight or branched alkyl, $(C_3-C_7)$cycloalkyl wherein one of the carbon atoms may optionally be replaced by nitrogen, oxygen or sulfur; aryl selected from phenyl and naphthyl; heteroaryl selected from indanyl, thienyl, furyl, pyridyl, thiazolyl, isothiazolyl, oxazolyl, isoxazolyl, triazolyl, tetrazolyl and quinolyl; phenyl-$(C_2-C_6)$alkyl, benzhydryl and benzyl, wherein each of said aryl and heteroaryl groups and the phenyl moieties of said benzyl, phenyl-$(C_2-C_6)$alkyl and benzhydryl may optionally be substituted with one or two substituents independently selected from halo, nitro, $(C_1-C_6)$alkyl optionally substituted with from one to three fluorine atoms, $(C_1-C_6)$alkoxy optionally substituted with from one to three fluorine atoms, trifluoromethyl, amino, $(C_1-C_6)$-alkylamino,

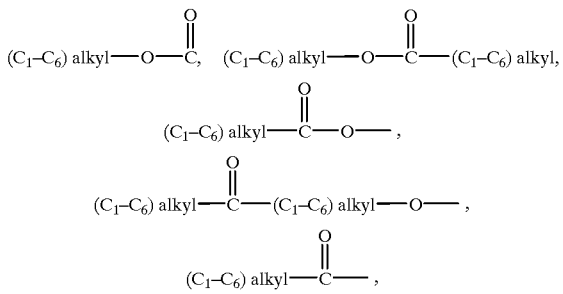

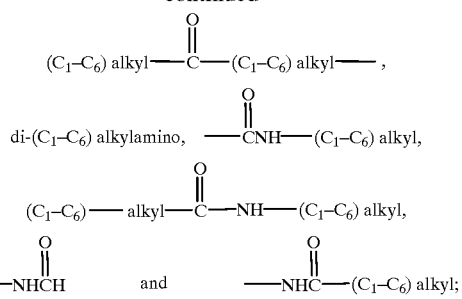

and wherein one of the phenyl moieties of said benzhydryl may optionally be replaced by naphthyl, thienyl, furyl or pyridyl;

or $R^9$, together with the carbon to which it is attached, the nitrogen of the pyrrolidine ring, the carbon to which $R^7$ is attached and the carbon to which $R^5$ and $R^6$ are attached form a second pyrrolidine ring; with the proviso that when $R^9$, together with the carbon to which it is attached, the nitrogen of the pyrrolidine ring, the carbon to which $R^7$ is attached and the carbon to which $R^5$ and $R^6$ are attached, form a second pyrrolidine ring (thus forming a bicyclic structure containing a bridgehead nitrogen), either $R^{12}$ is absent or $R^{12}$ is present and the nitrogen of the second pyrrolidine ring is positively charged; or a pharmaceutically acceptable salt of such compound, that is effective in treating or preventing such disorder.

Compounds of the formula XI that contain two pyrrolidine rings may be represented by one of the following two structures, depending on whether $R^{12}$ is present or absent.

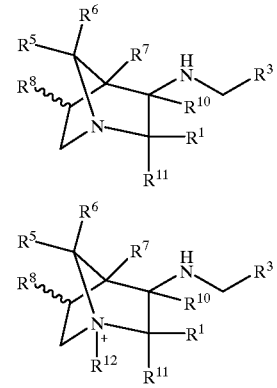

Preferred embodiments of this invention include methods of treating or preventing a disorder selected from stroke, epilepsy, head trauma, spinal cord trauma, ischemic neuronal damage such as cerebral ischemic damage from stroke or vascular occlusion (e.g., during open heart surgery), excitotoxic neuronal damage (e.g., in stroke or epilepsy) and amyotrophic lateral sclerosis in a mammal, including a human, that comprise administering to said mammal an amount of a compound as defined in paragraphs (55) through (59) below, or a pharmaceutically acceptable salt thereof, that is effective in treating or preventing such disorder.

(55) A compound of the formula XI wherein $R^1$ is benzhydryl.

(56) A compound of the formula XI wherein $R^1$ is diphenylmethyl, $R^3$ is aryl selected from phenyl or indanyl wherein each of said aryl groups may be optionally substituted with one, two or three substituents, each of $R^5$, $R^6$, $R^7$, $R^8$, $R^{10}$, and $R^{11}$ is hydrogen, $R^9$ is selected from hydroxymethyl, methoxymethyl, —$CO_2R^{16}$, —$CONR^{17}R^{18}$, $R^{14}R^{15}NCO_2CH_2$—, $R^{16}OCO_2CH_2$—, $(C_1–C_4)$alkyl-$CO_2CH_2$—, $C_6H_5CH_2CO_2CH_2$—, —$(CH_2$halo and $R^{20}SO_2OCH_2$—, and $R^{12}$ is hydrogen or benzyl.

(57) A compound of the formula XI wherein $R^1$ is phenyl, $R^3$ is aryl selected from phenyl or indanyl wherein each of said aryl groups may be optionally substituted with one, two or three substiuents, each of $R^5$, $R^6$, $R^7$, $R^8$, $R^{10}$, and $R^{11}$ is hydrogen, $R^9$ is selected from hydroxymethyl, methoxymethyl, —$CO_2R^{18}$, —$CONR^{17}R^{18}$, $R^{14}R^{15}NCO_2CH_2CH_2$—, $R^{16}OCO_2CH_2$—, $(C_1–C_4)$alkyl-$CO_2CH_2$—, —$CH_2$halo, $R^{20}SO_2OCH$—, and $R^{12}$ is hydrogen or benzyl.

(58) A compound of the formula XI wherein $R^1$ is diphenylmethyl, $R^3$ is aryl selected from phenyl or indanyl wherein each of said aryl groups may be optionally substituted with one, two or three substituents, each of $R^5$, $R^6$, $R^7$, $R^8$, $R^{10}$, $R^{11}$ and $R^{13}$ is hydrogen, and wherein $R^9$, together with the carbon to which it is attached, the nitrogen of the pyrrolidine ring, the carbon to which $R^7$ is attached and the carbon to which $R^5$ and $R^6$ are attached, form a second pyrrolidine ring (thus forming a bicyclic structure containing a bridgehead nitrogen).

(59) A compound of the formula XI that is selected from the group consisting of:

(2S, 3S, 4R)-2-diphenylmethyl-3-[(2-methoxy-4,5-dimethylphenyl)methylamino]-4-(2-hydroxyethyl)pyrrolidine;

(2SR, 3SR, 4RS)-2-diphenylmethyl-3-[(2-methoxy-4,5-dimethylphenyl)methylamino]-4-(2-hydroxyethyl)pyrrolidine;

(2SR, 3SR, 4RS)-2-diphenylmethyl-3-[(2-methoxy-5-(methylethyl)phenyl)methylamino]-4-(carbomethoxymethyl)-pyrrolidine;

(2SR, 3SR, 4RS)-2-diphenylmethyl-3-[(2-methoxy-5-(methylethyl)phenyl)methylamino]-4-(carboxymethyl)-pyrrolidine;

(2SR, 3SR, 4RS)-2-diphenylmethyl-3-[(2-methoxy-5-(methylethyl)phenyl)methylamino]-4-(2-dimethylamino-carbamoylethyl)pyrrolidine;

(2SR, 3SR, 4RS)-2-diphenylmethyl-3-((2-trifluoromethoxyphenyl)methylamino]-4-(2-hydroxyethyl)-pyrrolidine;

(2S, 3S, 4R)-2-diphenylmethyl-3-[(2-methoxy-5-(1,1-dimethylethyl)phenyl)methylaminoj-4-(2-hydroxyethyl)-pyrrolidine;

(2SR, 3SR, 4RS)-2-diphenylmethyl-3-((2-methoxy-5-(1,1-dimethylethyl)phenyl)methylamino]-4-(2-methoxyethyl)-pyrrolidine;

(2S, 3S, 4R)-2-diphenylmethyl-3-((2-methoxy-5-methylethyl)phenyl)methylamino]-4-(2-hydroxyethyl)-pyrrolidine;

(2SR, 3SR, 4RS)-2-diphenylmethyl-3-[(2-methoxy-5-methylethyl)phenyl)methylamino]-4-(2-methoxyethyl)-pyrrolidine;

(2SR, 3SR, 4RS)-2-diphenylmethyl-3-[(2-methyl-5-(1,1-dimethylethyl)phenyl)methylamino]-4-(2-hydroxyethyl)-pyrrolidine;

(1SR, 2SR, 3SR, 4RS)-1-aza-2-diphenylmethyl-3-[(2-methoxy-4,5-dimethylphenyl)-methylamino]-bicyclo[2.2.1]-heptane;

(1SR, 2SR, 3SR, 4RS)-1-aza-2-diphenylmethyl-3-[(2-methoxyphenyl)methylamino]bicyclo[2.2.1]heptane;

(1SR, 2SR, 3SR, 4RS)-1-aza-2-diphenylmethyl-3-[(2-methoxy-5-(1,1-dimethylethyl)phenyl)methylamino]bicyclo-[2.2.1]heptane;

(1SR, 2SR, 3SR, 4RS)-1-aza-2-diphenylmethyl-3-((2-methoxy-5-trifluoromethoxyphenyl)methylamino)bicyclo-[2.2.1]heptane;

(1SR, 2SR, 3SR, 4RS)-1-aza-2-diphenylmethyl-3-[(2-methoxy-5-(1-methylethyl)phenyl)methylamino]bicyclo-[2.2.1]heptane;

(1SR, 2SR, 3SR, 4RS)-1-aza-2-diphenylmethyl-3-[(2-methoxy-5-propylphenyl)methylamino]bicyclo[2.2.1]heptane;

(1SR, 2SR, 3SR, 4RS)-1-aza-2-diphenylmethyl-3-[(2-methoxy-5-(1-methylpropyl)phenyl)methylamino]bicyclo-[2.2.1]heptane;

(1SR, 2SR, 3SR, 4RS)-1-aza-2-phenyl-3-[(2-methoxyphenyl)methylamino]bicyclo[2.2.1]heptane;

(1SR, 2SR, 3RS, 4RS)-1-aza-2-phenyl-3-[(2-methoxy-5-trifluoromethoxyphenyl)methylamino]bicyclo[2.2.1]heptane;

(2SR, 3SR, 4RS)-N-1-phenylmethyl-2-diphenylmethyl-3-[(2-methoxyphenyl)methylamino]-4-(2-hydroxyethyl)-pyrrolidine;

(2SR, 3SR, 4RS)-2-diphenylmethyl-3-[(2-methoxyphenyl)methylamino]-4-(2-hydroxyethyl)pyrrolidine;

(2SR, 3SR, 4RS)-2-diphenylmethyl-3-[(2-methoxy-5-(1,1-dimethylethyl)phenyl)methylamino]-4-(2-hydroxyethyl)-pyrrolidine;

(2SR, 3SR, 4RS)-2-diphenylmethyl-3-[(2-methoxy-5-trifluoromethoxyphenyl)methylamino]-4-(2-hydroxyethyl)-pyrrolidine;

(2SR, 3SR, 4RS)-2-diphenylmethyl-3-[(2-methoxy-5-(1-methylethyl)phenyl)methylamino]-4-(2-hydroxyethyl)-pyrrolidine;

(2SR, 3SR, 4RS)-2-diphenylmethyl-3-[(2-methoxy-5-propylphenyl)methylamino]-4-(2-hydroxyethyl)pyrrolidine;

(2SR, 3SR, 4RS)-2-diphenylmethyl-3-[(2-methoxy-5-(1-methyl-1-propyl)phenyl)methylamino]-4-(2-hydroxyethyl)pyrrolidine;

(2SR, 3SR, 4RS)-2-diphenylmethyl-3-[(2-trifluoromethoxy-5-(i,l-dimethylethyl)phenyl)methylamino]-4-(2-hydroxyethyl)pyrrolidine;

(2SR, 3SR, 4RS)-2-diphenylmethyl-3-[(2-methoxy-5-chlorophenyl)methylamino]-4-(2-hydroxyethyl)pyrrolidine;

(2SR, 3SR, 4RS)-2-phenyl-3-[(2-methoxyphenyl)methylamino]-4-(2-hydroxyethyl)pyrrolidine;

(2SR, 3SR, 4RS)-2-phenyl-3-[(2-methoxy-5-(1,1-dimethylethyl)phenyl)methylamino]-4-(2-hydroxyethyl)pyrrolidine; and (2SR, 3SR, 4RS)-2-phenyl-3-[(2-methoxy-5-trifluoromethoxyphenyl)methylamino]-4-(2-hydroxyethyl)pyrrolidine.

This invention also relates to a method of treating or preventing a disorder selected from stroke, epilepsy, head trauma, spinal cord trauma, ischemic neuronal damage such as cerebral ischemic damage from stroke or vascular occlusion (e.g., during open heart surgery), excitotoxic neuronal damage (etg., in stroke or epilepsy) and amyotrophic lateral sclerosis in a mammal, including a human, comprising administering to said mammal an amount of a compound of the formula

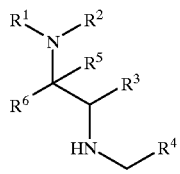

wherein $R^1$ is hydrogen, $(C_1-C_8)$alkyl, a saturated $(C_6-C_{10})$ carbocyclic ring system containing two fused rings, a saturated $(c_6-C_{10})$carbocyclic bridged ring system containing two rings, or benzyl wherein the phenyl moiety of said benzyl may optionally be substituted with one or more substituents independently selected from halo, $(C_1-C_6)$alkyl optionally substituted with from one to three fluorine atoms and $(C_1-C_8)$alkoxy optionally substituted with from one to three fluorine atoms;

$R^2$ is hydrogen, benzyl or a group of the formula

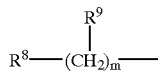

wherein m is an integer from zero to twelve, and any one of the carbon-carbon single bonds of $(CH_2)_m$, wherein both carbon atoms of such bond are bonded to each other and to another carbon atom of the $(CH_2)_m$ chain, may optionally be replaced by a carbon-carbon double or triple bond, and any one of the carbon atoms of $(CH_2)_m$ may optionally be substituted with $R^9$;

$R^8$ and $R^9$ are independently selected from hydrogen, hydroxy, halo, amino, carboxy, carboxy$(C_1-C_6)$alkyl, $((C_1-C_6)$alkylamino, di-$(C_1-C_6)$alkylamino, $(C_1-C_6)$ alkoxy,

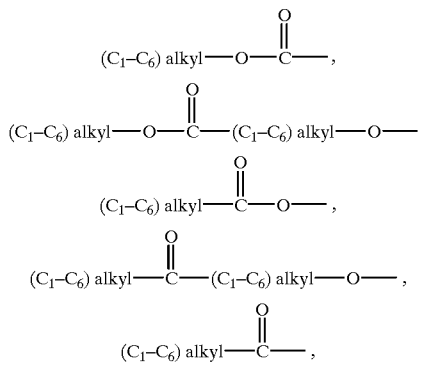

$(C_1-C_6)$ straight or branched alkyl, $(C_3-C_7)$ cycloalkyl wherein one of the carbon atoms may optionally be replaced by nitrogen, oxygen or sulfur; aryl selected from phenyl and naphthyl; heteroaryl selected from indanyl, thienyl, furyl, pyridyl, thiazolyl, isothiazolyl, oxazolyl, isoxazolyl, triazolyl, tetrazolyl and quinolyl; phenyl-$(C_2-C_6)$alkyl, benzhydryl and benzyl, wherein each of said aryl and heteroaryl groups and the phenyl moieties of said benzyl, phenyl-$(C_2-C_6)$alkyl and benzhydryl may optionally be substituted with one or two substituents independently selected from halo, nitro, $(C_1-C_6)$alkyl optionally substituted with from one to three fluorine atoms, $(C_1-C_6)$alkoxy optionally substituted with from one to three fluorine atoms, trifluoromethyl, amino, $(C_1-C_6)$-alkylamino,

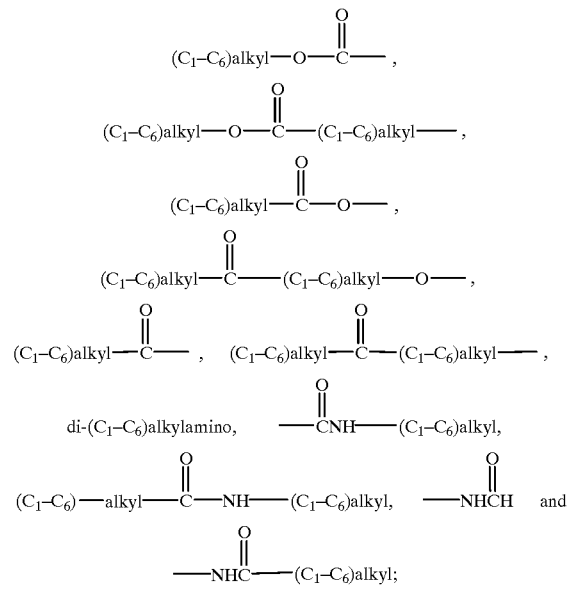

and wherein one of the phenyl moieties of said benzhydryl may optionally be replaced by naphthyl, thienyl, furyl or pyridyl;

or $R^1$ and $R^2$, together with the nitrogen to which they are attached, form a saturated or unsaturated monocyclic ring containing from three to eight carbon atoms, a fused bicyclic ring containing from six to ten carbon atoms, or a saturated bridged ring system containing from six to ten carbon atoms;

$R^4$ is aryl selected from phenyl and naphthyl; heteroaryl selected from indanyl, thienyl, furyl, pyridyl, thiazolyl, isothiazolyl, oxazolyl, isoxazolyl, triazolyl, tetrazolyl and quinolyl; and cycloalkyl having from three to seven carbon atoms wherein one of said carbon atoms may optionally be replaced by nitrogen, oxygen or sulfur; wherein each of said aryl and heteroaryl groups may optionally be substituted with one or more substituents, and said $(C_3-C_7)$ cycloalkyl may optionally be substituted with one, two or three substituents, each of said substituents being independently selected from halo, nitro, $(C_1-C_6)$alkyl optionally substituted with from one to three fluorine atoms, $(C_1-C_6)$alkoxy optionally substituted with from one to three fluorine atoms, phenyl, amino, $(C_1-C_8)$alkylamino,

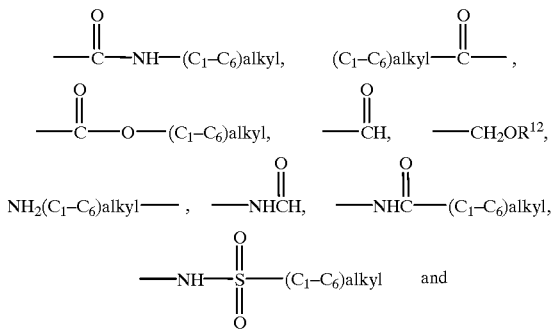

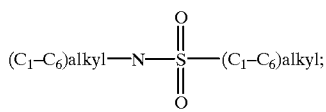

$R^3$ is hydrogen, $(C_3-C_8)$cycloalkyl, $(C_1-C_6)$ straight or branched alkyl or phenyl optionally substituted with one or more substituents independently selected from halo, $(C_1-C_6)$alkyl optionally substituted with from one to three fluorine atoms, and $(C_1-C_6)$alkoxy optionally substituted with from one to three fluorine atoms;

$R^5$ is hydrogen, $(C_1-C_6)$alkyl, or phenyl optionally substituted with one or more substituents independently selected from halo, $(C_1-C_6)$alkyl optionally substituted with from one to three fluorine atoms and $(C_1-C_6)$alkoxy optionally substituted with from one to three fluorine atoms;

$R^6$ is selected from hydrogen, $(C_1-C_6)$ straight or branched alkyl, $(C_1-C_7)$cycloalkyl wherein one of the carbon atoms may optionally be replaced by nitrogen, oxygen or sulfur; aryl selected from phenyl, biphenyl, indanyl and naphthyl; heteroaryl selected from thienyl, furyl, thiazolyl, isothiazolyl, oxazolyl, isoxazolyl, triazolyl, tetrazolyl and quinolyl; phenyl $(C_2-C_6)$alkyl, benzhydryl and benzyl, wherein each of said aryl and heteroaryl groups and the phenyl moieties of said benzyl, phenyl $(C_2-C_6)$alkyl and benzhydryl may optionally be substituted with one or more substituents independently selected from halo, nitro, $(C_1-C_6)$alkyl optionally substituted with from one to three fluorine atoms, $(C_1-C_6)$alkoxy, trifluoromethyl, amino, trihaloalkoxy (e.g. ,trif luoromethoxy),

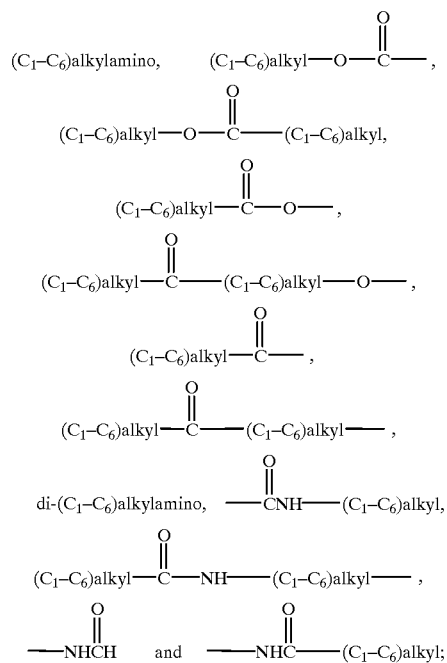

and wherein one of the phenyl moieties of said benzhydryl may optionally be replaced by naphthyl, thienyl, furyl or pyridyl; and $R^{12}$ is hydrogen, $(C_1-C_3)$alkyl or phenyl;

or a pharmaceutically acceptable salt of such compound, that is effective in treating or preventing such disorder.

Preferred embodiments of this invention include methods of treating or preventing a disorder selected from stroke, epilepsy, head trauma, spinal cord trauma, ischemic neuronal damage such as cerebral ischemic damage from stroke or vascular occlusion (e.g., during open heart surgery), excitotoxic neuronal damage (e.g., in stroke or epilepsy) and amyotrophic lateral sclerosis in a mammal, including a human, that comprise administering to said mammal an amount of a compound as defined in paragraphs (60) through (62) below, or a pharmaceutically acceptable salt thereof, that is effective in treating or preventing such disorder.

(60) A compound of the formula XII wherein $R^2$ is hydrogen, or $R^2$ and $R^1$, together with the nitrogen to which they are attached, form a monocyclic ring containing five to seven carbon atoms; $R^3$ is hydrogen, methyl or phenyl; $R^5$ is hydrogen; $R^4$ is phenyl or indanyl, wherein said phenyl or indanyl may optionally be substituted with from one to three substituents independently selected from halo, nitro, $(C_1-C_6)$alkyl optionally substituted with from one to three fluorine atoms, $(C_1-C_6)$alkoxy, trihaloalkoxy (e.g., trifluoromethoxy), $(C_1-C_6)$alkylamino, —C(O)NH—$(C_1-C_6)$alkyl, $(C_1-C_6)$alkyl-C(O)—, —C(O)—O—$(C_1-C_6)$alkyl, —C(O)H, —CH$_2$OR$^{12}$, —NH$(C_1-C_6)$alkyl, —NHC(O)H, —NHC(O)—$(C_1-C_6)$alkyl, —NHSO$_2$$(C_1-C_6)$alkyl and $(C_1-C_6)$alkyl-N—SO$_2$—$(C_1-C_6)$alkyl; and $R^6$ is phenyl.

(61) A compound of the formula XII wherein $R^1$ is alkyl, $R^6$ is unsubstituted phenyl, $R^4$ is a monosubstituted or disubstituted aryl group that is substituted at the C-2 position with an alkoxy group or substituted at the C-5 position with an alkyl, alkoxy or trihaloalkoxy group, or substituted in such manner at both C-2 and C-5 positions (i.e., with an alkoxy group at the C-2 position and an alkyl, alkoxy or trihaloalkoxy group at the C-5 position), and each of $R^2$, $R^3$ and $R^5$ is hydrogen.

(62) A compound of the formula XII that is selected from the group consisting of:

1-N-cyclohexyl-1-phenyl-2-N'-[(2-methoxyphenyl)methyl]-1,2-ethanediamine;

1-N-cyclohexyl-1-phenyl-2-N'-[(2-methoxy-5-trifluoromethoxyphenyl)methyl]-1,2-ethanediamine;

1-N-pyrrolidyl-1-phenyl-2-N'-[(2-methoxyphenyl)methyl]-1,2-ethanediamine;

1-N-methyl-1-phenyl-2-N'-[(2-nethoxyphenyl)methyl]-1,2-ethanediamine;

1-N-cyclopentyl-1-phenyl-2-N'-[(2-methoxyphenyl)methyl]-1,2-ethanediamine;

1-N-propyl-1-phenyl-2-N'-[(2-methoxyphenyl)methyl]-1,2-ethanediamine;

1-N-phenylmethyl-1-phenyl-2-N'-[(2-methoxyphenyl)methyl]-1,2-ethanediamine;

1-N-cyclooctyl-1-phenyl-2-N'-[(2-methoxyphenyl)methyl]-1,2-ethanediamine;

1-N-cyclobutyl-1-phenyl-2-N'-[(2-methoxyphenyl)methyl]-1,2-ethanediamine;

1-N-(2-adamantyl)-1-phenyl-2-N'-[(2-methoxyphenyl)methyl]-1,2-ethanediamine;

1-N-(1,1-dimethylethyl)-1-phenyl-2-N'-[(2-methoxyphenyl)methyl]-1,2-ethanediamine;

1-N-cyclopropyl-1-phenyl-2-N'-[(2-methoxyphenyl)methyl]-1,2-ethanediamine;

1-N-isopropyl-1-phenyl-2-N'-[(2-methoxyphenyl)methyl]-1,2-ethanediamine;

1-N-(1-phenylethyl)-1-phenyl-2-N'-[(2-methoxy-phenyl)methyl]-1,2-ethanediamine;

1-N-(2-norbornyl)-1-phenyl-2-N'-[(2-methoxyphenyl) methyl]-1,2-ethanediamine;

1-N-cyclohexyl-1-phenyl-2-N'-[(2-methoxy-5-tert-butylphenyl)methyl]-1,2-ethanediamine;

1-N-cyclohexyl-1-phenyl-2-N'-[(2-methoxy-5-isopropylphenyl)methyl]-1,2-ethanediamine;

1-N-cyclohexyl-1-phenyl-2-N'-[(2-methoxy-4,5-dimethylphenyl)methyl]-1,2-ethanediamine; and 1-N-cyclohexyl-1-N-(6-hydroxyhexyl)-1-phenyl-2-N'-[(2-methoxyphenyl)methyl]-1,2-ethanediamine.

This invention also relates to a method of treating or preventing a disorder selected from stroke, epilepsy, head trauma, spinal cord trauma, ischemic neuronal damage such as cerebral ischemic damage from stroke or vascular occlusion (e.g., during open heart surgery), excitotoxic neuronal damage (e.g., in stroke or epilepsy) and amyotrophic lateral sclerosis in a mammal, including a human, comprising administering to said mammal an amount of a compound of the formula

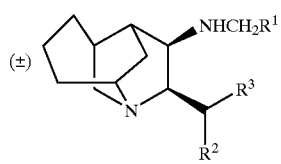

XIII wherein $R^1$ is cycloalkyl having from five to seven carbon atoms, pyrrolyl, thienyl, pyridyl, phenyl or substituted phenyl, wherein said substituted phenyl is substituted with from one to three substituents independently selected from fluorine, chlorine, bromine, trifluoromethyl, alkyl having from one to three carbon atoms, alkoxy having from one to three carbon atoms, carboxy, alkoxycarbonyl having from one to three carbon atoms in the alkoxy moiety and benzyloxycarbonyl;

$R^2$ is furyl, thienyl, pyridyl, indolyl, biphenyl, phenyl or substituted phenyl, wherein said substituted phenyl is substituted with one or two substituents independently selected from fluorine, chlorine, bromine, trifluoromethyl, alkyl having from one to three carbon atoms, alkoxy having from one to three carbon atoms, carboxy, alkoxycarbonyl having from one to three carbon atoms in the alkoxy moiety and benzyloxycarbonyl; and $R^3$ is thienyl, phenyl, fluorophenyl, chlorophenyl or bromophenyl, or a pharmaceutically acceptable salt of such compound, that is effective in treating or preventing such disorder.

Preferred embodiments of this invention include methods of treating or preventing a disorder selected from stroke, epilepsy, head trauma, spinal cord trauma, ischemic neuronal damage such as cerebral ischemic damage from stroke or vascular occlusion (e.g., during open heart surgery), excitotoxic neuronal damage (e.g., in stroke or epilepsy) and amyotrophic lateral sclerosis in a mammal, including a human, that comprise administering to said mammal an amount of a compound as defined in paragraphs (63) through (65) below, or a pharmaceutically acceptable salt thereof, that is effective in treating or preventing such disorder.

(63) A compound of the formula XIII, wherein $R^1$ is phenyl or substituted phenyl.

(64) A compound of the formula XIII, wherein $R^1$ is methoxyphenyl.

(65) A compound of the formula XIII, wherein said compound is (±)-cis-9-diphenylmethyl-N-((2-methoxyphenyl)methyl)-10-azatricyclo[4.4.1.0$^{5.7}$]undecan-8-amine.

This invention also relates to a method of treating or preventing a disorder selected from stroke, epilepsy, head trauma, spinal cord trauma, ischemic neuronal damage such as cerebral ischemic damage from stroke or vascular occlusion (e.g., during open heart surgery), excitotoxic neuronal damage (eg, in stroke or epilepsy) and amyotrophic lateral sclerosis in a mammal, including a human, comprising administering to said mammal an amount of a compound of the formula

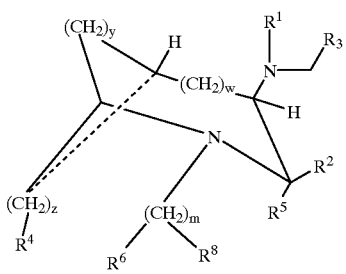

XIV wherein m is an integer from 0 to 8, and any one of the carbon-carbon single bonds of $(CH_2)_m$, wherein both carbon atoms of such bond are bonded to each other and to another carbon atom in the $(CH_2)_m$ chain, may optionally be replaced by a carbon-carbon double bond or a carbon-carbon triple bond, and any one of the carbon atoms of said $(CH_2)_m$ may optionally be substituted with $R^8$;

w is an integer from 0 to 2;

y is an integer from 1 to 4;

z is an integer from 1 to 4, and wherein any one of the carbon atoms of said $(CH_2)_z$ may optionally be substituted with $R^4$;

$R^1$ is hydrogen or $(C_1-Ca)$alkyl optionally substituted with hydroxy, alkoxy or fluoro;

$R^2$ is a group selected from hydrogen, $(C_1-C_6)$straight or branched alkyl, $(C_3-C_7)$cycloalkyl wherein one of the carbon atoms may optionally be replaced by nitrogen, oxygen or sulfur; aryl selected from phenyl, indanyl, and naphthyl; heteroaryl selected from thienyl, furyl, pyridyl, thiazolyl, isothiazolyl, oxazolyl, isoxazolyl, triazolyl, tetrazolyl and quinolyl; phenyl $(C_2-C_6)$alkyl, benzhydryl and benzyl, wherein one of the phenyl moieties of said benzhydryl may optionally be replaced by naphthyl, thienyl, furyl or pyridyl and wherein each of said aryl and heteroaryl groups and the phenyl moieties of said benzyl, phenyl$(C_2-C_6)$alkyl and benzhydryl may optionally be substituted with one or more substituents independently selected from halo, nitro, $(C_1-C_6)$alkyl, $(C_1-C_6)$alkoxy, trifluoromethyl, amino, $(C_1-C_6)$-alkylamino,

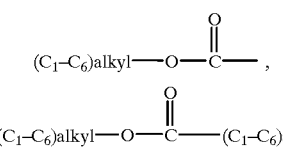

-continued

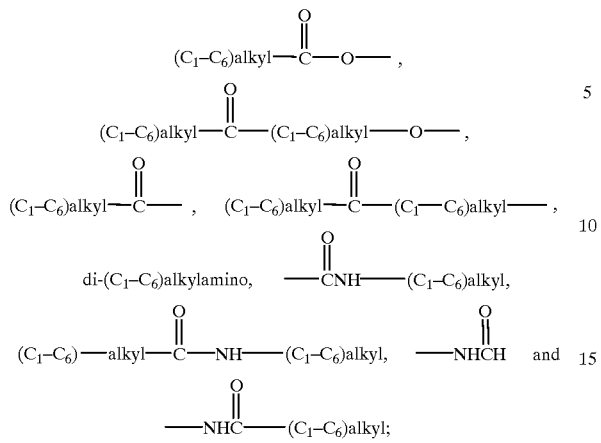

$R^5$ is hydrogen, phenyl or $(C_1–C_6)$alkyl;

or $R^2$ and $R^5$, together with the carbon to which they are attached, form a saturated carbocyclic ring having from 3 to 7 carbon atoms wherein one of said carbon atoms may optionally be replaced by oxygen, nitrogen or sulfur;

$R^3$ is aryl selected from phenyl, indanyl, and naphthyl; heteroaryl selected from thienyl, furyl, pyridyl, thiazolyl, isothiazolyl, oxazolyl, isoxazolyl, triazolyl, tetrazolyl and quinolyl; and cycloalkyl having 3 to 7 carbon atoms wherein one of said carbon atoms may optionally be replaced by nitrogen, oxygen or sulfur; wherein each of said aryl and heteroaryl groups may optionally be substituted with one or more substituents, and said $(C_3–C_7)$cycloalkyl may optionally be substituted with one or two substituents, each of said substituents being independently selected from halo, nitro, $(C_1–C_6)$alkyl optionally substituted with from one to three fluorine atoms, $(C_1–C_6)$alkoxy optionally substituted with from one to three fluorine atoms, trifluoromethyl, phenyl, amino, $(C_1–C_6)$alkylamino, $(C_1–C_6)$dialkyl amino,

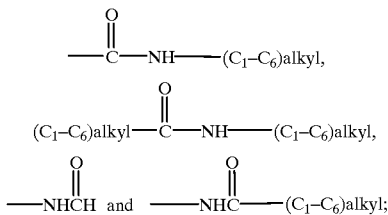

$R^4$ is independently selected from hydrogen, hydroxy, halo, amino, oxo (=O), nitrile, $(C_1–C_6)$alkylamino, di-$(C_1–C_6)$alkylamino, $(C_1–C_6)$alkoxy,

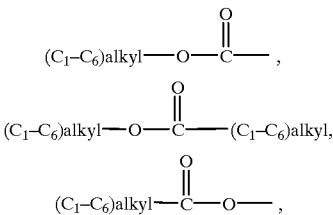

-continued

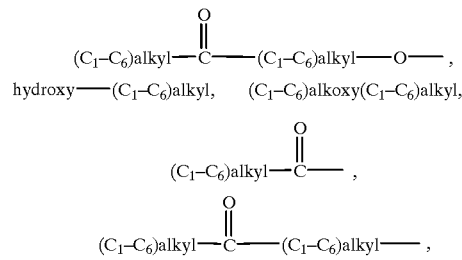

and the groups set forth in the definition of $R^2$;

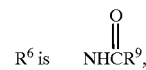

$NHCH_2R^9$, $NHSO_2R^9$ or one of the groups set forth in any of the definitions of $R^2$, and $R^4$;

$R^8$ is oximino (=NOH) or one of the groups set forth in any of the definitions of $R^2$, and $R^4$;

$R^9$ is $(C_1–C_6)$alkyl, hydrogen, phenyl or phenyl $(C_1–C_6)$alkyl;

with the proviso that (a) when m is 0, $R^8$ is absent and $R^6$ is hydrogen, (b) neither $R^4$, $R^6$, nor $R^8$ can form, together with the carbon to which it is attached, a ring with $R^5$, (c) the sum of y and z must be less than 7; or a pharmaceutically acceptable salt thereof, that is effective in treating or preventing such disorder.

Preferred embodiments of this invention include methods of treating or preventing a disorder selected from stroke, epilepsy, head trauma, spinal cord trauma, ischemic neuronal damage such as cerebral ischemic damage from stroke or vascular occlusion (e.g., during open heart surgery), excitotoxic neuronal damage (e.g., in stroke or epilepsy) and amyotrophic lateral sclerosis in a mammal, including a human, that comprise administering to said mammal an amount of a compound as defined in paragraphs (66) through (68) below, or a pharmaceutically acceptable salt thereof, that is effective in treating or preventing such disorder.

(66) A compound of the formula XIV, wherein $R^2$ is a radical selected from hydrogen, phenyl, naphthyl and benzhydryl; wherein each of said phenyl, naphthyl and benzhydryl may optionally be substituted with one or more substituents independently selected from halo, nitro, $(C_1–C_6)$ alkyl, $(C_1–C_6)$alkoxy, trifluoromethyl, amino, $(C_1–C_6)$-alkylamino,

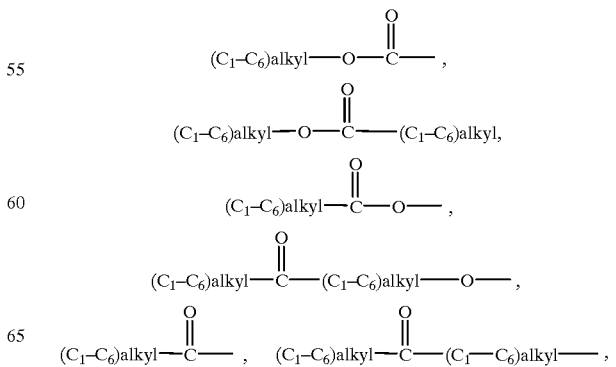

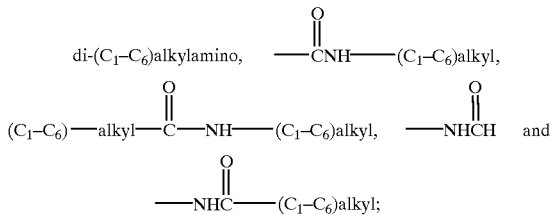

and wherein one of the phenyl moieties of said benzhydryl may optionally be replaced by naphthyl, thienyl, furyl or pyridyl.

(67) A compound of the formula XIV, wherein $R^2$ is a group selected from hydrogen, phenyl, naphthyl and benzhydryl; wherein each of said phenyl, naphthyl and benzhydryl may optionally be substituted with one or more substituents independently selected from halo, nitro, $(C_1-C_6)$alkyl, $(C_1-C_6)$alkoxy, trifluoromethyl, amino, $(C_1-C_6)$-alkylamino,

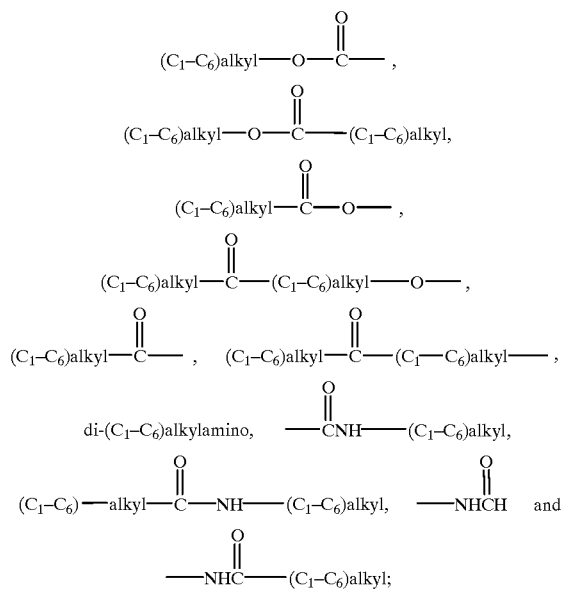

and wherein one of the phenyl moieties of said benzhydryl may optionally be replaced by naphthyl, thienyl, furyl or pyridyl; and $R^4$ is independently selected from hydrogen, hydroxy, halo, amino, oxo (=o), nitrile, $(C_1-C_6)$alkylamino, di-$(C_1-C_6)$alkylamino, $(C_1-C_6)$alkoxy,

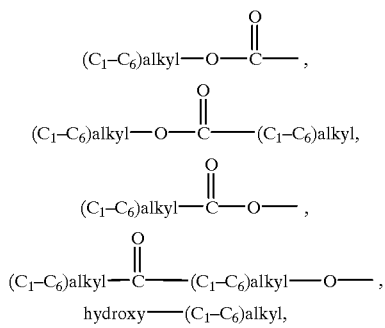

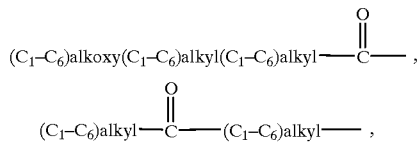

$(C_1-C_6)$alkyl and phenyl.

(68) A compound of the formula XIV, wherein said compound is (3RS, 4RS)-3-phenyl-4-(2-methoxybenzyl)amino-2-azabicyclo[3.3.1]nonane.

This invention also relates to a method of treating or preventing a disorder selected from stroke, epilepsy, head trauma, spinal cord trauma, ischemic neuronal damage such as cerebral ischemic damage from stroke or vascular occlusion (eg, during open heart surgery), excitotoxic neuronal damage (e.g., in stroke or epilepsy) and amyotrophic lateral sclerosis in a mammal, including a human, comprising administering to said mammal a compound of the formula

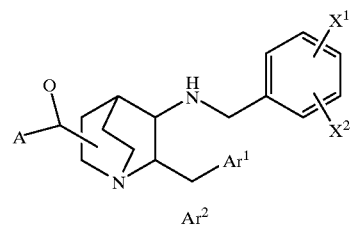

XV wherein $X^1$ is $C_1-C_5$ alkoxy or halosubstituted $(C_1-C_5)$ alkoxy;

$X^2$ is hydrogen, halogen, $(C_1-C_5)$alkyl, $(C_2-C_5)$alkenyl, $(C_2-C_5)$alkynyl, $(C_1-C_5)$alkoxy, $(C_1-C_5)$alkylthio, $(C_1-C_5)$alkylsulfinyl, $(C_1-C_5)$alkylsulfonyl, halosubstituted $(C_1-C_5)$alkyl, halosubstituted $(C_1-C_5)$alkoxy, $(C_1-C_5)$alkylamino, dialkylamino having from 1 to 5 carbon atoms in each alkyl moiety, $(C_1-C_5)$ alkylsulfonylamino (which may be substituted by halogen),

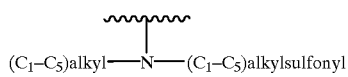

(which may be substituted by halogen in the alkylsulfonyl moiety), $(C_1-C_5)$alkanoylamino (which may be substituted by halogen) or

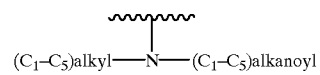

(which may be substituted by halogen in the alkanoyl moiety);

$Ar^1$ and $Ar_2$ are each, independently, thienyl, phenyl, fluorophenyl, chlorophenyl or bromophenyl;

A is $Y-(CH_2)_m-CH(R^2)-(CH_2)_n-NR^1-$;

$R^1$ is hydrogen, $(C_1-C_5)$alkyl, benzyl or $-(CH_2)_p-Y$;

$R^2$ is hydrogen, $(C_1-C_5)$alkyl (which may be substituted by a substituent selected from the group consisting of hydroxy, amino, methylthio and mercapto), benzyl, 4-hydroxybenzyl, 3-indolylmethyl or $-(CH_2)_p-Y$;

Y is —CN, —CH$_2$Z or —COZ;

Z is hydroxy, amino, (C$_1$–C$_5$)alkoxy, (C$_1$–C$_5$)alkylamino or dialkylamino having from 1 to 5 carbon atoms in each alkyl moiety;

m, n and p are each, independently, 0, 1, 2 or 3; and

R$^1$ and R$^2$ may be connected to form a ring;

or a pharmaceutically acceptable salt of such compound, that is effective in treating or preventing such disorder.

Preferred embodiments of this invention include methods of treating or preventing a disorder selected from stroke, epilepsy, head trauma, spinal cord trauma, ischemic neuronal damage such as cerebral ischemic damage from stroke or vascular occlusion (ecg, during open heart surgery), excitotoxic neuronal damage (e.g., in stroke or epilepsy) and amyotrophic lateral sclerosis in a mammal, including a human, that comprise administering to said mammal an amount of a compound as defined in paragraph (69) below, or a pharmaceutically acceptable salt thereof, that is effective in treating or preventing such disorder.

(69) A compound of the formula XV, wherein said compound is selected from the group consisting of:

(3R, 4S, 5S, 6S)-N-carbamoylmethyl-5-(5-isopropyl-2-methoxybenzylamino)-6-diphenylmethyl-1-azabicyclo[2.2.2]octane-3-carboxamide;

(3R, 4S, 5S, 6S)-N-carboxymethyl-5-(5-isopropyl-2-methoxybenzylamino)-6-diphenylmethyl-1-azabicyclo[2.2.2]octane-3-carboxamide;

(3R, 4S, 5S, 6S)-3-(2-carbamoylpyrrolidin-1-yl)carbonyl-5-(5-isopropyl-2-methoxybenzylamino)-6-diphenylmethyl-1-azabicyclo[2.2.2]octane;

(3R*, 4S*, 5S*, 6S*)-N-(1-carbamoylethyl)-5-(5-isopropyl-2-methoxybenzylamino)-6-diphenylmethyl-1-azabicyclo[2.2.2]octane-3-carboxamide;

(3R, 4S, 5S, 6S)-N-(1-carbamoyl-3-methylbutyl)-5-(5-isopropyl-2-methoxybenzylamino)-6-diphenylmethyl-1-azabicyclo[2.2.2]octane-3-carboxamide; and (3R, 4S, 5S, 6S)-N-(2-carbamoylethyl)-5-(5-isopropyl-2-methoxybenzylamino)-6-diphenylmethyl-1-azabicyclo[2.2.2]octane-3-carboxamide.

This invention also relates to a method of treating or preventing a disorder selected from stroke, epilepsy, head trauma, spinal cord trauma, ischemic neuronal damage such as cerebral ischemic damage from stroke or vascular occlusion (e.g., during open heart surgery), excitotoxic neuronal damage (e.g., in stroke or epilepsy) and amyotrophic lateral sclerosis in a mammal, including a human, comprising administering to said mammal an amount of a compound of the formula

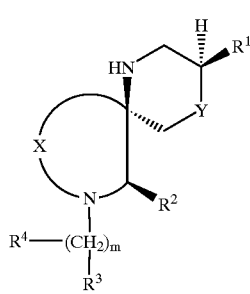

XVI wherein R$^1$ is phenyl optionally substituted with one or more substituents, preferably with from one to three substituents, independently selected from hydrogen, halo, nitro, (C$_1$–C$_{10}$) alkyl optionally substituted with from one to three fluorine atoms, (C$_1$–C$_{10}$)alkoxy optionally substituted with from one to three fluorine atoms, trifluoromethyl, hydroxy, phenyl, cyano, amino, (C$_1$–C$_6$)-alkylamino, di-(C$_1$–C$_6$)alkylamino,

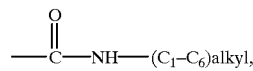

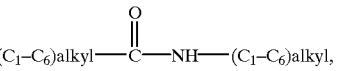

(C$_1$–C$_4$)alkoxy(C$_1$–C$_4$)alkyl, —S(O)$_v$—(C$_1$–C$_{10}$)-alkyl wherein v is zero, one or two, —S(O)$_v$-aryl wherein v is zero, one or two, —O-aryl, —SO$_2$NR$^4$R$^5$ wherein each of R$^4$ and R$^5$ is, independently, (C$_1$–C$_6$)alkyl, or R$^4$ and R$^5$, together with the nitrogen to which they are attached, form a saturated ring containing one nitrogen and from 3 to 6 carbons,

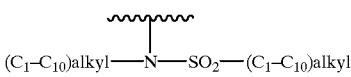

wherein one or both of the alkyl moieties may optionally be substituted with from one to three fluorine atoms, —N(SO$_2$—(C$_1$–C$_{10}$)alkyl)$_2$ and

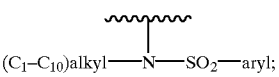

and wherein the aryl moieties of said —S(O)$_v$-aryl, —O-aryl and

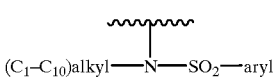

are independently selected from phenyl and benzyl and may optionally be substituted with from one to three substituents independently selected from (C$_1$–C$_4$)alkyl, (C$_1$–C$_4$)alkoxy and halo;

or R$^1$ is phenyl substituted with a group having the formula

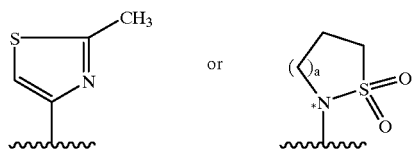

wherein a is 0, 1 or 2 and the asterisk represents a position meta to the point of attachment of R$^1$;

R$^2$ is selected from (C$_1$–C$_6$) straight or branched alkyl, (C$_3$–C$_7$)cycloalkyl wherein one of the carbon atoms may optionally be replaced by nitrogen, oxygen or sulfur; aryl selected from biphenyl, phenyl, indanyl and naphthyl; heteroaryl selected from thienyl, furyl, pyridyl, thiazolyl, isothiazolyl, oxazolyl, isoxazolyl, triazolyl, tetrazolyl and quinolyl; phenyl $(C_1-C_6)$alkyl, benzhydryl and benzyl, wherein each of said aryl and heteroaryl groups and the phenyl moieties of said benzyl, phenyl $(C_2-C_6)$alkyl and benzhydryl may optionally be substituted with one or more substituents, preferably with from one to three substituents, independently selected from halo, nitro, $(C_1-C_{10})$alkyl optionally substituted with from one to three fluorine atoms, $(C_1-C_{10})$alkoxy optionally substituted with from one to three fluorine atoms, amino, hydroxy-$(C_1-C_6)$alkyl, $(C_1-C_6)$alkoxy-$(C_1-C_6)$alkyl, $(C_1-C_6)$-alkylamino,

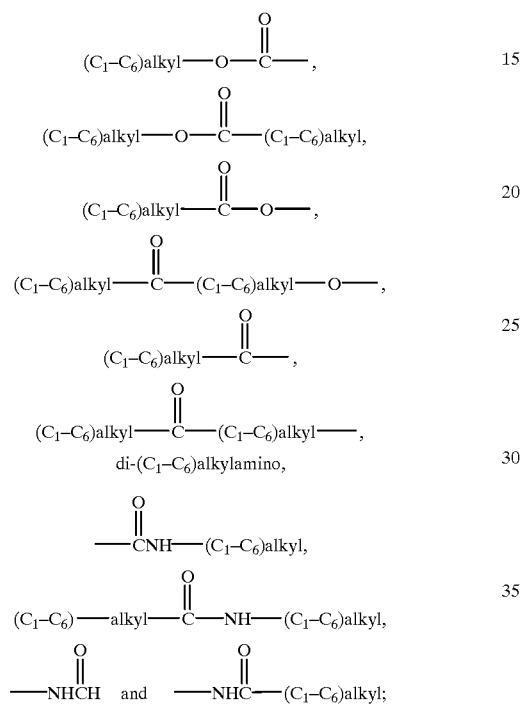

di-$(C_1-C_6)$alkylamino,

and wherein one of the phenyl moieties of said benzhydryl may optionally be replaced by naphthyl, thienyl, furyl or pyridyl;

m is an integer from 0 to 8, and any one of the carbon-carbon single bonds of $(CH_2)_m$, wherein both carbon atoms of such bond are bonded to each other and to another carbon atom in the $(CH_2)_m$ chain, may optionally be replaced by a carbon-carbon double bond or a carbon-carbon triple bond, and any one of the carbon atoms of said $(CH_2)_m$ may optionally be substituted with $R^4$;

$R^3$ is selected from $$\underset{NHCR^8,}{\overset{O}{\parallel}}$$

$NHCH_2R^8$, $SO_2R^1$, $AR^9$, $CO_2H$ and the radicals set forth in the definitions of $R^2$, $R^6$ and $R^7$;

A is $CH_2$, nitrogen, oxygen, sulfur or carbonyl;

$R^8$ is $(C_1-C_6)$alkyl, hydrogen, phenyl or phenyl $(C_1-C_6)$alkyl;

$R^4$ is selected from oximino (=NOH) and the radicals set forth in the definitions of $R^2$, $R^6$ and $R^7$;

$R^9$ is a monocyclic or bicyclic heterocycle selected from the group consisting of pyrimidinyl, benzoxazolyl, 2,3-dihydro-3-oxobenzisosulfonazol-2-yl, morpholin-1-yl, thiomorpholin-1-yl, benzofuranyl, benzothienyl, indolyl, isoindolyl, isoquinolinyl, furyl, pyridyl, isothiazolyl, oxazolyl, triazolyl, tetrazolyl, quinolyl, thiazolyl, thienyl, and groups of the formulae

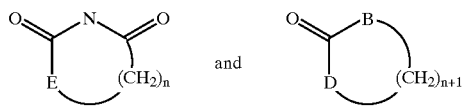

wherein B and D are selected from carbon, oxygen and nitrogen, and at least one of B and D is other than carbon; E is carbon or nitrogen; n is an integer from 1 to 5; any one of the carbon atoms of said $(CH_2)_n$ and $(CH_2)_{n+1}$ may be optionally substituted with $(C_1-C_6)$ alkyl or $(C_2C_6)$spiroalkyl; and either any one pair of the carbon atoms of said $(CH_2)_n$ and $(CH_2)_{n+1}$ may be bridged by a one or two carbon atom linkage, or any one pair of adjacent carbon atoms of said $(CH_2)_n$ and $(CH_2)_{n+1}$ may form, together with from one to three carbon atoms that are not members of the carbonyl containing ring, a $(C_3-C_5)$ fused carbocyclic ring;

X is $(CH_2)_q$ wherein q is two or three and wherein one of the carbon-carbon single bonds in said $(CH_2)_q$ may optionally be replaced by a carbon-carbon double bond, and wherein any one of the carbon atoms of said $(CH_2)_q$ may optionally be substituted with $R^6$, and wherein any one of the carbon atoms of said $(CH_2)_q$ may optionally be substituted with $R^7$;

$R^6$ and $R^7$ are independently selected from hydrogen, hydroxy, halo, amino, oxo (=O), cyano, hydroxy-$(C_1-C_6)$alkyl, $(C_1-C_6)$alkoxy-$(C_1-C_6)$alkyl, $(C_1-C_6)$ alkylamino, di-$(C_1-C_6)$alkylanino,

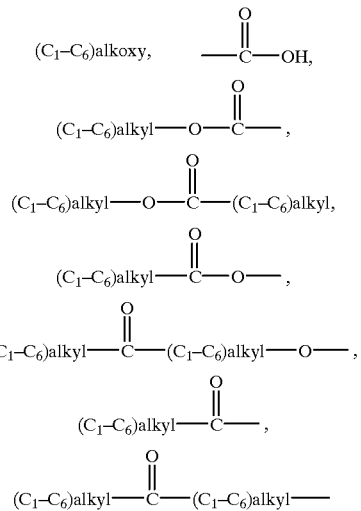

and the radicals set forth in the definition of $R^2$; and

Y is $(CH_2)_z$ wherein z is zero or one;

with the proviso that: (a) when A is —$(CH_2)$— or carbonyl, $R^9$ cannot be furyl, pyridyl, isothiazolyl, oxazolyl, triazolyl, tetrazolyl, quinolyl, thiazolyl or thienyl; (b) when m is zero, one of $R^3$ and $R^4$ is absent and the other is hydrogen; and (c) when $R^6$ or $R^7$ is attached to a carbon atom of X that is adjacent to the ring nitrogen, then $R^6$ or $R^7$, respectively, must be a substituent wherein the point of attachment is a carbon atom;

or a pharmaceutically acceptable salt of such compound, that is effective in treating or preventing such disorder.

Preferred embodiments of this invention include methods of treating or preventing a disorder selected from stroke, epilepsy, head trauma, spinal cord trauma, ischemic neuronal damage such as cerebral ischemic damage from stroke or vascular occlusion (e.g., during open heart surgery), excitotoxic neuronal damage (e.g., in stroke or epilepsy) and amyotrophic lateral sclerosis in a mammal, including a human, that comprise administering to said mammal an amount of a compound as defined in paragraph (70)–(75) below, or a pharmaceutically acceptable salt thereof, that is effective in treating or preventing such disorder.

(70) A compound of the formula XVI wherein z is one.
(71) A compound of the formula XVI wherein q is three.
(72) A compound of the formula XVI wherein q is three, m is zero, $R^3$ is hydrogen and $R^4$ is absent.
(73) A compound of the formula XVI wherein $R^1$ is phenyl substituted with from one to three substituents independently selected from $(C_1–C_6)$alkyl optionally substituted with from one to three fluorine atoms and $(C_1–C_6)$alkoxy optionally substituted with from one to three flourine atoms.
(74) A compound of the formula XVI wherein z is one, m s zero, $R^4$ is absent, and each of $R^3$, $R^6$ and $R^7$ is hydrogen.
(75) A compound of the formula XVI that is selected from the group consisting of:

(±)-[3R-[3α,6α (R*)]]-3-phenyl-7-phenyl-1,8-diazaspiro[5.5]undecane; and (±)-[3R-[3α,6α (R*)]]-3-(2-methoxyphenyl)-7-phenyl-1,8-diazaspiro[5.5]undecane.

Other compounds of the formula I include the following:

(±)-[3R-[3α,6α (R*)]]-3-(2-methoxy-5-trifluoromethoxyphenyl)-7-phenyl-1,8-diazaspiro[5.5]undecane;

(±)-[3R-[3α,6α (R*)]]-3-(5-chloro-2-methoxyphenyl)-7-phenyl-1,8-diazaspiro[5.5]undecane;

(±)-[3R-[3α, 6α (R*)]]-3-(5-isopropyl-2-methoxyphenyl)-7-phenyl-1,8-diazaspiro[5.5]undecane;

(±)-[3R-[3α,6α (R*)]]-3-(5-tertbutyl-2-methoxyphenyl)-7-phenyl-1,8-diazaspiro[5.5]undecane;

(±)-[3R-[3α,6α (R*)]]-3-(2-methoxy-5-(N-methyl-N-methylsulfonylaminophenyl)-7-phenyl-1,8-diazaspiro[5.5]undecane;

(±)-[3R-[3α,6α (R*)]]-3-(2-iodophenyl)-7-phenyl-1,8-diazaspiro[5.5]undecane;

(±)-[3R-[3α,6α (R*)]]-3-(2-methoxy-4-methylphenyl)-7-phenyl-1,8-diazaspiro[5.5]undecane;

(±)-[3R-[3α,6α (R*)]]-3-(2-isopropoxyphenyl)-7-phenyl-1,8-diazaspiro[5.5]undecane;

(±)-[3R-[3α,6α (R*)]]-3-(2-difluoromethoxy-5-trifluoromnethoxyphenyl)-7-phenyl-1,8-diazaspiro[5.5]undecane;

(±)-[3R-[3α,5α (R*)]]-3-(2-methoxyphenyl)-6-phenyl-1,7-diazaspiro[4.5]decane;

(±)-[3R-[3α,5α (R*)]]-3-(2-methoxy-5-trifluoromethoxyphenyl)-6-phenyl-1,7-diazaspiro[4.5]decane;

(±)-[3R-[3α,5α (R*)]]-3-(5-chloro-2-methoxyphenyl)-6-phenyl-1,7-diazaspiro[4.5]decane;

(±)-[3R-[3α,5α (R*)]]-3-(5-isopropyl-2-methoxyphenyl)-6-phenyl-1,7-diazaspiro[4.5]decane; and (±)-[3R-[3α,5α (R*)]]-3-(5-tert.butyl-2-methoxyphenyl)-6-phenyl-1,7-diazaspiro[4.5]decane.

This invention also relates to a method of treating or preventing a disorder selected from stroke, epilepsy, head trauma, spinal cord trauma, ischemic neuronal damage such as cerebral ischemic damage from stroke or vascular occlusion (e.g., during open heart surgery), excitotoxic neuronal damage (e.g., in stroke or epilepsy) and amyotrophic lateral sclerosis in a mammal, including a human, comprising administering to said mammal an amount of a compound of the formula

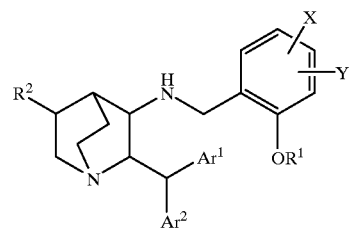

XVII wherein $Ar^1$ and $Ar^2$ are each independently aryl or substituted aryl;

$R^1$ is alkyl having from 1 to 6 carbon atoms;

$R^2$ is hydrogen or alkyl having from 1 to 6 carbon atoms;

and either X and Y are taken separately and they are each, independently, hydrogen, dialkylphosphoryl having from 2 to 12 carbon atoms, alkyl having from 1 to 6 carbon atoms; or X and Y are taken together and they represent a hydrocarbon chain having 3, 4, or 5 carbon atoms, optionally containing up to 2 double bonds and optionally having 1 or 2 substituents selected from oxo, hydroxy and alkyl having from 1 to 6 carbon atoms;

provided that when X and Y are taken together they are attached to adjacent carbon atoms; and provided that if either X or Y is hydrogen, then the other one must be alkenyl or alkynyl;

or a pharmaceutically acceptable salt thereof, that is effective in treating or preventing such disorder.

The term "alkylthio" is used in formula XVII to mean —$SR^4$ ($R^4$ is alkyl) including, but not limited to, methylthio, ethylthio, n-propylthio, isopropylthio, n-butylthio, isobutylthio, t-butylthio and the like.

The term "dialkylphosphoryl" is used in formula XVII to mean —$P(O)$ $(OR^5)$ $(OR^6)$ ($R^5$ and $R^6$ are alkyl) including, but not limited to, diethylphosphoryl, ethylmethylphosphoryl and the like.

Preferred embodiments of this invention include methods of treating or preventing a disorder selected from stroke, epilepsy, head trauma, spinal cord trauma, ischemic neuronal damage such as cerebral ischemic damage from stroke or vascular occlusion (e.g., during open heart surgery), excitotoxic neuronal damage (e, in stroke or epilepsy) and amyotrophic lateral sclerosis in a mammal, including a human, that comprise administering to said mammal an amount of a compound as defined in paragraphs (76)–(79) below, or a pharmaceutically acceptable salt thereof, that is effective in treating or preventing such disorder.

(76) Compounds of formula XVII wherein $Ar^1$ and $Ar^2$ are each phenyl, $R^1$ is methyl, $R^2$ is hydrogen, X is alkenyl or alkynyl and Y is hydrogen.

(77) Compounds of the formula XVII wherein $Ar^1$ and $Ar^2$ are each phenyl, $R^1$ is methyl, $R^2$ is hydrogen and X and Y are each alkyl.

(78) Compounds of the formula XVII wherein $Ar^1$ and $Ar^2$ are each phenyl, $R^1$ is methyl, $R^2$ is hydrogen and X and Y represent $CH_2CH_2CH_2$ or $CH_2CH_2CH_2CH_2$.

(79) A compound of the formula XVII that is selected from:
  (2S, 3S)-N-(5-Isopropenyl-2-methoxyphenyl)methyl-2-diphenylmethyl-1-azabicyclo[2.2.2]octan-3-amine;
  (2S, 3S)-N-(2-Methoxy-5-vinylphenyl)methyl-2-diphenylmethyl-1-azabicyclo[2.2.2]octan-3-amine;
  (2S, 3S)-N-(2-Methoxy-4,5-dimethylphenyl)methyl-2-diphenylmethyl-1-azabicyclo[2.2.2]octan-3-amine;
  (2S, 3S)-N-(5,6,7,8-Tetrahydro-3-methoxy-2-naphthyl)methyl-2-diphenylmethyl-1-azabicyclo[2.2.2]octan-3-amine;
  (2S, 3S)-N-(5-Methoxyindan-6-yl)methyl-6-diphenylmethyl-1-azabicyclo[2.2.2]octan-3-amine;
  (2S, 3S)-3-(2,4-Dimethoxy-5-ethylbenzylamino)-2-diphenylmethyl-1-azabicyclo[2.2.2]octane; and
  (2S, 3S)-2-Diphenylmethyl-N-[2-methoxy-5-(diethylphosphoryl)phenyl]methyl-1-azabicyclo[2.2.2]octan-3-amine.

This invention also relates to a method of treating or preventing a disorder selected from stroke, epilepsy, head trauma, spinal cord trauma, ischemic neuronal damage such as cerebral ischemic damage from stroke or vascular occlusion (e.c., during open heart surgery), excitotoxic neuronal damage (e.g., in stroke or epilepsy) and amyotrophic lateral sclerosis in a mammal, including a human, comprising administering to said mammal an amount of a compound of the formula

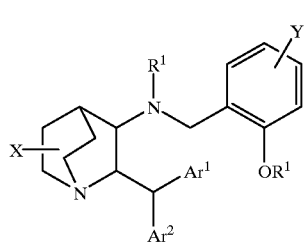

XVIII wherein $Ar^1$ and $Ar^2$ are each, independently, thienyl, phenyl, fluorophenyl, chlorophenyl or bromophenyl;
  X is $-CONR^3R^4$, $-CO_2R^3$, $-CH_2OR^3$, $-CH_2NR^3R^4$ or $-CONR^3OR^4$;
  $R^1$, $R^3$ and $R^4$ are each, independently, hydrogen or alkyl having 1 to 4 carbon atoms;
  $R^2$ is alkyl having 1 to 4 carbon atoms;
  Y is alkylsulfonyl having 1 to 4 carbon atoms, N-alkyl-N-alkanoylamino (which may be substituted by halogen in the alkanoyl moiety) having 1 to 4 carbon atoms in the alkyl and the alkanoyl moieties, N-alkyl-N-alkylsulfonylamino (which may be substituted by halogen in the alkylsulfonyl moiety) having 1 to 4 carbon atoms in the alkyl and the alkyl sulfonyl moieties, alkenyl having 2 to 4 carbon atoms, alkynyl having 2 to 4 carbon atoms, halosubstituted alkyl having 1 to 4 carbon atoms, alkylamino having 1 to 4 carbon atoms, alkanoylamino (which may be substituted by halogen) having 1 to 4 carbon atoms or alkylsulfonylamino (which may be substituted by halogen) having 1 to 4 carbon atoms;
  or a pharmaceutically acceptable salt thereof, that is effective in treating or preventing disorder.

Preferred embodiments of this invention include methods of treating or preventing a disorder selected from stroke, epilepsy, head trauma, spinal cord trauma, ischemic neuronal damage such as cerebral ischemic damage from stroke or vascular occlusion (e.g., during open heart surgery), excitotoxic neuronal damage (e.g., in stroke or epilepsy) and amyotrophic lateral sclerosis in a mammal, including a human, that comprise administering to said mammal an amount of a compound as defined in paragraphs (80)–(86) below, or a pharmaceutically acceptable salt thereof, that is effective in treating or preventing such disorder.
  (80) A compound of the formula XVIII wherein $Ar^1$ and $Ar^2$ are each phenyl.
  (81) A compound as described in paragraph (80) wherein $R^2$ is methyl and $R^1$ is hydrogen.
  (82) A compound as described in paragraph (81) wherein X is at the 3-position of the quinuclidine ring and X is carboxy or aminocarbonyl.
  (83) A compound as described in paragraph (82) wherein Y is said alkenyl.
  (84) A compound as described in paragraph (83) wherein Y is isopropenyl.
  (85) A compound as described in paragraph (82) wherein Y is methylsulfonyl, N-acetyl-N-methylamino or N-methyl-N-methylsulfonylamino.
  (86) A compound of the formula XVIII that is selected from:
    (3R, 4S, 5S, 6S)-5-(5-Isopropenyl-2-methoxybenzyl-amino)-25 6-diphenylmethyl-1-azabicyclo[2.2.2]octane-3-carboxamide;
    (3R, 4S, 5S, 6S)-6-Diphenylmethyl-5-(2-methoxy-5-methylsulfonylbenzylamino)-1-azabicyclo[2.2.2]octane-3-carboxamide;
    (3R, 4S, 5S, 6S)-5-5-[N-Acetyl-N-methylamino)-2-methoxy benzyl amino]-6-diphenyl methyl-1-azabicyclo[2.2.2]octane-3-carboxamide;
    (3R, 4S, 5S, 6S)-6-Diphenylmethyl-5-[2-methoxy-5-(N-methyl-N-methylsulfonylamino)benzylamino]-1-azabicyclo[2.2.2]octane-3-carboxamide; and
    (3R, 4S, 5S, 6S)-6-Diphenylmethyl-5-(2-methoxy-5-methylsulfonylbenzylamino)-1-azabicyclo[2.2.2]octane-3-carboxylic acid.

This invention also relates to a method of treating or preventing a disorder selected from stroke, epilepsy, head trauma, spinal cord trauma, ischemic neuronal damage such as cerebral ischemic damage from stroke or vascular occlusion (exg., during open heart surgery), excitotoxic neuronal damage (eag., in stroke or epilepsy) and amyotrophic lateral sclerosis in a mammal, including a human, comprising administering to said mammal a compound of the formula

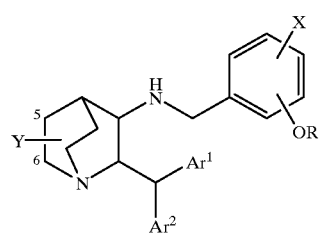

XIX wherein R is $C_1$–$C_6$ alkyl;
  X is $C_1$–$C_6$ alkyl having one or more substituents bonded through a heteroatom;
  $Ar^1$ and $Ar^2$ are each, independently, aryl optionally substituted by one $C_1$–$C_6$ alkyl, $C_1$–$C_6$ alkoxy, $C_1$–$C_6$ alkylthio, halogen, cyano, nitro, phenoxy, mono $C_1$–$C_6$ alkylamino, di $C_1$–$C_6$ alkylamino, halosubstituted $C_1$–$C_6$ alkyl, or halosubstituted $C_1$–$C_6$ alkoxy;

Y is hydrogen, $C_1$–$C_6$ alkyl, $C_1$–$C_6$ alkenyl, $C_3$–$C_8$ cycloalkyl, Z—$(CH_2)_p$—, or W—$(CH_2)_m$—$CHR^2$—$(CH_2)_n$—$NR^1CO$ wherein Y is at the 4-, 5- or 6-position on the quinuclidine ring;

$R^1$ is hydrogen, $C_1$–$C_6$ alkyl, benzyl or —$(CH_2)_r$—W;

$R^2$ is hydrogen or $C_1$–$C_6$ alkyl which may be substituted by one hydroxy, amino, methylthio, mercapto, benzyl, 4-hydroxybenzyl, 3-indolylmethyl or —$(CH_2)_r$—W;

Z is $C_1$–$C_6$ alkoxy, —$CONR^4R^5$, —$CO_2R^4$, —$CHR^4OR^5$, —$CHR^4NR^5R^6$, —$COR^4$, —$CONR^4OR^5$ or optionally substituted aryl;

each W is independently cyano, hydroxymethyl, $C_2$–$C_6$ alkoxymethyl, aminomethyl, mono $C_1$–$C_6$ alkylaminomethyl, di $C_1$–$C_6$ alkylaminomethyl, carboxyl, carbamoyl or $C_1$–$C_6$ alkoxycarbonyl;

$R^4$, $R^5$ and $R^6$ are independently hydrogen, $C_1$–$C_6$ alkyl, $C_1$–$C_6$ alkoxy, $C_3$–$C_8$ cycloalkyl or an optionally substituted aryl or heterocyclic group;

p is 0 to 6; and m, n and r are each, independently, 0 to 3;

or a pharmaceutically acceptable salt thereof, that is effective in treating or preventing such disorder.

Preferred embodiments of this invention include methods of treating or preventing a disorder selected from stroke, epilepsy, head trauma, spinal cord trauma, ischemic neuronal damage such as cerebral ischemic damage from stroke or vascular occlusion (e.g., during open heart surgery), excitotoxic neuronal damage (e.g., in stroke or epilepsy) and amyotrophic lateral sclerosis in a mammal, including a human, that comprise administering to said mammal an amount of a compound as defined in paragraphs (87)–(91) below, or a pharmaceutically acceptable salt thereof, that is effective in treating or preventing such disorder.

(87) A compound of the formula XIX wherein X is $C_1$–$C_6$ alkyl having one or two substituents selected from hydroxy, halogen, $C_1$–$C_6$ alkoxy, $C_2$–$C_6$ alkanoyl, $C_2$–$C_6$ alkanoyloxy, $C_1$–$C_6$ alkylthio, mono $C_1$–$C_6$ alkylamino, di $C_1$–$C_6$ alkylamino, amino, cyano and azido.

(88) A compound of the formula XIX as described in paragraph (87) wherein R is methyl and the OR group is at the 2-position; $Ar^1$ and $Ar^2$ are each phenyl, monochlorophenyl or monofluorophenyl; Y is hydrogen or Z—$(CH_2)_p$—, wherein Z is $C_1$–$C_6$ alkoxy, —$CONR^4R^5$, —$CO_2R^4$, —$CHR^4OR^5$, —$CHR^4NR^5R^6$, —$COR^4$ or —$CONR^4OR^5$; and Y is at the 5- or 6-position.

(89) A compound as described in paragraph (88) wherein X is $C_1$–$C_6$ alkyl having one or two substituents selected from hydroxy, $C_1$–$C_6$ alkoxy and $C_1$–$C_6$ alkylthio; $Ar^1$ and $Ar^2$ are each phenyl; and Y is hydrogen or carboxy.

(90) A compound is described in paragraph (89) wherein x is —$C(CH_3)_2OH$, —$C(OH)(CH_3)CH_2OH$, —$C(CH_3)_2OCH_3$ or —$C(CH_3)_2SCH_2CH_3$.

(91) A compound as described in paragraph (90) that is selected from:

(2S, 3S)-N-[5-(1-hydroxy-1-methylethyl)-2-methoxyphenyl]methyl-2-diphenylmethyl-1-azabicyclo[2.2.2]octan-3-amine;

(2S, 3S)-N-(2-methoxy-5-[1-methoxy-1-methylethyl)phenyl]methyl-2-diphenylmethyl-1-azabicyclo[2.2.2]octan-3-amine;

(3R, 4S, 5S, 6S)-3-[5-(1-hydroxy-1-methylethyl)-2-methoxyphenyl]methylamino-6-diphenylmethyl-1-azabicyclo[2.2.2]octan-5-carboxylic acid;

(2S, 3S)-2-diphenylmethyl-N-[5-(1-hydroxy-1-hydroxymethylethyl)-2-methoxyphenyl]methyl-1-azabicyclo[2.2.2]octan-3-amine;

(3R, 4S, 5S, 6S)-3-[5-(1-methoxy-1-methylethyl)-2-methoxyphenyl]methylamino-6-diphenylmethyl-1-azabicyclo[2.2.2]octan-5-carboxylic acid;

(3R, 4S, 5S, 6S)-3-[5-(1-hydroxy-1-methylethyl)-2-methoxyphenyl]methylamino-6-diphenylmethyl-1-azabicyclo[2.2.2]octan-5-carboxylic acid; and (3R, 4S, 5S, 6S)-3-[5-(1-ethylthio-1-methylethyl)-2-methoxyphenyl]methylamino-6-diphenylmethyl-1-azabicyclo[2.2.2]octan-5-carboxylic acid.

This invention also relates to a method of treating or preventing a disorder selected from stroke, epilepsy, head trauma, spinal cord trauma, ischemic neuronal damage such as cerebral ischemic damage from stroke or vascular occlusion (e.g., during open heart surgery), excitotoxic neuronal damage (e.g., in stroke or epilepsy) and amyotrophic lateral sclerosis in a mammal, including a human, comprising administering to said mammal a compound of the formula

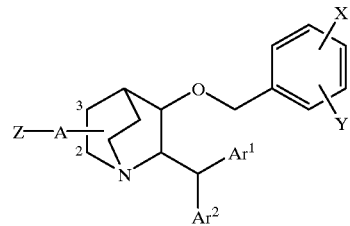

XX wherein X and Y are each hydrogen, halo, $C_1$–$C_6$ alkyl, halosubstituted $C_1$–$C_6$ alkyl, $C_1$–$C_6$ alkoxy, $C_1$–$C_6$ alkylthio, $C_1$–$C_6$ alkylsulfinyl, $C_1$–$C_6$ alkylsulfonyl or tri $C_1$–$C_6$ alkylsilyl;

$Ar^1$ and $Ar^2$ are each aryl optionally substituted by halo;

A is —CO— or —$(CH_2)$—;

Z—A— is at the 2 or 3 position on the quinuclidine ring;

Z is hydroxy, $C_1$–$C_6$ alkoxy, $NR^1R^2$ or $W^1$—$(CH_2)_m$—$CHR^4$—$(CH_2)_n$—$NR^3$ wherein $R^1$ and $R^2$, when taken separately, are each hydrogen or $C_1$–$C_6$ alkyl;

$R^1$ and $R^2$, when taken together with the nitrogen atom to which they are attached, represent piperidino, pyrrolidino, morpholino, thiomorpholino or piperazino;

$R^3$ is hydrogen, $C_1$–$C_6$ alkyl, benzyl or —$(CH_2)_r$—$W^2$;

$R^4$ is hydrogen or $C_1$–$C_6$ alkyl which may be substituted by hydroxy, amino, methylthio, mercapto, benzyl, 4-hydroxylbenzyl, 3-indolylmethyl or —$(CH_2)_s$—$W^3$;

$R^3$ and $R^4$, when taken together, represent $CH_2$ or $CH_2CH_2$;

$W^1$, $W^2$ and $W^3$ are each cyano, hydroxymethyl, $C_1$–$C_6$ alkoxymethyl, aminomethyl, ($C_1$–$C_6$ alkylamino)methyl, (di $C_1$–$C_6$ alkylamino)methyl, carboxyl, ($C_1$–$C_6$ alkyl)carbamoyl, or (di $C_1$–$C_6$ alkyl)carbamoyl, carbamoyl or ($C_1$–$C_6$ alkoxy)carbonyl; and m, n, r and s are each 0, 1, 2 or 3;

or a pharmaceutically acceptable salt thereof that is effective in treating or preventing such disorder.

As used in formula XX, the term "alkylthiol" means —S-alkyl, including but not limited to methylsulfinyl, ethylsulfinyl, isopropylsulfinyl and the like;

As used in formula XX, the term "alkylsulfonyl" means —$SO_2$-alkyl including but not limited to methylsulfonyl, ethylsulfonyl, isopropylsulfonyl and the like; and As used in formula XX, the term "aryl" means aromatic radicals including but not limited to phenyl, naphthyl, pyridyl, quinolyl, thienyl, furyl, oxazolyl, tetrazolyl, thiazolyl, imidazolyl, pyrazolyl and the like. These aryl groups can be substituted by $C_1$–$C_6$ alkyl, $C_1$–$C_6$ alkoxy, $C_1$–$C_6$ alkylthio, halogen, cyano, nitro, phenoxy, mono- or di-$C_1$–$C_6$ alkylamino and the like.

Preferred embodiments of this invention include methods of treating or preventing a disorder selected from stroke, epilepsy, head trauma, spinal cord trauma, ischemic neuronal damage such as cerebral ischemic damage from stroke or vascular occlusion (e.g., during open heart surgery), excitotoxic neuronal damage (e.g., in stroke or epilepsy) and amyotrophic lateral sclerosis in a mammal, including a human, that comprise administering to said mammal an amount of a compound as defined in paragraph (92) below, or a pharmaceutically acceptable salt thereof, that is effective in treating or preventing such disorder.

(92) A compound of the formula XX that is selected from the group consisting of:

(3S, 4R, 5S, 6S)-N-carbamoylmethyl-6-diphenylmethyl-5-(3,5-bis(trifluoromethyl)benzyloxy)-azabicyclo[2.2.2]octane-3-carboxamide;

(3S, 4R, 5S, 6S)-6-diphenylmethyl-5-(3,5-bis(trifluoromethyl)benzyloxy)-azabicyclo[2.2.2]octane-3-carboxamide;

(3S, 4RS, 5S, 6S)-N,N-(3-oxa-1,5-pentylene)-6-diphenylmethyl-5-(3,5-bis(trifluoromethyl)benzyloxy)-1-azabicyclo[2.2.2]octane-3-carboxamide;

(3S, 4 R, 5S, 6S )-6-diphenyl methyl-5-(3,5-dimethylbenzyloxy)-1-azabicyclo[2.2.2]octane-3-carboxylic acid;

(3S, 4R, 5S, 6S)-N,N-diethyl-6-diphenylmethyl-5-(3,5-bis(trifluoromethyl)benzyloxy)-1-azabicyclo[2.2.2]octane-3-carboxamide;

(3S, 4R, 5S, 6S)-6-diphenylmethyl-5-(3-fluoro-5-trifluoromethylbenzyloxy)-1-azabicyclo[2.2.2]octane-3-carboxylic acid;

(3S, 4R, 5S, 6S )-6-diphenylmethyl-5-(3,5-bis(trifluoromethyl)benzyloxy)-azabicyclo[2.2.2]octane-3-carboxylic acid; and (3S, 4R, 5S, 6S)-N,N-dimethyl-6-diphenylmethyl-5-(3,5-bis(trifluoromethyl)benzyloxy)-1-azabicyclo[2.2.2]octane-3-carboxamide.

This invention also relates to a method of treating or preventing a disorder selected from stroke, epilepsy, head trauma, spinal cord trauma, ischemic neuronal damage such as cerebral ischemic damage from stroke or vascular occlusion (e.c., during open heart surgery), excitotoxic neuronal damage (e.q, in stroke or epilepsy) and amyotrophic lateral sclerosis in a mammal, including a human, comprising administering to said mammal a compound of the formula

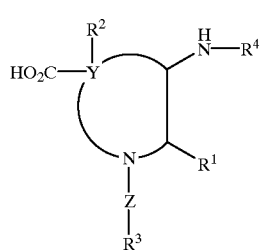

XXI wherein Y is $C_2$–$C_4$ alkylene;

Z is a valence bond or $C_1$–$C_6$ alkylene;

$R^1$ is phenyl, biphenyl, indanyl, naphthyl, thienyl, furyl, pyridyl, thiazolyl, isothiazolyl, oxazolyl, isoxazolyl, tetrazolyl, quinolyl, phenyl $C_1$–$C_6$ alkyl- or benzhydryl, wherein each of the ring mnoieties may optionally be substituted by one or more substituents independently selected from halogen, $C_1$–$C_6$ alkyl, halosubstituted $C_1$–$C_6$ alkyl, $C_1$–$C_6$ alkoxy and halosubstituted $C_1$–$C_6$ alkoxy;

$R^2$ is hydrogen or $C_1$–$C_6$ alkyl;

$R^3$ is hydrogen, hydroxy, cyano, amino or carboxy; and $R^4$ represents a group of the formula (II) or (III)

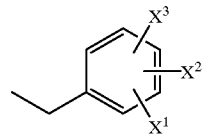

II

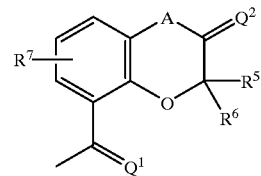

III wherein $X^1$, $X^2$ and $X^3$ are each halo, hydrogen, nitro, $C_1$–$C_6$ alkyl, halosubstituted $C_1$–$C_6$ alkoxy, halosubstituted $C_1$–$C_6$ alkoxy, hydroxy, amino, $C_1$–$C_6$ alkylthio, $C_1$–$C_6$ alkylsulfinyl or $C_1$–$C_6$ alkylsulfonyl;

$Q^1$ and $Q^2$ are each $H_2$, oxygen or sulfur;

A is valence bond, methylene, oxygen, sulfur or NH;

$R^5$ and $R^6$ are each hydrogen or $C_1$–$C_6$ alkyl; and $R^6$ is hydrogen, halogen, $C_1$–Cd alkyl, halosubstituted $C_1$–$C_6$ alkyl or $C_1$–$C_6$ alkoxy;

provided that when Z is a valence bond, $R^3$ must be hydrogen;

or a pharmaceutically acceptable salt thereof, that is effective in treating or preventing such disorder.

Preferred embodiments of this invention include methods of treating or preventing a disorder selected from stroke, epilepsy, head trauma, spinal cord trauma, ischemic neuronal damage such as cerebral ischemic damage from stroke or vascular occlusion (e.g., during open heart surgery), excitotoxic neuronal damage (e.g., in stroke or epilepsy) and amyotrophic lateral sclerosis in a mammal, including a human, that comprise administering to said mammal an amount of a compound as defined in paragraph (93) below, or a pharmaceutically acceptable salt thereof, that is effective in treating or preventing such disorder.

(93) A compound of the formula XXI that is selected from:

(2S*, 3S*, 4S*, 5R*)-4-carboxy-3-[N-(5-isopropyl-2-methoxybenzyl)amino]-5-methyl-2-phenylpyrrolidine and (2S*, 3S*, 5S*)-5-carboxy-3-[N-(2-methoxy-5-trifluoromethoxybenzyl)amino]-2-phenylpiperidine.

The term "halo", as used herein, unless otherwise indicated, includes chloro, fluoro, bromo and iodo.

The term "alkyl", as used herein, unless otherwise indicated, includes saturated monovalent hydrocarbon radicals having straight, branched or cyclic moieties or combinations thereof.

The term "alkenyl", as used herein, unless otherwise indicated, refers to straight or branched hydrocarbon chain radicals having one double bond including, but not limited to, ethenyl, 1- and 2-propenyl, 2-methyl-1-propenyl, 1- and 2-butenyl.

The term "alkoxy", as used herein, unless otherwise indicated, refers to —O-alkyl, wherein alkyl is defined as above, and includes, but is not limited to methoxy, ethoxy, propoxy, isopropoxy, n-butoxy, isobutoxy and t-butoxy.

The term "alkylthio", as used herein, unless otherwise indicated, refers to —S-alkyl, wherein alkyl is defined as above, and includes, but is not limited to methylthio, ethylthio, n-propylthio, isopropylthio, n-butylthio, isobutylthio, and t-butylthio.

The term "cycloalkyl", as used herein, unless otherwise indicated, refers to cyclic hydrocarbon radicals including, but not limited to cyclopropyl, cyclopropyl, cyclobutyl, cyclopentyl and cyclohexyl.

The term "one or more substituents," as used herein, includes from one to the maximum number of substituents possible based on the number of available bonding sites.

Compounds of the formulae I, X, XI, XII, XIII, XIV, XV, XVI, XVII, XVIII, XIX, XX and XXI contain chiral centers and therefore exist in different enantiomeric forms. The above definitions of these compounds include all optical isomers and all stereoisomers of such compounds, and mixtures thereof.

DETAILED DESCRIPTION OF THE INVENTION

The compounds of the formulae Ia, Ib, Ic, Id, Ie, X, XI, XII, XIII, XIV, XV, XVI, XVII, XVIII, XIX, XX and XXI may be prepared as described below. Unless otherwise indicated, in the discussion that follows, structural formulae Ia, Ib, Ic, Id, Ie, X, XI XII, XIII, XIV, XV, XVI, XVII, XVIII, XIX, XX and XXI and groups II, III, IV, V, VI, VII, VIII and IX are defined as above.

Compounds of the formula Ia and Ib may be prepared as described in U.S. patent application Ser. No. 988,653, which was filed on Dec. 10, 1992. This application is incorporated herein by reference in its entirety. Compounds of the formula Ic may be prepared as described in U.S. patent application Ser. No. 932,292, which was filed on Aug. 19, 1992, and PCT Patent Application PCT/US 93/09407, which designates the United States and which was filed in the United States Receiving Office on Oct. 7, 1993 and published as WO 94/13663 on Jun. 23, 1994. These applications are incorporated herein by reference in their entirety.

Compounds of the formula Id may be prepared as described in PCT Patent Application PCT/US 92/03571, which designates the United States and which was filed in the United States Receiving Office on May 5, 1992 and published as WO 93/00331 on Jan. 7, 1993. This application is incorporated herein by reference in its entirety.

Compounds of the formula Ie may be prepared as described in U.S. patent application Ser. No. 123,306, which was filed on Sep. 17, 1993 and in PCT Patent Application PCT/IB 94/00221, which designates the United States and which was filed in the International Bureau on Jul. 18, 1994. This application is incorporated herein by reference in its entirety.

When $R^3$ is a group of the formula II, the starting materials of the formula $NH_2R^3$ that are used in the preparation of compounds of the formulae Ia, Ib, Ic, Id and Ie may be prepared as described in U.S. Pat. No. 5,162,339, which issued on Nov. 11, 1992. This patent is incorporated herein by reference in its entirety.

When $R^3$ is a group of the formula III, the starting materials of the formula $NH_2R^3$ that are used in the preparation of compounds of the formulae Ia, Ib, Ic, Id and Ie may be prepared as described in PCT Patent Application PCT/US 91/02853, which designates the United States, was filed in the United States Receiving Office on Apr. 25, 1991 and was published as WO 91/18899 on Dec. 12, 1991.

This application is incorporated herein by reference in its entirety.

When $R^3$ is a group of the formula IV, V or VI, the starting materials of the formula $NH_2R^3$ that are used in the preparation of compounds of the formulae Ia, Ib, Ic, Id and Ie may be prepared as described in PCT Patent Application PCT/US 91/03369, which designates the United States, was filed on in the United States Receiving Office May 14, 1991 and was published as WO 92/01688 on Feb. 6, 1992. This application is incorporated herein by reference in its entirety.

When $R^3$ is a group of the formula VII, the starting materials of the formula $NH_2R^3$ that are used in the preparation of compounds of the formulae Ia, Ib, Ic, Id and Ie may be prepared as described in U.S. Pat. No. 5,232,929, which issued on Aug. 3, 1993, U.S. patent application Ser. No. 800,667, filed Nov. 27, 1991, PCT Patent Application PCT/US 91/02541, which designates the United States, was filed in the United States Receiving Office on Apr. 12, 1991 and was published as WO 91/18878 on Dec. 12, 1991, and PCT Patent Application PCT/US 92/00065, which designates the United States, was filed in the United States Receiving Office on Jan. 14, 1992 and was published as WO 92/17449 on Oct. 15, 1992. These applications are incorporated herein by reference in their entirety.

When $R^3$ is a group of the formula VIII, the starting materials of the formula $NH_2R^3$ that are used in the preparation of compounds of the formulae Ia, Ib, Ic, Id and Ie may be prepared as described in PCT Patent Application PCT/US 91/05776, which designates the United States, was filed in the United States Receiving Office on Aug. 20, 1991 and was published as WO 92/06079 on Apr. 16, 1992, U.S. patent application Ser. No. 800,667, filed Nov. 27, 1991 and PCT Patent Application PCT/US 92/00065, which designates the United States, was filed in the United States Receiving Office on Jan. 14, 1992 and was published as WO 92/17449 on Oct. 15, 1992. These applications are incorporated herein by reference in their entirety.

When $R^3$ is a group of the formula IX, the starting materials of the formula $NH_2R^3$ that are used in the preparation of compounds of the formulae Ia, Ib, Ic, Id and Ie may be prepared as described in U.S. patent application Ser. No. 719,884, filed Jun. 21, 1991 and PCT Patent Application PCT/US 92/04697, which designates the United States and which was filed in the United States Receiving Office on Jun. 11, 1992 and published as WO 93/00330 on Jan. 7, 1993. These applications are incorporated herein by reference in their entirety.

Compounds of the formula X may be prepared as described in PCT Patent Application PCT/US 92/04002, which designates the United States, was filed in the United States Receiving Office on May 19, 1992 and was published as WO 92/15585 on Sep. 17, 1992. This application is incorporated herein by reference in its entirety.

Compounds of the formula XI may be prepared as described in PCT Patent Application PCT/US 92/04697, which designates the United States, and which was filed in the United States Receiving Office on Jun. 11, 1992 and published as WO 93/00330 on Jan. 7, 1993. This application is incorporated herein by reference in its entirety.

Compounds of the formula XII may be prepared as described in PCT Patent Application PCT/US 92/07730, which designates the United States and which was filed in the United States Receiving Office on Sep. 18, 1992 and published as WO 93/10073 on May 27, 1993. This application is incorporated herein by reference in its entirety.

Compounds of the formula XIII may be prepared as described in PCT Patent Application PCT/US 92/06819, which designates the United States and which was filed in the United States Receiving Office on Aug. 20, 1992 and published as WO 93/06099 on Apr. 1, 1993. This application is incorporated herein by reference in its entirety.

Compounds of the formula XIV may be prepared as described in U.S. patent application Ser. No. 885,110, which was filed on May 18, 1992 and in PCT Patent Application PCT/US 93/01429, which designates the United States and which was filed in the United States Receiving Office on Feb. 23, 1993 and published as WO 93/23380 on Nov. 25, 1993. These applications are incorporated herein by reference in their entirety.

Compounds of the formula XV may be prepared by the procedure described in PCT Patent Application PCT/US 92/04002, which designates the United States, was filed on May 19, 1992 and published as WO 92/20676 on Nov. 26, 1992. This application is incorporated herein by reference in its entirety.

Compounds of the formula XVI may be prepared as described in U.S. patent application Ser. No. 026,382, which was filed on Apr. 7, 1993, and PCT Patent Application PCT/US 93/11793, which designates the United States, and which was filed on Dec. 10, 1993 in the United States Receiving Office and published as WO 94/20500 on Sep. 15, 1994. These applications are incorporated herein by reference in their entirety.

Compounds of the formula XVII may be prepared as described in PCT Patent Application PCT/US 93/09169, which designates the United States and which was filed in the United States Receiving Office on Sep. 30, 1993 and published as WO 94/10170 on May 11, 1994. This application is incorporated herein by reference in its entirety.

Compounds of the formula XVIII may be prepared as described in PCT Patent Application PCT/US 93/09168, which designates the United States and which was filed in the United States Receiving Office on Sep. 30, 1993 and published as WO 94/08997 on Apr. 28, 1994. This application is incorporated herein by reference in its entirety.

Compounds of the formula XIX may be prepared as described in PCT Patent Application PCT/JP 94/00781, which designates the United States and which was filed in the Japanese Receiving Office on May 13, 1994. This application is incorporated herein by reference in its entirety.

Compounds of the formula XX may be prepared as described in PCT Patent Application PCT/JP 94/01092, which designates the United States and was filed in the Japanese Receiving Office on Jul. 5, 1994. This application is incorporated herein by reference in its entirety.

Compounds of the formula XXI may be prepared as described in PCT Patent Application PCT/JP 94/01514, which designates the United States and was filed in the Japanese Receiving Office on Sep. 13, 1994. This application is incorporated herein by reference in its entirety.

The compounds of the formulae Ia, Ib, Ic, Id, Ie, X, XI, XII, XIII, XIV, XV, XVI, XVII, XVIII and XIX (hereinafter referred to, collectively, as the "therapeutic agents") and the pharmaceutically acceptable salts thereof are useful as substance P receptor antagonists, i.e., they possess the ability to antagonize the effects of tachykinins at the substance P receptor site in mammals. They and other NK-1 antagonists are able to function as therapeutic agents in the treatment and prevention of stroke, epilepsy, head trauma, spinal cord trauma, ischemic neuronal damage such as cerebral ischemic damage from stroke or vascular occlusion (e.cf, during open heart surgery), excitotoxic neuronal damage (e.g., in stroke or epilepsy) and amyotrophic lateral sclerosis in mammals, including humans.

The therapeutic agents that are basic in nature are capable of forming a wide variety of different salts with various inorganic and organic acids. Examples of acids that form suitable pharmaceutically acceptable salts for use in this invention are those that form non-toxic acid addition salts, i.e., salts containing pharmacologically acceptable anions, such as the hydrochloride, hydrobromide, hydroiodide, nitrate, sulfate, bisulfate, phosphate, acid phosphate, acetate, lactate, citrate, acid citrate, tartrate, bitartrate, succinate, maleate, fumarate, gluconate, saccharate, benzoate, methanesulfonate, ethanesulfonate, benzenesulfonate, p-toluenesulfonate and pamoate [i.e., 1,1'-methylene-bis-(2-hydroxy-3-naphthoate)]salts.

Although such salts must be pharmaceutically acceptable for administration to animals, it is often desirable in practice to initially isolate a therapeutic agent from the reaction mixture as a pharmaceutically unacceptable salt and then simply convert the latter back to the free base compound by treatment with an alkaline reagent and subsequently convert the latter free base to a pharmaceutically acceptable acid addition salt. The acid addition salts of the base therapeutic agents of this invention are readily prepared by treating the base compound with a substantially equivalent amount of the chosen mineral or organic acid in an aqueous solvent medium or in a suitable organic solvent, such as methanol or ethanol. Upon careful evaporation of the solvent, the desired solid salt is readily obtained.

Those therapeutic agents of this invention that are also acidic in nature are capable of forming base salts with various pharmacologically acceptable cations. The chemical bases that are used as reagents to prepare the pharmaceutically acceptable base salts of the therapeutic agents are those that form non-toxic base salts with the acidic therapeutic agents. Such non-toxic base salts include those derived from such pharmacologically acceptable cations as sodium, potassium, calcium and magnesium, etc. These salts can easily be prepared by treating the corresponding acidic compounds with an aqueous solution containing the desired pharmacologically acceptable cations, and then evaporating the resulting solution to dryness, preferably under reduced pressure. Alternatively, they may also be prepared by mixing lower alkanolic solutions of the acidic compounds and the desired alkali metal alkoxide together, and then evaporating the resulting solution to dryness in the same manner as before. In either case, stoichiometric quantities of reagents are preferably employed in order to ensure completeness of reaction and maximum yields of the desired final product.

As indicated above, therapeutic agents and their pharmaceutically acceptable salts exhibit substance P receptor binding activity. They and other NK-1 antagonists are of value in the treatment and prevention of stroke, epilepsy, head trauma, spinal cord trauma, ischemic neuronal damage such as cerebral ischemic damage from stroke or vascular occlusion (e.g., during open heart surgery), excitotoxic neuronal damage (e.g., in stroke or epilepsy) and amyotrophic lateral sclerosis in mammals, including humans.

Other substance P receptor antagonists that are expected to exhibit activity for the treatment and prevention of the foregoing disorders in mammals, including humans, are those compounds described in the following references: European Patent Application EP 499,313, published Aug. 19, 1992; European Patent Application EP 520,555, published Dec. 30, 1992; European Patent Application EP 522,808, published Jan. 13, 1993, European Patent Application EP 528,495, published Feb. 24, 1993, PCT Patent Application WO 93/14084, published Jul. 22, 1993, PCT Patent Application WO 93/01169, published Jan. 21, 1993, PCT Patent Application WO 93/01165, published Jan. 21, 1993, PCT Patent Application WO 93/01159, published Jan. 21, 1993, PCT Patent Application WO 92/20661, published Nov. 26, 1992, European Patent Application EP 517,589, published Dec. 12, 1992, European Patent Application EP 428,434, published May 22, 1991, and European Patent Application EP 360,390, published Mar. 28, 1990.

The therapeutic agents and the pharmaceutically acceptable salts thereof, as well as other NK-1 antagonists, can be administered via either the oral, topical or parenteral routes. In general, these compounds are most desirably administered in dosages ranging from about 5.0 mg up to about 1500 mg per day, although variations will necessarily occur depending upon the weight and condition of the subject being treated and the particular route of administration chosen. However, a dosage level that is in the range of about 0.001 mg to about 21 mg per kg of body weight per day is most desirably employed. The preferred dosage for oral administration is from about 0.001 to about mg per kg of body weight per day. Ointments or eyedrops will preferably contain the active agent in a concentration of about 0.01 to about 5 percent, more preferably about 1%.

Variations may nevertheless occur depending upon the species of animal being treated and its individual response to said medicament, as well as on the type of pharmaceutical formulation chosen and the time period and interval at which such administration is carried out. In some instances, dosage levels below the lower limit of the aforesaid range may be more than adequate, while in other cases still larger doses may be employed without causing any harmful side effect, provided that such larger doses are first divided into several small doses for administration throughout the day.

The therapeutic agents, and their pharmaceutically acceptable salts, as well as other NK-1 antagonists may be administered alone or in combination with pharmaceutically acceptable carriers or diluents by either of the routes previously indicated, and such administration may be carried out in single or multiple doses. More particularly, the novel therapeutic agents of this invention can be administered in a wide variety of different dosage forms, i.e., they may be combined with various pharmaceutically acceptable inert carriers in the form of tablets, capsules, lozenges, troches, hard candies, suppositories, aqueous suspensions, injectable solutions, elixirs, syrups, and the like. Such carriers include solid diluents or fillers, sterile aqueous media and various non-toxic organic solvents, etc. Moreover, oral pharmaceutical compositions can be suitably sweetened and/or flavored. In general, the therapeutic compounds of this invention are present in such dosage forms at concentration levels ranging from about 5.0% to about 70% by weight.

For oral administration, tablets containing various excipients such as microcrystalline cellulose, sodium citrate, calcium carbonate, dicalcium phosphate and glycine may be employed along with various disintegrants such as starch (and preferably corn, potato or tapioca starch), alginic acid and certain complex silicates, together with granulation binders like polyvinylpyrrolidone, sucrose, gelatin and acacia. Additionally, lubricating agents such as magnesium stearate, sodium lauryl sulfate and talc are often very useful for tabletting purposes. Solid compositions of a similar type may also be employed as fillers in gelatin capsules; preferred materials in this connection also include lactose or milk sugar as well as high molecular weight polyethylene glycols.

When aqueous suspensions and/or elixirs are desired for oral administration, the active ingredient may be combined with various sweetening or flavoring agents, coloring matter or dyes, and, if so desired, emulsifying and/or suspending agents as well, together with such diluents as water, ethanol, propylene glycol, glycerin and various like combinations thereof.

For parenteral administration, solutions of a therapeutic agent in either sesame or peanut oil or in aqueous propylene glycol may be employed. The aqueous solutions should be suitably buffered if necessary and the liquid diluent first rendered isotonic. These aqueous solutions are suitable for intravenous injection purposes. The oily solutions are suitable for intraarticular, intramuscular and subcutaneous injection purposes. The preparation of all these solutions under sterile conditions is readily accomplished by standard pharmaceutical techniques well known to those skilled in the art.

The activity of the therapeutic agents as substance P receptor antagonists may be determined by their ability to inhibit the binding of substance P at its receptor sites in bovine caudate tissue, employing radioactive ligands to visualize the tachykinin receptors by means of autoradiography. The substance P antagonizing activity of the herein described compounds may be evaluated by using the standard assay procedure described by M. A. Cascieri et al., as reported in the *Journal of Biological Chemistry*, Vol. 258, p. 5158 (1983). This method essentially involves determining the concentration of the individual compound required to reduce by 50% the amount of radiolabelled substance P ligands at their receptor sites in said isolated cow tissues, thereby affording characteristic $IC_{50}$ values for each compound tested.

In this procedure, bovine caudate tissue is removed from a −70° C. freezer and homogenized in 50 volumes (w./v.) of an ice-cold 50 mM Tris (i.e., trimethamine which is 2-amino-2-hydroxymethyl-1,3-propanediol) hydrochloride buffer having a pH of 7.7. The homogenate is centrifuged at 30,000×G for a period of 20 minutes. The pellet is resuspended in 50 volumes of Tris buffer, rehomogenized and then recentrifuged at 30,000×G for another twenty-minute period. The pellet is then resuspended in 40 volumes of ice-cold 50 mM Tris buffer (pH 7.7) containing 2 mM of calcium chloride, 2 mM of magnesium chloride, 4 µg/ml of bacitracin, 44 g/ml of leupeptin, 24 g of chymostatin and 200 µg/ml of bovine serum albumin. This step completes the production of the tissue preparation.

The radioligand binding procedure is then carried out in the following manner, viz., by initiating the reaction via the addition of 100 µl of the test compound made up to a concentration of 1 µM, followed by the addition of 100 µl of radioactive ligand made up to a final concentration 0.5 mM and then finally by the addition of 800 µl of the tissue preparation produced as described above. The final volume is thus 1.0 ml, and the reaction mixture is next vortexed and incubated at room temperature (ca. 20° C.) for a period of 20 minutes. The tubes are then filtered using a cell harvester, and the glass fiber filters (Whatman GF/B) are washed four times with 50 mM of Tris buffer (pH 7.7), with the filters having previously been presoaked for a period of two hours prior to the filtering procedure. Radioactivity is then determined in a Beta counter at 53% counting efficiency, and the $IC_{50}$ values are calculated by using standard statistical methods.

What is claimed is:

1. A method of treating or preventing a disorder selected from stroke, epilepsy, head trauma, ischemic neuronal damage such as cerebral ischemic damage from stroke or vascular occlusion, excitotoxic neuronal damage and amyotrophic lateral sclerosis in a mammal, comprising administering to said mammal (a) an amount of a compound of the formula

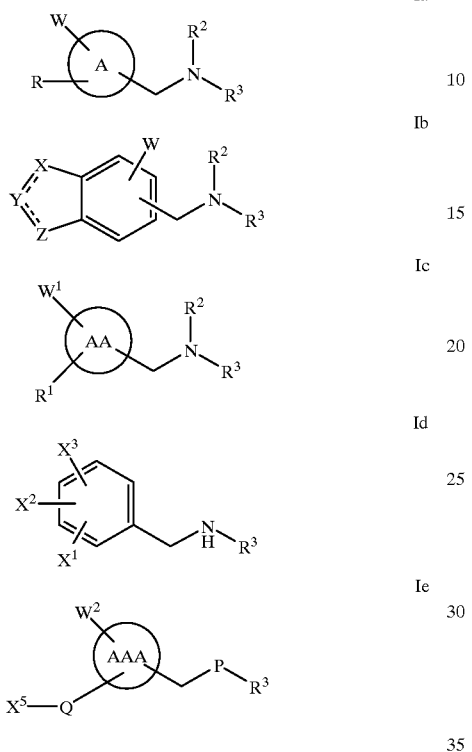

wherein A is a ring system selected from phenyl, naphthyl, thienyl, quinolinyl and indolinyl, and wherein the sidechain containing $NR^2R^3$ is attached to a carbon atom of ring system A;

A is an aryl group selected from phenyl, naphthyl, thienyl, dihydroquinolinyl and indolinyl, and wherein the sidechain containing $NR^2R^3$ is attached to a carbon atom of AA;

AAA is an aryl group selected from phenyl, naphthyl, thienyl, dihydroquinolinyl and indolinyl, and wherein the —$CH_2PR^3$ sidechain is attached to a carbon atom of ring AAA;

P is $NR^2$, O, S, SO or $SO_2$;

Q is $SO_2$, NH, —$N(C_1-C_6)$alkyl or

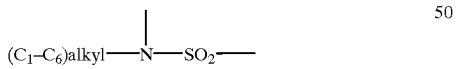

wherein the point of attachment of said

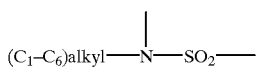

to ring AAA is the nitrogen atom and the point of attachment to $X^5$ is the sulfur atom;

$W^1$ is hydrogen, halo or $(C_1-C_6)$alkyl, S—$(C_1-C_3)$ alkyl, halo or $(C_1-C_6)$alkoxy optionally substituted with from one to three fluorine atoms;

$W^2$ is hydrogen, $(C_1-C_6)$alkyl, S—$(C_1-C_3)$alkyl, halo or $(C_1-C_6)$alkoxy optionally substituted with from one to three fluorine atoms;

W is hydrogen, $(C_1-C_6)$alkyl optionally substituted with from one to three fluorine atoms, —$S(O)_v$—$(C_1-C_6)$alkyl wherein v is zero, one or two, halo or $(C_1-C_6)$alkoxy optionally substituted with from one to three fluorine atoms;

$X^1$ is hydrogen, $(C_1-C_{10})$alkoxy optionally substituted with from one to three fluorine atoms or $(C_1-C_{10})$ alkyl optionally substituted with from one to three fluorine atoms;

$X^2$ and $X^3$ are independently selected from hydrogen, halo, nitro, $(C_1-C_{10})$alkyl optionally substituted with from one to three fluorine atoms, $(C_1-C_{10})$alkoxy optionally substituted with from one to three fluorine atoms, trifluoromethyl, hydroxy, phenyl, cyano, amino, $(C_1-C_6)$yalkylamino, di-$(C_1-C_6)$alkylamino, —(C=O)—NH—$(C_1-C_6)$alkyl, $(C_1-C_6)$-alkyl-(C=O)—NH—$(C_1-C_6)$alkyl, hydroxy$(C_1-C_4)$ alkyl, $C_1-C_4)$alkoxy$(C_1-C_4)$alkyl, —NHCHO and —NHCO—$(C_1-C_6)$alkyl;

$X^5$ is a four to six membered heterocyclic ring containing from one to three heteroatoms selected from sulfur, nitrogen and oxygen, wherein said heterocyclic ring may optionally be substituted with from one to three substituents, preferably with from zero to two substituents, independently selected from phenyl, $(C_1-C_6)$alkyl optionally substituted with from one to three fluorine atoms, $(C_1-C_6)$alkoxy optionally substituted with from one to three fluorine atoms and halo;

R is a 4, 5 or 6 membered heterocyclic ring containing from one to three heteroatoms selected from oxygen, nitrogen and sulfur wherein said heterocyclic ring may contain from zero to three double bonds and may optionally be substituted with one or more substituents, preferably one or two substituents, independently selected from $(C_1-C_6)$alkyl optionally substituted with from one to three fluorine atoms and $(C_1-C_6)$alkoxy optionally substituted with from one to three fluorine atoms;

$R^1$ is selected from amino, $(C_1-C_6)$alkylamino, di-$(C_1-C_6)$alkylamino, —$S(O)_v$—$(C_1-C_{10})$-alkyl wherein v is zero, one or two, —$S(O)_v$-aryl wherein v is zero, one or two, —O-aryl, —$SO_2NR^4R^5$ wherein each of $R^4$ and $R^5$ is, independently, $(C_1-C_6)$alkyl, or $R^4$ and $R^5$, together with the nitrogen to which they are attached, form a saturated ring containing one nitrogen and from 3 to 6 carbons, —NH(C=O)$(C_1-C_6)$alkyl, —NH(C=O)$CF_3$,

wherein one or both of the alkyl moieties may optionally be substituted with from one to three fluorine atoms, —$N(SO_2$—$(C_1-C_{10})$alkyl$)_2$ and

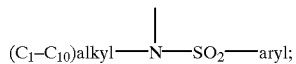

and wherein the aryl moieties of said —$S(O)_v$-aryl, —O-aryl and

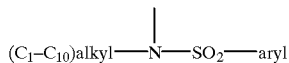

are independently selected from phenyl and benzyl and may optionally be substituted with from one to three substituents independently selected from $(C_1-C_4)$alkyl, $(C_1-C_4)$alkoxy and halo;
or $R^1$ is a group having the formula

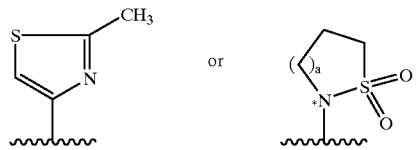

wherein a is 0, 1 or 2 and the asterisk represents a position meta to the $R^2R^3NCH_2$ side chain;

the dotted lines in formula Ib represent that one of the X—Y and Y—Z bonds may optionally be a double bond;

X is selected from =CH—, —CH$_2$—, —O—, —S—, —SO—, —SO$_2$—, —N(R$^4$)—, —NH—, =N—, —CH[(C$_1$-C$_6$)alkyl]—, =C[(C$_1$-C$_6$)alkyl]—, —CH(C$_6$H$_5$)— and =C(C$_6$H$_5$)—;

Y is selected from C=O, C=NR$^4$, C=S, =CH—, —CH$_2$—, =C[(C$_1$-C$_6$)alkyl]—, —CH[(C$_1$-C$_6$)alkyl]—, =C(C$_6$H$_5$Y, —CH(C$_6$H$_5$)—, =N—, —NH—, —N(R$^4$)—, =C(halo)—, =C(oR$^4$)—, =C(SR$^4$)—, =C(NR$^4$)—, —O—, —S—, and SO$_2$, wherein the phenyl moieties of said =C(C$_6$H$_5$)— and —CH(C$_6$H$_5$)— may optionally be substituted with from one to three substituents independently selected from trifluoromethyl and halo, and wherein the alkyl moieties of said =[(C$_1$-C$_6$)alkyl]— and —CH[C$_1$-C$_6$)alkyl]— may optionally be substituted with from one to three fluorine atoms;

Z is selected from =CH—, —CH$_2$—, =N—, —NH—, —S—, —N(R$^4$)—, =C(C$_6$H$_5$)—, —CH(C$_6$H$_5$)—, =C[(C$_1$-C$_6$) alkyl]— and —CH[(C$_1$-C$_6$) alkyl]—;

or X, Y and Z, together with the two carbon atoms shared between the benzo ring and the XYZ ring, form a fused pyridine or pyrimidine ring;

$R^4$ is $(C_1-C_6)$alkyl or phenyl;

$R^2$ is hydrogen or —CO$_2$(C$_1$-C$_{10}$)alkyl;

$R^3$ is selected from

II

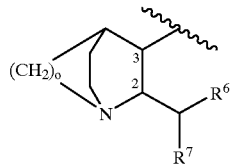

III

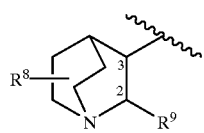

IV

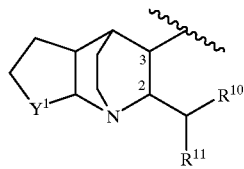

V

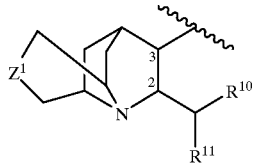

VI

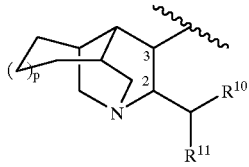

VII

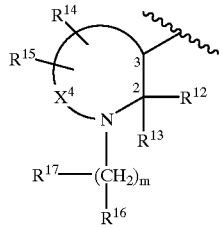

VIII

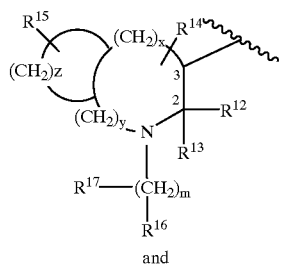

and

IX

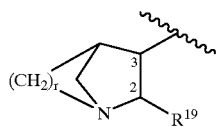

wherein $R^6$ and $R^{10}$ are independently selected from furyl, thienyl, pyridyl, indolyl, biphenyl and phenyl, wherein said phenyl may optionally be substituted with one or two substituents independently selected from halo, $(C_1-C_{10})$alkyl optionally substituted with from one to three fluorine atoms, $(C_1-C_{10})$alkoxy optionally substituted with from one to three fluorine atoms, carboxy, benzyloxycarbonyl and $(C_1-C_3)$ alkoxy-carbonyl;

$R^7$ is selected from $(C_3-C_4)$ branched alkyl, $(C_5-C_6)$ branched alkenyl, $(C_5-C_7)$cycloalkyl, a radicals named in the definition of $R^6$;

$R^8$ is hydrogen or $(C_1-C_6)$alkyl;

$R^9$ and $R^{19}$ are independently selected from phenyl, biphenyl, naphthyl, pyridyl, benzhydryl, thienyl and furyl, and $R^9$ and $R^{19}$ may optionally be substituted with from one to three substituents independently selected from halo, $(C_1-C_{10})$alkyl optionally substituted with from one to three fluorine atoms and $(C_1-C_{10})$alkoxy optionally substituted with from one to three fluorine atoms;

$Y^1$ is $(CH_2)_I$ wherein I is an integer from one to three, or $Y^1$ is a group of the formula

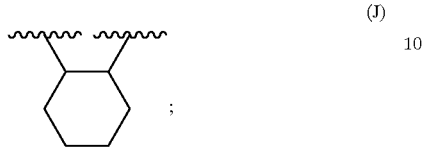

(J)

$Z^1$ is oxygen, sulfur, amino, $(C_1-C_3)$alkylamino or $(CH_2)_n$ wherein n is zero, one or two; x is an integer from zero to four;

y is an integer from zero to four;

z is an integer from one to six, wherein the ring containing $(CH_2)_z$ may contain from zero to three double bonds, and one of the carbons of $(CH_2)_z$ may optionally be replaced by oxygen, sulfur or nitrogen;

o is two or three;

p is zero or one;

r is one, two or three;

$R^{11}$ is thienyl, biphenyl or phenyl optionally substituted with one or two substituents independently selected from halo, $(C_1-C_{10})$alkyl optionally substituted with from one to three fluorine atoms and $(C_1-C_{10})$alkoxy optionally substituted with from one to three fluorine atoms;

$X^4$ is $(CH_2)_q$ wherein q is an integer from 1 to 6, and wherein any one of the carbon-carbon single bonds in said $(CH_2)_q$ may optionally be replaced by a carbon-carbon double bond, and wherein any one of the carbon atoms of said $(CH_2)_q$ may optionally be substituted with $R^{14}$, and wherein any one of the carbon atoms of said $(CH_2)_q$ may optionally be substituted with $R^{15}$;

m is an integer from 0 to 8, and any one of the carbon-carbon single bonds of $(CH_2)_m$, wherein both carbon atoms of such bond are bonded to each other and to another carbon atom in the $(CH_2)_m$ chain, may optionally be replaced by a carbon-carbon double bond or a carbon-carbon triple bond, and any one of the carbon atoms of said $(CH_2)_m$ may optionally be substituted with $R^{17}$;

$R^{12}$ is a radical selected from hydrogen, $(C_1-C_6)$ straight or branched alkyl, $(C_3-C_7)$cycloalkyl wherein one of the carbon atoms may optionally be replaced by nitrogen, oxygen or sulfur; aryl selected from biphenyl, phenyl, indanyl and naphthyl; heteroaryl selected from thienyl, furyl, pyridyl, thiazolyl, isothiazolyl, oxazolyl, isoxazolyl, triazolyl, tetrazolyl and quinolyl; phenyl-$(C_2-C_6)$alkyl, benzhydryl and benzyl, wherein the point of attachment on $R^{12}$ is a carbon atom unless $R^{12}$ is hydrogen, and wherein each of said aryl and heteroaryl groups and the phenyl moieties of said benzyl, phenyl-$(C_2-C_6)$alkyl and benzhydryl may optionally be substituted with one or more substituents independently selected from halo, nitro, $(C_1-C_{10})$alkyl optionally substituted with from one to three fluorine atoms, $(C_1-C_{10})$alkoxy optionally substituted with from one to three fluorine atoms, amino, hydroxy-$(C_1-C_6)$alkyl, $(C_1-C_6)$alkoxy-$(C_1-C_6)$alkyl, $(C_1-C_6)$-alkylamino, $(C_1-C_6)$alkyl-O—(C=O)—, $(C_1-C_6)$alkyl-O—(C=O)—$(C_1-C_6)$alkyl, $(C_1-C_6)$alkyl-(C=O)—O—, $(C_1-C_6)$alkyl-C—$(C_1-C_6)$alkyl-O—, $(C_1-C_6)$alkyl-(C=O)—, $(C_1-C_6)$alkyl-(C=O)—$(C_1-C_6)$alkyl-, di-$(C_1-C_6)$alkylamino, —(C=O)NH—$(C_1-C_6)$alkyl, $(C_1-C_6)$-alkyl-(C=O)—NH—$(C_1-C_6)$alkyl, —NH(CO)H and —NH(C=O)—$(C_1-C_6)$alkyl; and wherein one of the phenyl moieties of said benzhydryl may optionally be replaced by naphthyl, thienyl, furyl or pyridyl;

$R^{13}$ is hydrogen, phenyl or $(C_1-C_6)$alkyl;

or $R^{12}$ and $R^{13}$, together with the carbon to which they are attached, form a saturated carbocyclic ring having from 3 to 7 carbon atoms wherein one of said carbon atoms that is neither the point of attachment of the spiro ring nor adjacent to it may optionally be replaced by oxygen, nitrogen or sulfur;

$R^{14}$ and $R^{15}$ are each independently selected from hydrogen, hydroxy, halo, amino, oxo (=O), cyano, hydroxy-$(C_1-C_6)$alkyl, $(C_1-C_6)$alkoxy-$(C_1-C_6)$alkyl, $(C_1-C_6)$alkylamino, di-$(C_1-C_6)$alkylamino, $(C_1-C_6)$alkoxy, —(C=O)—OH, $(C_1-C_6)$alkyl-O—(C=O)—, $(C_1-C_6)$alkyl-O—(C=O)—$(C_1-C_6)$alkyl, $(C_1-C_6)$alkyl-(C=O)—O—, $(C_1-C_6)$alkyl-(C=O)—$(C_1-C_6)$alkyl-O—, $(C_1-C_6)$alkyl-(C=O)—, $(C_1-C_r)$alkyl-(C=O)—$(C_1-C_8)$alkyl-, and the radicals set forth in the definition of $R^{12}$;

$R^{16}$ is $NH(C=O)R^{18}$, $NHCH_2R^{18}$, $SO_2R^{18}$, $GR^{20}$ $CO_2H$ or one of the radicals set forth in any of the definitions of $R^{12}$, $R^{14}$ and $R^{15}$;

$R^{17}$ is oximino (=NOH) or one of the radicals set forth in any of the definitions of $R^{12}$, $R^{14}$ and $R^{15}$; and $R^{18}$ is $(C_1-C_6)$alkyl, hydrogen, phenyl or phenyl $(C_1-C_6)$alkyl;

G is selected from the group consisting of $CH_2$, nitrogen, oxygen, sulfur and carbonyl;

$R^{20}$ is a monocyclic or bicyclic heterocycle selected from the group consisting of pyrimidinyl, benzoxazolyl, 2,3-dihydro-3-oxobenzisosulfonazol-2-yl, morpholin-1-yl, thiomorpholin-1-yl, benzofuranyl, benzothienyl, indolyl, isoindolyl, isoquinolinyl, furyl, pyridyl, isothiazolyl, oxazolyl, triazolyl, tetrazolyl, quinolyl, thiazolyi, thienyl, and groups of the formulae

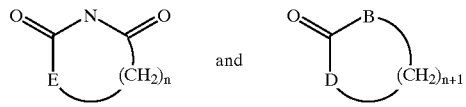

wherein B and D are selected from carbon, oxygen, and nitrogen, and at least one of B and D is other than carbon; E is carbon or nitrogen; n is an integer from 1 to 5; and any one of the carbons of the $(CH_2)_n$ or $(CH_2)_{n+1}$ may be optionally substituted with $(C_1-C_6)$alkyl or $(C_2-C_6)$spiroalkyl, and either any two of the carbon atoms of said $(CH_2)_n$ and $(CH_2)_{n+1}$ may be bridged by a one or two carbon atom linkage, or any one pair of adjacent carbons of said $(CH_2)_n$ and $(CH_2)_{n+1}$ may form, together with from one to three carbon atoms that are not members of the carbonyl containing ring, a $(C_3-C_5)$ fused carbocyclic ring;

with the proviso that (a) when m is 0, one of $R^{16}$ and $R^{17}$ is absent and the other is hydrogen, (b) when $R^3$ is a group of the formula Vil, $R^{14}$ and $R^{15}$ cannot be attached to the same carbon atom, (c) when $R^{14}$ and $R^{15}$ are attached to the same carbon atom, then either each of $R^{14}$ and $R^{15}$ is independently selected from hydrogen, fluoro, $(C_1-C_6)$alkyl, hydroxy-$(C_1-C_6)$alkyl and $(C_1-C_6)$alkoxy-$(C_1-C_6)$alkyl, or $R^{14}$ and $R^{15}$, together with the carbon to which they are attached, form a $(C_3-C_6)$ saturated carbocyclic ring that forms a spiro compound with the nitrogen-containing ring to which they are attached; (d) $R^{12}$ and $R^{13}$ cannot both be hydrogen; (e) when $R^{14}$ or $R^{15}$ is attached to a carbon atom of $X^4$ or $(CH_2)_y$ that is adjacent to the ring nitrogen, then $R^{14}$ or $R^{15}$, respectively, must be a substituent wherein the point of attachment is a carbon atom; and (f) neither $R^{14}$, $R^{15}$, $R^{16}$ nor $R^{17}$ can form a ring with $R^{13}$;

or a pharmaceutically acceptable salt thereof, that is effective in treating or preventing such disorder; or (b) an amount of a compound having the formula

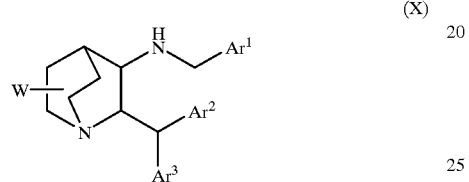

(X)

wherein W is Y or $X(CH_2)_n$;

Y is optionally substituted $(C_1-C_6)$alkyl, optionally substituted $(C_2-C_6)$alkenyl or optionally substituted $(C_3-C_8)$cycloalkyl;

X is optionally substituted $(C_1-C_6)$alkoxy, hydroxy, $CONR^1R_2$ $CO_2R^1$, $CHR^1OR^2$, $CHR^1NR^2R^3$, $COR^1$, $CONR^1OR^2$ or optionally substituted aryl or heteroaryl, wherein said aryl is selected from phenyl, naphthyl, and phenoxyphenyl, and wherein said heteroaryl is selected from pyridyl, quinolyl, thienyl, furyl, oxazolyl, tetrazolyl, thiazolyl, imidazolyl and pyrazolyl; and n is an integer from zero to six;

$Ar^1$, $Ar^2$ and $Ar^3$ are each, independently, optionally aryl or heteroaryl, wherein said aryl is selected from phenyl, naphthyl, and phenoxyphenyl, and wherein said heteroaryl is selected from pyridyl, quinolyl, thienyl, furyl, oxazolyl, tetrazolyl, thiazolyl, imidazolyl and pyrazolyl;

and $R^1$, $R^2$ and $R^3$ are independently selected from hydrogen, optionally substituted $(C_1-C_6)$alkyl, optionally substituted $(C_1-C_6)$alkoxy, optionally substituted $(C_3-C_8)$cycloalkyl, optionally substituted aryl or heteroaryl, wherein said aryl is selected from phenyl, naphthyl, and phenoxyphenyl, and wherein said heteroaryl is selected from pyridyl, quinolyl, thienyl, furyl, oxazolyl, tetrazolyl, thiazolyl, imidazolyl and pyrazolyl; and optionally substituted $(C_1-C_5)$heterocyclic groups, wherein said heterocyclic groups are selected from pyrrolidino, piperidino, morpholino, piperazinyl and thiamorpholino;

and wherein the substituents on the foregoing substituted alkyl, alkenyl, cycloalkyl and alkoxy groups are independently selected from halo, nitro, amino, $(C_1-C_4)$alkyl, $(C_1-C_4)$alkoxy, trifluoromethyl and trifluoromethoxy;

and wherein the substituents on the foregoing substituted $(C_1-C_5)$heterocyclic groups are attached to a sulfur or nitrogen atom on the ring and are independently selected from oxygen, di-oxygen and $(C_1-C_4)$ alkyl when attached to a ring sulfur atom, and are independently selected from oxygen and $(C_1-C_4)$ alkyl when attached to a ring nitrogen atom;

and wherein the substituents on said substituted aryl or heteroaryl in said $Ar^1$ groups are independently selected from $(C_1-C_6)$alkyl optionally substituted with from one to three halo groups; $(C_1-C_6)$alkoxy optionally substituted with from one to three halo groups; $(C_1-C_6)$alkylsulfinyl; $(C_2-C_6)$alkenyl; $(C_1-C_6)$alkylthio; $(C_1-C_6)$alkylsulfonyl; $(C_1-C_6)$alkylsulfonylamino; and di-$(C_1-C_6)$alkylamino wherein one or both of the alkyl groups may be optionally substituted with a $(C_1-C_6)$alkylsulfonyl, or $(C_1-C_6)$alkylsulfinyl group;

and wherein the substituents on said substituted aryl or heteroaryl in said $Ar^2$ and $Ar^3$ groups are independently selected from $(C_1-C_4)$alkyl, $(C_1-C_4)$alkoxy, $(C_1-C_4)$alkylthio, $(C_1-C_4)$alkylsulfinyl, di-$(C_1-C_4)$ alkylamino, trifluoromethyl and trifluoromethoxy; with the proviso that when Y is unsubstituted or is substituted with $(C_1-C_4)$alkyl, it is attached to the 4- or 6-position of the quinuclidine ring;

or a pharmaceutically acceptable salt thereof, that is effective in treating or preventing such disorder; or (c) A method of treating or preventing emesis in a mammal, comprising administering to said mammal an amount of a compound having the formula

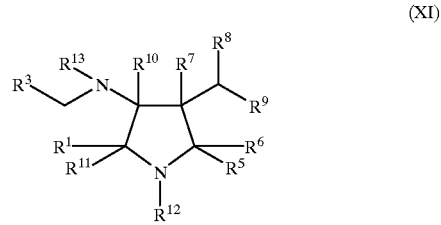

(XI)

wherein $R^1$ is selected from hydrogen, $(C_1-C_6)$ straight or branched alkyl, $(C_3-C_7)$cycloalkyl wherein one of the carbon atoms may optionally be replaced by nitrogen, oxygen or sulfur; aryl selected from phenyl, biphenyl, indanyl and naphthyl; heteroaryl selected from thienyl, furyl, pyridyl, thiazolyl, isothiazolyl, oxazolyl, isoxazolyl, triazolyl, tetrazolyl and quinolyl; phenyl $(C_2-C_6)$alkyl, benzhydryl and benzyl, wherein each of said aryl and heteroaryl groups and the phenyl moieties of said benzyl, phenyl $(C_2-C_6)$alkyl and benzhydryl may optionally be substituted with one or more substituents independently selected from halo, nitro, $(C_1-C_6)$alkyl optionally substituted with from one to three fluorine atoms, $(C_1-C_6)$alkoxy, amino, trihaloalkoxy, $(C_1-C_6)$alkylamino, $(C_1-C_6)$alkyl-O—(C=O)—, $(C_1-C_6)$alkyl-O—(C=O)—$(C_1-C_6)$alkyl, $(C_1-C_6)$alkyl-(C=O)—, $(C_1-C_6)$alkyl-(C=O)—, $(C_1-C_6)$alkyl-O—, $(C_1-C_6)$alkyl-(C=O)—, $(C_1-C_6)$ alkyl-(C=O)—, $(C_1-C_6)$alkyl-, di-$(C_1-C_6)$ alkylamino, —(C=O)NH—$(C_1-C_6)$alkyl, $(C_1-C_6)$ alkyl-(C=O)—NH—$(C_1-C_6)$alkyl-, —NH(C=O)H and —NH(C=O)—$(C_1-C_6)$alkyl; and wherein one of the phenyl moieties of said benzhydryl may optionally be replaced by naphthyl, thienyl, furyl or pyridyl;

$R^3$ is aryl selected from phenyl and naphthyl; heteroaryl selected from indanyl, thienyl, furyl, pyridyl, thiazolyl, isothiazolyl, oxazolyl, isoxazolyl, triazolyl, tetrazolyl and quinolyl; and cycloalkyl having 3 to 7 carbon atoms wherein one of said carbon atoms may optionally be replaced by nitrogen, oxygen or sulfur; wherein each of said aryl and heteroaryl groups may optionally be substituted with one or more substituents, and said $(C_3-C_7)$ cycloalkyl may optionally be substituted with one or two substituents, each of said substituents being independently selected from halo, nitro, $(C_1-C_6)$ alkyl optionally substituted with from one to three fluorine atoms, $(C_1-C_6)$alkoxy substituted with from one to three fluorine atoms, amino, phenyl, trihaloalkoxy, $(C_1-C_6)$alkylamino, —(C=O)—NH—$(C_1-C_6)$alkyl, $(C_1-C_6)$alkyl-(C=O), —(C=O)—$(C_1-C_6)$alkyl, —(C=O)H, —$CH_2OR^{13}$, $NH(C_1-C_6)$alkyl-, —NH(C=O)H, —$NR^{24}$(C=O)—$(C_1-C_6)$alkyl and —NH(C=O)—$(C_1-C_6)$alkyl;

one of $R^5$ and $R^6$ is hydrogen and the other is selected from hydroxymethyl, hydrogen, $(C_1-C_3)$alkyl, $(C_1-C_8)$acyloxy$(C_1-C_3)$alkyl, $(C_1-C_8)$alkoxymethyl and benzyloxymethyl;

$R^7$ and $R^8$ are independently selected from hydrogen, $(C_1-C_3)$alkyl and phenyl;

$R^9$ is selected from methyl, hydroxymethyl, H(C=O)—, $R^{14}R^{15}NCO_2CH_2$—, $R^{16}OCO_2CH_2$—, $(C_1-C_4)$alkyl-$CO_2CH_2$—, —$CONR^{17}$ $R^{18}$, $R^{17}R^{18}NCO_2$—, $R^{19}OCO_2$—, $C_6H_5CH_2$, $(C_1-C_4)$alkyl-CH(OH)—, $C_6H_5CH(OH)$—, $C_6H_5CH_2CH(OH)$—, $CH_2$halo, $R^{20}SO_2OCH_2$, —$CO_2R^{16}$ and $R^{21}CO_2$—, $R^{10}$ and $R^{11}$ are independently selected from hydrogen, $(C_1-C_3)$alkyl and phenyl;

$R^{12}$ is hydrogen, benzyl or a group of the formula

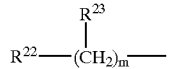

wherein m is an integer from zero to twelve, and any one of the carbon-carbon single bonds of $(CH_2)_m$, wherein both carbon atoms of such bond are bonded to each other and to another carbon atom of the $(CH_2)_m$ chain, may optionally be replaced by a carbon-carbon double or triple bond, and any one of the carbon atoms of $(CH_2)_m$ may optionally be substituted with $R^{23}$;

$R^{13}$, $R^{14}$, $R^{15}$, $R^{16}$, $R^{17}$, $R^{18}$, $R^{19}$, $R^{20}$, $R^{21}$ and $R^{24}$ are independently selected from hydrogen, $(C_1-C_3)$alkyl and phenyl;

$R^2$ and $R^{23}$ are independently selected from hydrogen, hydroxy, halo, amino, carboxy, carboxy$(C_1-C_6)$ alkyl, $(C_1-C_6)$alkylamino, di-$(C_1-C_6)$alkylamino, $(C_1-C_6)$alkoxy, $(C_1-C_6)$-alkyl-O—(C=O)—, $(C_1-C_6)$alkyl-O—(C=O)—$(C_1-C_6)$alkyl, $(C_1-C_6)$alkyl-(C=O)—, $(C_1-C_6)$alkyl-(C=O)—$(C_1-C_6)$alkyll-O—, $(C_1-C_6)$alkyl-(C=O)—, $(C_1-C_6)$-alkyl-(C=O)—$(C_1-C_6)$alkyl, $(C_1-C_6)$straight or branched alkyl, $(C_3-C_7)$cycloalkyl wherein one of the carbon atoms may optionally be replaced by nitrogen, oxygen or sulfur; aryl selected from phenyl and naphthyl; heteroaryl selected from indanyl, thienyl, furyl, pyridyl, thiazolyl, isothiazolyl, oxazolyl, isoxazolyl, triazolyl, tetrazolyl and quinolyl; phenyl-$(C_2-C_6)$alkyl, benzhydryl and benzyl, wherein each of said aryl and heteroaryl groups and the phenyl moieties of said benzyl, phenyl-$(C_2-C_6)$alkyl and benzhydryl may optionally be substituted with one or two substituents independently selected from halo, nitro, $(C_1-C_6)$alkyl optionally substituted with from one to three fluorine atoms, $(C_1-C_6)$alkoxy optionally substituted with from one to three fluorine atoms, trifluoromethyl, amino, $(C_1-C_6)$-alkylamino, $(C_1-C_6)$alkyl-O—(C=O), $(C_1-C_6)$alkyl-O—(C=O)—$(C_1-C_6)$alkyl, $(C_1-C_6)$alkyl $C_6$)alkyl-(C=O)—$(C_1-C_6)$alkyl-O—, $(C_1-C_6)$alkyl-(C=O)—, $(C_1-C_6)$alkyl-(C=O)—$(C_1-C_6)$alkyl-, di-$(C_1-C_6)$alkylamino, —(C=O)NH—$(C_1-C_6)$alkyl, $(C_1-C_6$yalkyl-(C=O)—NH—$(C_1-C_6)$alkyl, —NH(C=O)H and —NH(C=O)—$(C_1-C_6)$alkyl; and wherein one of the phenyl moieties of said benzhydryl may optionally be replaced by naphthyl, thienyl, furyl or pyridyl;

or $R^5$, together with the carbon to which it is attached, the nitrogen of the pyrrolidine ring, the carbon to which $R^7$ is attached and the carbon to which $R^5$ and $R^6$ are attached form a second pyrrolidine ring; with the proviso that when $R^9$, together with the carbon to which it is attached, the nitrogen of the pyrrolidine ring, the carbon to which $R^7$ is attached and the carbon to which $R^5$ and $R^6$ are attached, form a second pyrrolidine ring (thus forming a bicyclic structure containing a bridgehead nitrogen), either $R^{12}$ is absent or $R^{12}$ is present and the nitrogen of the second pyrrolidine ring is positively charged;

or a pharmaceutically acceptable salt thereof, that is effective in treating or preventing such disorder; or (d) an amount of a compound of the formula

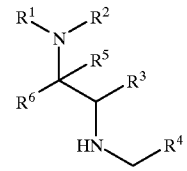

XII wherein $R^1$ is hydrogen, $(C_1-C_8)$alkyl, a saturated $(C_6-C_{10})$carbocyclic ring system containing two fused rings, a saturated $(C_6-C_{10})$carbocyclic bridged ring system containing two rings, or benzyl wherein the phenyl moiety of said benzyl may optionally be substituted with one or more substituents independently selected from halo, $(C_1-C_6)$alkyl optionally substituted with from one to three fluorine atoms and $(C_1-C_8)$ alkoxy optionally substituted with from one to three fluorine atoms;

$R^2$ is hydrogen, benzyl or a group of the formula

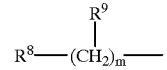

wherein m is an integer from zero to twelve, and any one of the carbon-carbon single bonds of $(CH_2)_m$, wherein both carbon atoms of such bond are bonded to each other and to another carbon atom of the $(CH_2)_m$ chain, may optionally be replaced by a carbon-carbon double or triple bond, and any one of the carbon atoms of $(CH_2)_m$ may optionally be substituted with $R^9$;

$R^8$ and $R^9$ are independently selected from hydrogen, hydroxy, halo, amino, carboxy, carboxy$(C_1-C_6)$ alkyl, $(C_1-C_6)$alkylamino, di-$(C_1-C_6)$alkytamino, $(C_1-C_6)$alkoxy, $(C_1-C_6)$alkyl-O—(C=O)—, (C₁–C₆)alkyl-O—(C=O)—(C₁–C₆)alkyl-O—(C₁–C₆)alkyl-(C=O)—O—, (C₁–C₆)alkyl-(C=O)—(C₁–C₆)alkyl-O—, (C₁–C₆)alkyl-(C=O)—, (C₁–C₆) straight or branched alkyl, (C₃–C₇)cycloalkyl wherein one of the carbon atoms may optionally be replaced by nitrogen, oxygen or sulfur; aryl selected from phenyl and naphthyl; heteroaryl selected from indanyl, thienyl, furyl, pyridyl, thiazolyl, isothiazolyl, oxazolyl, isoxazolyl, triazolyl, tetrazolyl and quinolyl; phenyl-(C₂-Cr) alkyl, benzhydryl and benzyl, wherein each of said aryl and heteroaryl groups and the phenyl moieties of said benzyl, phenyl-(C₂–C₆)alkyl and benzhydryl may optionally be substituted with one or two substituents independently selected from halo, nitro, (C₁–C₆)alkyl optionally substituted with from one to three fluorine atoms, (C₁–C₆)alkoxy optionally substituted with from one to three fluorine atoms, trifluoromethyl, amino, (C₁–C₆)-alkylamino, (C₁–C₆)alkyl-O—(C=O)—, (C₁–C₆)alkyl-O—(C=O)—(C₁–C₆)alkyl-, (C₁–C₆)alkyl-(C=O)—O—, (C₁–C₆)alkyl-(C=O)—(C₁–C₆)alkyl-O (C₁–C₆)alkyl-(C=O)—, (C₁–C₆)alkyl-(C=O)—(C₁–C₆)alkyl-, di-(C₁–C₆)alkylamino, —(C=O)NH—(C₁–C₆)-, alkyl-(C=O)—NH(C₁–C₆)alkyl, —NH(C=O)H and —NH(C=O)—(C₁–C₆)alkyl; and wherein one of the phenyl moieties of said benzhydryl may optionally be replaced by naphthyl, thienyl, furyl or pyridyl;

or R¹ and R², together with the nitrogen to which they are attached, form a saturated or unsaturated monocyclic ring containing from three to eight carbon atoms, a fused bicyclic ring containing from six to ten carbon atoms, or a saturated bridged ring system containing from six to ten carbon atoms;

R⁴ is aryl selected from phenyl and naphthyl; heteroaryl selected from indanyl, thienyl, furyl, pyridyl, thiazolyl, isothiazolyl, oxazolyl, isoxazolyl, triazolyl, tetrazolyl and quinolyl; and cycloalkyl having from three to seven carbon atoms wherein one of said carbon atoms may optionally be replaced by nitrogen, oxygen or sulfur; wherein each of said aryl and heteroaryl groups may optionally be substituted with one or more substituents, and said (C₃–C₇)cycloalkyl may optionally be substituted with one, two or three substituents, each of said substituents being independently selected from halo, nitro, (C₁–C₆)alkyl optionally substituted with from one to three fluorine atoms, (C₁–C₆)alkoxy optionally substituted with from one to three fluorine atoms, phenyl, amino, (C₁–C₆)alkylamino, —(C=O)—NH—(C₁–C₆)alkyl, (C₁–C₆)alkyl-(C=O)—, —(C=O)—O—(C₁–C₆)alkyl, —(C=O)H, —CH₂OR¹², NH₂(C₁–C₆)alkyl-, —NH(C=O)H, —NH(C=OY(C₁–C₆)alkyl, —NH—(S=O)—(C₁–C₆)alkyl and (C₁–C₆)alkyl—N—(SO₂)—(C₁–C₆)alkyl-, R³ is hydrogen, (C₃–C₈)cycloalkyl, (C₁–C₆) straight or branched alkyl or phenyl optionally substituted with one or more substituents independently selected from halo, (C₁–C₆)alkyl optionally substituted with from one to three fluorine atoms, and (C₁–C₆)alkoxy optionally substituted with from one to three fluorine atoms;

R⁵ is hydrogen, (C₁–C₆)alkyl, or phenyl optionally substituted with one or more substituents independently selected from halo, (C₁–C₆)alkyl optionally substituted with from one to three fluorine atoms and (C₁–C₆)alkoxy optionally substituted with from one to three fluorine atoms;

R⁶ is selected from hydrogen, (C₁–C₆) straight or branched alkyl, (C₃–C₇)cycloalkyl wherein one of the carbon atoms may optionally be replaced by nitrogen, oxygen or sulfur; aryl selected from phenyl, biphenyl, indanyl and naphthyl; heteroaryl selected from thienyl, furyl, pyridyl, thiazolyl, isothiazolyl, oxazolyl, isoxazolyl, triazolyl, tetrazolyl and quinolyl; phenyl (C₂–C₆)alkyl, benzhydryl and benzyl, wherein each of said aryl and heteroaryl groups and the phenyl moieties of said benzyl, phenyl (C₂–C₆)alkyl and benzhydryl may optionally be substituted with one or more substituents independently selected from halo, nitro, (C₁–C₆)alkyl optionally substituted with from one to three fluorine atoms, (C₁–C₆)alkoxy, trifluoromethyl, amino, trihaloalkoxy (e.g., trifluoromethoxy), (C₁–C₆) alkylamino, (C₁–C₆)alkyl-O—(C=O)—, (C₁–C₆) alkyl-O—(C=O)—(C₁–C₆)alkyl, (C₁–C₆)alkyl-(C=O)—O—, (C₁–C₆)alkyl-(C=O)(C₁–C₆)alkyl-O—, (C₁–C₆)alkyl-(C=O)—, (C₁–C₆)alkyl-(C=OY(C₁–C₆)alkyl-, di-(C₁–C₆)alkylamino, —(C=O)NH—(C₁–C₆)alkyl, (C₁–C₆)alkyl-(C=O)—NH—(C₁–C₆)alkyl-, —NH(C=O)H and —NH(C=O)—(C₁–C₆)alkyl; and wherein one of the phenyl moieties of said benzhydryl may optionally be replaced by naphthyl, thienyl, furyl or pyridyl; and R¹² is hydrogen, (C₁–C₃)alkyl or phenyl;

or a pharmaceutically acceptable salt thereof, that is effective in treating or preventing such disorder;

(e) an amount of a compound of the formula

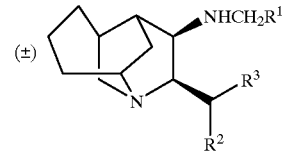

XIII wherein R¹ is cycloalkyl having from five to seven carbon atoms, pyrrolyl, thienyl, pyridyl, phenyl or substituted phenyl, wherein said substituted phenyl is substituted with from one to three substituents independently selected from fluorine, chlorine, bromine, trifluoromethyl, alkyl having from one to three carbon atoms, alkoxy having from one to three carbon atoms, carboxy, alkoxycarbonyl having from one to three carbon atoms in the alkoxy moiety and benzyloxycarbonyl;

R² is furyl, thienyl, pyridyl, indolyl, biphenyl, phenyl or substituted phenyl, wherein said substituted phenyt is substituted with one or two substituents independently selected from fluorine, chlorine, bromine, trifluoromethyl, alkyl having from one to three carbon atoms, alkoxy having from one to three carbon atoms, carboxy, alkoxycarbonyl having from one to three carbon atoms in the alkoxy moiety and benzyloxycarbonyl; and R³ is thienyl, phenyl, fluorophenyl, chlorophenyl or bromophenyl;

or a pharmaceutically acceptable salt thereof, that is effective in treating or preventing such disorder; or (f) an amount of a compound of the formula

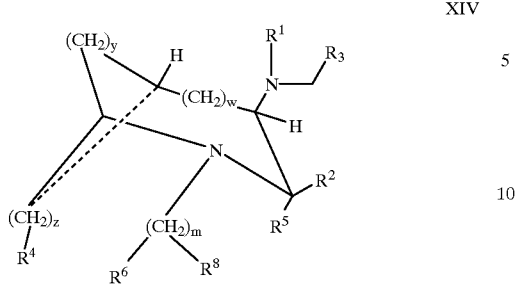

XIV wherein m is an integer from 0 to 8, and any one of the carbon-carbon single bonds of $(CH_2)_m$, wherein both carbon atoms of such bond are bonded to each other and to another carbon in the $(CH_2)_m$ chain, may optionally be replaced by a carbon-carbon double bond or a carbon-carbon triple bond, and any one of the carbon atoms of said $(CH_2)_m$ may optionally be substituted with $R^8$;

w is an integer from 0 to 2;
y is an integer from 1 to 4;
z is an integer from 1 to 4, and wherein any one of the carbon atoms of said $(CH_2)_z$ may optionally be substituted with $R^4$;
$R^1$ is hydrogen or $(C_1-C_8)$alkyl optionally substituted with hydroxy, alkoxy or fluoro;
$R^2$ is a group selected from hydrogen, $(C_1-C_6)$straight or branched alkyl, $(C_3-C_7)$cycloalkyl wherein one of the carbon atoms may optionally be replaced by nitrogen, oxygen or sulfur; aryl selected from phenyl, indanyl, and naphthyl; heteroaryl selected from thienyl, furyl, pyridyl, thiazolyl, isothiazolyl, oxazolyl, isoxazolyl, triazolyl, tetrazolyl and quinolyl; phenyl$(C_2-C_6)$alkyl, benzhydryl and benzyl, wherein one of the phenyl moieties of said benzhydryl may optionally be replaced by naphthyl, thienyl, furyt or pyridyl and wherein each of said aryl and heteroaryl groups and the phenyl moieties of said benzyl, phenyl$(C_2-C_6)$alkyl and benzhydryl may optionally be substituted with one or more substituents independently selected from halo, nitro, $(C_1-C_6)$alkyl, $(C_1-C_6)$alkoxy, trifluoromethyl, amino, $(C_1-C_6y$alkylamino, $(C_1-C_6)$alkyl-O—(C=O)—, $(C_1-C_6)$alkyl-O—(C=O)—$(C_1-C_6)$alkyl, $(C_1-C_6)$-(C=O)—O—, $(C_1-C_6)$alkyl-(C=O)—$(C_1-C_6)$alkyl-O—, $(C_1-C_6)$alkyl-(C=O)—, $(C_1-C_6)$alkyl-(C=O)— $(C_1-C_6)$alkyl-, di-$(C_1-C_6)$alkylamino, —(C=O)NH—$(C_1-C_6)$alkyl,$(C_1-C_6)$-alkyl-(C=O)—NH—$(C_1-C_6)$alkyl, —NH(C=O)H and —NH(C=O)—$(C_1-C_6)$alkyl;
$R^5$ is hydrogen, phenyl or $(C_1-C_6)$alkyl;
or $R^2$ and $R^5$, together with the carbon to which they are attached, form a saturated carbocyclic ring having from 3 to 7 carbon atoms wherein one of said carbon atoms may optionally be replaced by oxygen, nitrogen or sulfur;
$R^3$ is aryl selected from phenyl, indanyl, and naphthyl; heteroaryl selected from thienyl, furyl, pyridyl, thiazolyl, isothiazolyl, oxazolyl, isoxazolyl, triazolyl, tetrazolyl and quinolyl; and cycloalkyl having 3 to 7 carbon atoms wherein one of said carbon atoms may optionally be replaced by nitrogen, oxygen or sulfur; wherein each of said aryl and heteroaryl groups may optionally be substituted with one or more substituents, and said $(C_3-C_7)$ cycloalkyl may optionally be substituted with one or two substituents, each of said substituents being independently selected from halo, nitro, $(C_1-C_6)$ alkyl optionally substituted with from one to three fluorine atoms, $(C_1-C_6)$alkoxy optionally substituted with from one to three fluorine atoms, trifluoromethyl, phenyl, amino, $(C_1-C_6)$alkylamino, $(C_1-C_6)$dialkyl amino, —(C=O)—NH—$(C_1-C_6)$ alkyl, $(C_1-C_6)$alkyl-(C=O)—NH—$(C_1-C_6)$alkyl, —NH(C=O)H and —NH(C=O)—$(C_1-C_6)$alkyl;
$R^4$ is independently selected from hydrogen, hydroxy, halo, amino, oxo (=O), nitrile, $(C_1-C_6)$ alkylamino, di-$(C_1-C_6)$alkylamino, $(C_1-C_6)$alkoxy, $(C_1-C_6)$alkyl-O—(C=O)—, $(C_1-C_6)$alkyl-O—(C=O)—$(C_1-C_6)$alkyl, $(C_1-C_6)$alkyl-(C=O)—O—, $(C_1-C_6)$alkyl-(C=O)$(C_1-C_6)$alkyl-O—, hydroxy-$(C_1-C_6)$alkyl, $(C_1-C_6)$alkoxy$(C_1-C_6)$alkyl, $(C_1-C_6)$alkyl-(C=O)—, $(C_1-C_6)$alkyl-(C=O)—$(C_1-C_6)$alkyl-, and the groups set forth in the definition of $R^2$;
$R^6$ is $NH(C=O)R^9$, $NHCH_2R^9$, $NHSO_2R^9$ or one of the groups set forth in any of the definitions of $R^2$, and $R^4$;
$R^8$ is oximino (=NOH) or one of the groups set forth in any of the definitions of $R^2$, and $R^4$;
$R^9$ is $(C_1-C_6)$alkyl, hydrogen, phenyl or phenyl $(C_1-C_6)$alkyl;
with the proviso that (a) when m is 0, $R^8$ is absent and $R^6$ is hydrogen, (b) neither $R^4$, $R^6$, nor $R^8$ can form, together with the carbon to which it is attached, a ring with $R^5$, and (c) the sum of y and z must be less than 7;
or a pharmaceutically acceptable salt thereof, that is effective in treating or preventing such disorder; or
(g) an amount of a compound of the formula

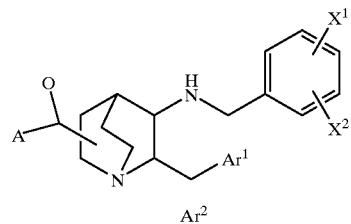

XV wherein $X^1$ is $(C_1-C_5)$alkoxy or halosubstituted $(C_1-C_5)$alkoxy;
$X^2$ is hydrogen, halogen, $(C_1-C_5)$alkyl, $(C_2-C_5)$ alkenyl, $(C_2-C_5)$alkynyl, $(C_1-C_5)$alkoxy, $(C_1-C_5)$ alkylthio, $(C_1-C_5)$alkylsulfinyl, $(C_1-C_5)$ alkylsulfonyl, halosubstituted $(C_1-C_5)$alkyl, halosubstituted $(C_1-C_5)$alkoxy, $(C_1-C_5)$alkylamino, dialkylamino having from 1 to 5 carbon atoms in each alkyl moiety, $(C_1-C_5)$alkylsulfonylamino (which may be substituted by halogen),

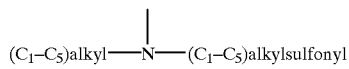

(which may be substituted by halogen in the alkylsulfonyl moiety), $(C_1-C_5)$alkanoylamino (which may be substituted by halogen) or

(which may be substituted by halogen in the alkanoyl moiety); $Ar^1$ and $Ar^2$ are each, independently, thienyl, phenyl, fluorophenyt, chlorophenyl or bromophenyl;

A is $Y-(CH_2)_m-CH(R^2)-(CH_2)_n-NR^1-$;

$R^1$ is hydrogen, $(C_1-C_5)$alkyl, benzyl or $-(CH_2)_p-Y$;

$R^2$ is hydrogen, $(C_1-C_5)$alkyl (which may be substituted by a substituent selected from the group consisting of hydroxy, amino, methylthio and mercapto), benzyl, 4-hydroxybenzyl, 3-indolylmethyl or $-(CH_2)_p-Y$;

Y is $-CN$, $-CH_2Z$ or $-COZ$;

Z is hydroxy, amino, $(C_1-C_5)$alkoxy, $(C_1-C_5)$ alkylamino or dialkylamino having from 1 to 5 carbon atoms in each alkyl moiety;

m, n and p are each, independently, 0, 1, 2 or 3; and $R^1$ and $R^2$ may be connected to form a ring;

or a pharmaceutically acceptable salt thereof, that is effective in treating or preventing such disorder; or (h) an amount of a compound of the formula

XVI

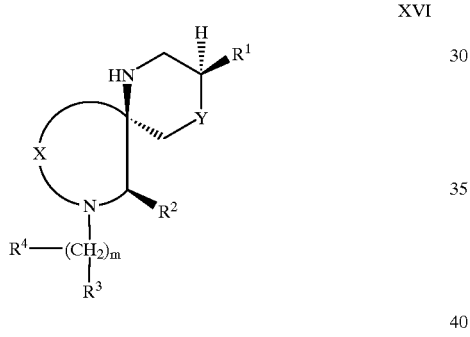

wherein $R^1$ is phenyl optionally substituted with one or more substituents, preferably with from one to three substituents, independently selected from hydrogen, halo, nitro, $(C_1-C_{10})$alkyl optionally substituted with from one to three fluorine atoms, $(C_1-C_{10})$alkoxy optionally substituted with from one to three fluorine atoms, trifluoromethyl, hydroxy, phenyl, cyano, amino, $(C_1-C_6)$-alkylamino, di-$(C_1-C_6)$alkylamino, $-(C=O)-NH-(C_1-C_6)$alkyl, $(C_1-C_6)$alkyl-$(C=O)-NH-(C_1-C_6)$alkyl, hydroxy$(C_1-C_4)$alkyl, $-NH(C=O)H$, $-NH(C=O)-(C_1-C_6)$alkyl, $(C_1-C_4)$alkoxy$(C_1-C_4)$alkyl, $-S(O)_v-(C_1-C_{10})$alkyl wherein v is zero, one or two, $-S(O)_v$-aryl wherein v is zero, one or two, $-O$-aryl, $-SO_2NR^4R^5$ wherein each of $R^4$ and $R^5$ is independently, $(C_1-C_6)$alkyl, or $R^4$ and $R^5$, together with the nitrogen to which they are attached, form a saturated ring containing one nitrogen and from 3 to 6 carbons,

wherein one or both of the alkyl moieties may optionally be substituted with from one to three fluorine atoms, $-N(SO_2-(C_1-C_{10})$alkyl$)_2$ and

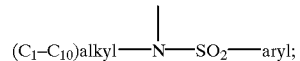

and wherein the aryl moieties of said $-S(O)_v$-aryl, $-O$-aryl and

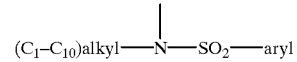

are independently selected from phenyl and benzyl and may optionally be substituted with from one to three substituents independently selected from $(C_1-C_4)$alkyl, $(C_1-C_4)$alkoxy and halo;

or $R^1$ is phenyl substituted with a group having the formula

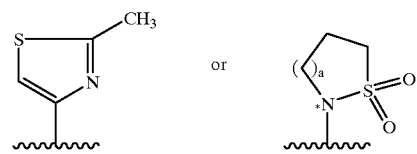

wherein a is 0, 1 or 2 and the asterisk represents a position meta to the point of attachment of $R^1$;

$R^2$ is selected from $(C_1-C_6)$ straight or branched alkyl, $(C_3-C_7)$cycloalkyl wherein one of the carbon atoms may optionally be replaced by nitrogen, oxygen or sulfur; aryl selected from biphenyl, phenyl, indanyl and naphthyl; heteroaryl selected from thienyl, furyl, pyridyl, thiazolyl, isothiazolyl, oxazolyl, isoxazolyl, triazolyl, tetrazolyl and quinolyl; phenyl $(C_2-C_6)$ alkyl, benzhydryl and benzyl, wherein each of said aryl and heteroaryl groups and the phenyl moieties of said benzyl, phenyl $(C_2-C_6)$alkyl and benzhydryl may optionally be substituted with one or more substituents, preferably with from one to three substituents, independently selected from halo, nitro, $(C_1-C_{10})$alkyl optionally substituted with from one to three fluorine atoms, $(C_1-C_{10})$alkoxy optionally substituted with from one to three fluorine atoms, amino, hydroxy-$(C_1-C_6)$alkyl, $(C_1-C_6)$alkoxy-$(C_1-C_6)$alkyl, $(C_1-C_6)$-alkylamino, $(C_1-C_6)$alkyl-$O-(C=O)-$, $(C_1-C_6)$alkyl-$O-(C=O)-(C_1-C_6)$ alkyl, $(C_1-C_6)$alkyl-$(C=O)-O-$, $(C_1-C_6)$alkyl-$(C=O)-(C_1-C_6)$alkyl-$O-$, $(C_1-C_6)$alkyl-$(C=O)-$, $(C_1-C_6)$alkyl-$(C=O)-(C_1-C_6)$alkyl-, di-$(C_1-C_6)$alkylamino, $-(C=O)NH(C_1-C_6)$alkyl, $(C_1-C_6)$-alkyl-$(C=O)-NH-(C_1-C_6)$alkyl, $-NH(C=O)H$ and $-NH(C=O)-(C_1-C_6)$alkyl; and wherein one of the phenyl moieties of said benzhydryl may optionally be replaced by naphthyl, thienyl, furyl or pyridyl;

m is an integer from 0 to 8, and any one of the carbon-carbon single bonds of $(CH_2)_m$, wherein both carbon atoms of such bond are bonded to each other and to another carbon atom in the $(CH_2)_m$ chain, may optionally be replaced by a carbon-carbon double bond or a carbon-carbon triple bond, and any one of the carbon atoms of said $(CH_2)_m$ may optionally be substituted with $R^4$;

$R^3$ is selected from $NH(C=O)R^8$, $NHCH_2R^8$, $SO_2R^8$, $AR^9$, $CO_2H$ and the radicals set forth in the definitions of $R^2$, $R^6$ and $R^7$;

A is $CH_2$, nitrogen, oxygen, sulfur or carbonyl;

$R^8$ is $(C_1-C_6)$alkyl, hydrogen, phenyl or phenyl $(C_1-C_6)$alkyl;

$R^4$ is selected from oximino (=NOH) and the radicals set forth in the definitions of $R^2$, $R^6$ and $R^7$;

$R^9$ is a monocyclic or bicyclic heterocycle selected from the group consisting of pyrimidinyl, benzoxazolyl, 2,3-dihydro-3-oxobenzisosulfonazol-2-yl, morpholin-1-yl, thiomorpholin-1-yl, benzofuranyl, benzothienyl, indolyl, isoindolyl, isoquinolinyl, furyl, pyridyl, isothiazolyl, oxazolyl, triazolyl, tetrazolyl, quinolyl, thiazolyl, thienyl, and groups of the formulae

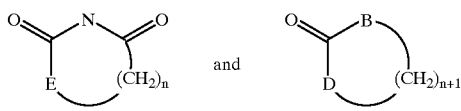

and wherein B and D are selected from carbon, oxygen and nitrogen, and at least one of B and D is other than carbon; E is carbon or nitrogen; n is an integer from 1 to 5; any one of the carbon atoms of said $(CH_2)_n$ and $(CH_2)_{n+1}$ may be optionally substituted with $(C_1-C_6)$alkyl or $(C_2-C_6)$spiroalkyl; and either any and either any one pair of the carbon atoms of said $(CH_2)_n$ and $(CH_2)_{n+1}$ may be bridged by a one or two carbon atom linkage, or any one pair of adjacent carbon atoms of said $(CH_2)_n$ and $(CH_2)l+_1$ may form, together with from one to three carbon atoms that are not members of the carbonyl containing ring, a $(C_3-C_5)$ fused carbocyclic ring;

X is $(CH_2)_q$ wherein q is two or three and wherein one of the carbon-carbon single bonds in said $(CH_2)_q$ may optionally be replaced by a carbon-carbon double bond, and wherein any one of the carbon atoms of said $(CH_2)_q$ may optionally be substituted with $R^6$, and wherein any one of the carbon atoms of said $(CH_2)_q$ may optionally be substituted with $R^7$;

$R^6$ and $R^7$ are independently selected from hydrogen, hydroxy, halo, amino, oxo (=O), cyano, hydroxy-$(C_1-C_6)$alkyl, $(C_1-C_6)$alkoxy-$(C_1-C_6)$alkyl, $(C_1-C_6)$alkylamino, di-$(C_1-C_6)$alkoxy, —(C=O)—OH, $(C_1-C_6)$alkyl-O—(C=O)—, $(C_1-C_6)$alkyl-O—(C=O)—$(C_1-C_6)$alkyl, $(C_1-C_6)$alkyl-(C=O)—O—, $(C_1-C_6)$alkyl-(C=O)—$(C_1-C_6)$alkyl-O—, $(C_1-C_6)$alkyl-(C=O)—, $(C_1-C_6)$alkyl-(C=O)—$(C_1-C_6)$alkyl- and the radicals set forth in the definition of $R^2$; and Y is $(CH_2)_z$ wherein z is zero or one;

with the proviso that: (a) when A is —(CH_2)— or carbonyl, $R^9$ cannot be furyl, pyridyl, isothiazolyl, oxazolyl, triazolyl, tetrazolyl, quinolyl, thiazolyl or thienyl; (b) when m is zero, one of $R^3$ and $R^4$ is absent and the other is hydrogen; and (c) when $R^6$ or $R^7$ is attached to a carbon atom of X that is adjacent to the ring nitrogen, then $R^6$ or $R^7$, respectively, must be a substituent wherein the point of attachment is a carbon atom;

or a pharmaceutically acceptable salt thereof, that is effective in treating or preventing such disorder; or (i) an amount of a compound of the formula

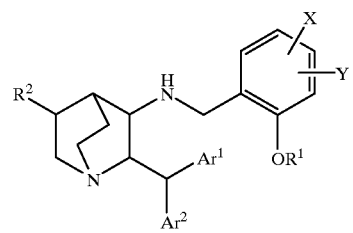

XVII wherein $Ar^1$ and $Ar^2$ are each independently phenyl;
$R^1$ is alkyl having from 1 to 6 carbon atoms;
$R^2$ is hydrogen or alkyl having from 1 to 6 carbon atoms;
and either X and Y are taken separately and they are each, independently, hydrogen, dialkylphosphoryl having from 2 to 12 carbon atoms, alkyl having from 1 to 6 carbon atoms; or X and Y are taken together and they represent a hydrocarbon chain having 3, 4, or 5 carbon atoms, optionally containing up to 2 double bonds and optionally having 1 or 2 substituents selected from oxo, hydroxy and alkyl having from 1 to 6 carbon atoms;
provided that when X and Y are taken together they are attached to adjacent carbon atoms; and
provided that if either X or Y is hydrogen, then the other one must be alkenyl or alkynyl; or a pharmaceutically acceptable salt thereof, that is effective in treating or preventing such disorder; or (j) an amount of a compound of the formula

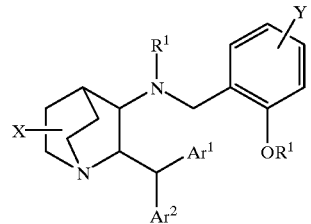

XVIII wherein $Ar^1$ and $Ar^2$ are each, independently, thienyl, phenyl, fluorophenyl, chlorophenyl or bromophenyl;
X is —$CONR^3R^4$, —$CO_2R^3$, $CH_2OR^3$, —$CH_2NR^3R^4$ or —$CONR^3OR^4$;
$R^1$, $R^3$ and $R^4$ are each, independently, hydrogen or alkyl having 1 to 4 carbon atoms;
$R^2$ is alkyl having 1 to 4 carbon atoms;
Y is alkylsulfonyl having 1 to 4 carbon atoms, N-alkyl-N-alkanoylamino (which may be substituted by halogen in the alkanoy moiety) having 1 to 4 carbon atoms in the alkyl and the alkanoyl moieties, N-alkyl-N-alkylsulfonylamino (which may be substituted by halogen in the alkylsulfonyl moiety) having 1 to 4 carbon atoms in the alkyl and the alkyl sulfonyl moieties, alkenyl having 2 to 4 carbon atoms, alkynyl having 2 to 4 carbon atoms, halosubstituted alkyl having 1 to 4 carbon atoms, alkylamino having 1 to 4 carbon atoms, alkanoylamino (which may be substituted by halogen) having 1 to 4 carbon atoms or alkylsulfonylamino (which may be substituted by halogen) having 1 to 4 carbon atoms;
or a pharmaceutically acceptable salt thereof that is effective in treating or preventing disorder; or (k) an amount of a compound of the formula

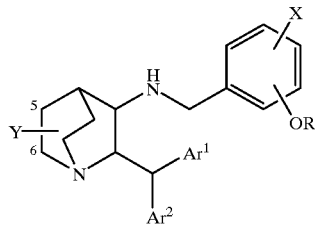

XIX wherein R is $C_1$–$C_6$ alkyl;

X is $C_1$–$C_6$ alkyl having one or more substituents bonded through a heteroatom selected from hydroxy, halogen, $C_1$–$C_6$ alkoxy, $C_2$–$C_6$ alkanoyl, $C_1$–$C_6$ alkanoyloxy, $C_1$–$C_6$ alkylthio, mono $C_1$–$C_6$ alkylamino, di $C_1$–$C_6$ alkylamino, amino, cyano and azido;

$Ar^1$ and $Ar^2$ are each, independently, aryl optionally substituted by one $C_1$–$C_6$ alkyl, $C_1$–$C_6$ alkoxy, $C_1$–$C_6$ alkylthio, halogen, cyano, nitro, phenoxy, mono $C_1$–$C_5$ alkylamino, di $C_1$–$C_6$ alkylamino, halosubstituted $C_1$–$C_6$ alkyl, or halosubstituted $C_1$–$C_6$ alkoxy;

Y is hydrogen, $C_1$–$C_6$ alkyl, $C_2$–$C_6$ alkenyl, $C_3$–$C_8$ cycloalkyl, Z—$(CH_2)_p$—, or W—$(CH_2)_m$—$CHR^2$—$(CH_2)_n$—$NR^1CO$— wherein Y is at the 4-, 5- or 6-position on the quinuclidine ring;

$R^1$ is hydrogen, $C_1$–$C_6$ alkyl, benzyl or —$(CH_2)_r$—W;

$R^2$ is hydrogen or $C_1$–$C_6$ alkyl which may be substituted by one hydroxy, amino, methylthio, mercapto, benzyl, 4-hydroxybenzyl, 3-indolylmethyl or —$(CH_2)_r$—W;

Z is $C_1$–$C_6$ alkoxy, —$CONR^4R^5$, —$CO_2R^4$, —$CHR^4OR^5$, —$CHR^4NR^5R^6$, —$COR^4$, —$CONR^4OR^5$ or optionally substituted aryl;

each W is independently cyano, hydroxymethyl, $C_2$–$C_6$ alkoxymethyl, aminomethyl, mono $C_1$–$C_6$ alkylaminomethyl, di $C_1$–$C_6$ alkylaminomethyl, carboxyl, carbamoyl or $C_1$–$C_6$ alkoxycarbonyl;

$R^4$, $R^5$ and $R^6$ are independently hydrogen, $C_1$–$C_6$ alkyl, $C_1$–$C_6$ alkoxy, $C_3$–$C_8$ cycloalkyl or optionally substituted aryl or heterocyclic group;

p is 0 to 6; and m, n and r are each, independently, 0 to 3;

or a pharmaceutically acceptable salt thereof, that is effective in treating or preventing such disorders; or (l) an amount of a compound of the formula

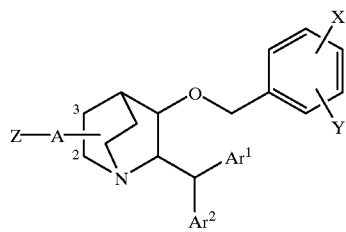

XX wherein X and Y are each hydrogen, halo, $C_1$–$C_6$ alkyl, halosubstituted $C_1$–$C_6$ alkyl, $C_1$–$C_6$ alkoxy, $C_1$–$C_6$ alkylthio, $C_1$–$C_6$ alkylsulfinyl, $C_1$–$C_6$ alkylsulfonyl or tri $C_1$–$C_6$ alkylsilyl;

$Ar^1$ and $Ar^2$ are each aryl optionally substituted by halo;

A is —CO— or —$(CH_2)$—;

Z—A— is at the 2 or 3 position on the quinuclidine ring;

Z is hydroxy, $C_1$–$C_6$ alkoxy, $NR^1R^2$ or $W^1$—$(CH_2)_m$—$CHR^4$—$(CH_2)_n$—$NR^3$ wherein $R^1$ and $R^2$, when taken separately, are each hydrogen or $C_1$–$C_6$ alkyl;

$R^1$ and $R^2$, when taken together with the nitrogen atom to which they are attached, represent piperidino, pyrrolidino, morpholino, thiomorpholino or piperazino;

$R^3$ is hydrogen, $C_1$–$C_6$ alkyl, benzyl or —$(CH_2)_r$—$W^2$;

$R^4$ is hydrogen or $C_1$–$C_6$ alkyl which may be substituted by hydroxy, amino, methylthio, mercapto, benzyl, 4-hydroxylbenzyl, 3-indolylmethyl or —$(CH_2)_s$—$W^3$;

$R^3$ and $R^4$, when taken together, represent $CH_2$ or $CH_2CH_2$;

$W^1$, $W^2$ and $W^3$ are each cyano, hydroxymethyl, $C_2$–$C_6$ alkoxymethyl, aminomethyl, ($C_1$–$C_6$ alkylamino)methyl, (di $C_1$–$C_6$ alkylamino)methyl, carboxyl, ($C_1$–$C_6$ alkyl)carbamoyl, or (di $C_1$–$C_6$ alkyl)carbamoyl, carbamoyl or ($C_1$–$C_6$ alkoxy)carbonyl; and m, n, and s are each 0, 1, 2 or 3;

or a pharmaceutically acceptable salt thereof that is effective in treating or preventing such disorder; or (m) an amount of a compound of the formula

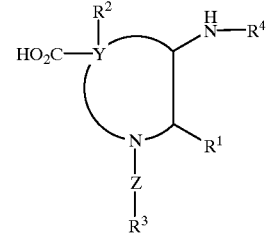

XXI wherein Y is $C_2$–$C_4$ alkylene;

Z is a valence bond or $C_1$–$C_6$ alkylene;

$R^1$ is phenyl, biphenyl, indanyl, naphthyl, thienyl, furyl, pyridyl, thiazolyl, isothiazolyl, oxazolyl, soxazolyl, tetrazolyl, quinolyl, phenyl $C_1$–$C_6$ alkyl- or benzhydryl, wherein each of the ring moieties may ptionally be substituted by one or more substituents independently selected from halogen, $C_1$–$C_6$ alkyl, alosubstituted $C_1$–$C_6$ alkyl, $C_1$–$C_6$ alkoxy and halosubstituted $C_1$–$C_6$ alkoxy;

$R^2$ is hydrogen or $C_1$–$C_6$ alkyl;

$R^3$ is hydrogen, hydroxy, cyano, amino or carboxy; and $R^4$ represents a group of the formula (II) or (III)

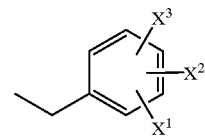

II

-continued

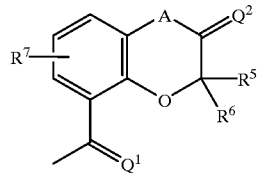

III wherein $X^1$, $X^2$ and $X^3$ are each halo, hydrogen, nitro, $C_1$–$C_6$ alkyl, halosubstituted $C_1$–$C_6$ alkoxy, losubstituted $C_1$–$C_6$ alkoxy, hydroxy, amino, $C_1$–$C_6$ alkylthio, $C_1$–$C_6$ alkylsulfinyl or $C_1$–$C_6$ alkylsulfonyl;

$Q^1$ and $Q^2$ are each $H_2$, oxygen or sulfur;

A is valence bond, methylene, oxygen, sulfur or NH;

$R^5$ and $R^6$ are each hydrogen or $C_1$–$C_6$ alkyl; and $R^6$ is hydrogen, halogen, $C_1$–$C_6$ alkyl, halosubstituted $C_1$–$C_6$ alkyl or $C_1$–$C_6$ alkoxy;

provided that when Z is a valence bond, $R^3$ must be hydrogen;

or a pharmaceutically acceptable salt thereof, that is effective in treating or preventing such disorder.

* * * * *